(12) United States Patent
Gray et al.

(10) Patent No.: US 11,193,931 B2
(45) Date of Patent: Dec. 7, 2021

(54) CELLULAR VAMP CLEAVAGE ASSAY

(71) Applicant: IPSEN BIOPHARM LIMITED, Wrexham (GB)

(72) Inventors: Bryony Gray, Wrexham (GB); Verity Cadd, Wrexham (GB); Matthew Beard, Wrexham (GB)

(73) Assignee: IPSEN BIOPHARM LIMITED, Wrexham (GB)

( * ) Notice: Subject to any disclaimer, the term of this patent is extended or adjusted under 35 U.S.C. 154(b) by 0 days.

(21) Appl. No.: 16/335,358

(22) PCT Filed: Oct. 18, 2017

(86) PCT No.: PCT/EP2017/076569
§ 371 (c)(1),
(2) Date: Mar. 21, 2019

(87) PCT Pub. No.: WO2018/073288
PCT Pub. Date: Apr. 26, 2018

(65) Prior Publication Data
US 2019/0219575 A1    Jul. 18, 2019

(30) Foreign Application Priority Data
Oct. 18, 2016  (EP) .................................. 16194390

(51) Int. Cl.
| G01N 33/569 | (2006.01) |
| C07K 14/33 | (2006.01) |
| C07K 16/12 | (2006.01) |
| C12Q 1/37 | (2006.01) |
| C07K 14/47 | (2006.01) |
| C07K 16/18 | (2006.01) |

(52) U.S. Cl.
CPC ........ *G01N 33/56911* (2013.01); *C07K 14/33* (2013.01); *C07K 14/47* (2013.01); *C07K 16/1282* (2013.01); *C07K 16/18* (2013.01); *C12Q 1/37* (2013.01); *C07K 2317/30* (2013.01); *C07K 2317/92* (2013.01); *C07K 2319/00* (2013.01); *G01N 2333/33* (2013.01)

(58) Field of Classification Search
None
See application file for complete search history.

(56) References Cited

U.S. PATENT DOCUMENTS

| 7,227,010 B2* | 6/2007 | Smith .................... A61K 39/08 435/235.1 |
| 9,562,903 B2* | 2/2017 | Kalkum ............... G01N 33/542 |
| 2004/0126810 A1 | 7/2004 | Roques et al. |
| 2006/0024763 A1 | 2/2006 | Schmidt et al. |
| 2007/0104737 A1* | 5/2007 | Smith .................... C12N 9/52 424/239.1 |
| 2012/0164657 A1 | 6/2012 | Johnson et al. |
| 2013/0345398 A1* | 12/2013 | Smith .................... C07K 14/33 530/350 |
| 2014/0287433 A1* | 9/2014 | Weingart ........... G01N 33/5432 435/7.4 |
| 2019/0219575 A1* | 7/2019 | Gray .................. C07K 16/1282 |

FOREIGN PATENT DOCUMENTS

| EP | 0763131 B1 | 8/1999 | |
| WO | 9734620 A1 | 9/1997 | |
| WO | WO-2013011055 A1 * | 1/2013 | ......... G01N 33/5432 |
| WO | WO-2018073288 A1 * | 4/2018 | ............. C07K 16/18 |

OTHER PUBLICATIONS

Gray et al Toxicology in Vitro, 2018 48:255-261. Available online: Jan. 31, 2018 (Year: 2018).*
Hackett et al, Toxins, Oct. 2018, 195, 18 pages. published: May 11, 2018 (Year: 2018).*
Kozaki etal, Infection and Immunity, Oct. 1998, 66/10:4811-4816. (Year: 1998).*
Masuyer et al, Journal of Structural Biology 174 (2011) 52-57. available online: Nov. 13, 2010 (Year: 2010).*
Peng L, Adler M, Demogines A, Borrell A, Liu H, et al. (2014) Widespread Sequence Variations in VAMP1 across Vertebrates Suggest a Potential Selective Pressure from Botulinum Neurotoxins. PLoS Pathog 10(7): e1004177. doi:10.1371/journal.ppat. 1004177. published Jul. 10, 2014 (Year: 2014).*
Rao et al., JBC, vol. 279, No. 19, Issue of May 7, pp. 20471-20479, 2004. published:Mar. 1, 2014 (Year: 2014).*
Rossetto et al, Nature, Dec. 1, 1994, 372:415-416 (Year: 1994).*
Savage et al, Toxins, 2015, 7:1544-1555. Published: May 6, 2015 (Year: 2015).*
Moghaddam et al., Biologicals, 38:113-119 (2010).
Binz et al., Toxins, 2:665-682 (2010).
Sikorra et al., J. Biol. Chem., 283:21145-21152 (2008).
Hallis et al., Journal of Clinical Microbiology, 34:1934-1938 (1996).
Wictome et al., Applied and Environmental Microbiology, 65:3787-3792 (1999).
Kegel et al., Toxicology In Vitro, 21:1641-1649 (2007).
Kalb et al., FEBs Letters, 586:109-115 (2011).
Pellett et al., FEBs Letters, 581:4803-4808 (2007).

* cited by examiner

*Primary Examiner* — Nita M. Minnifield
(74) *Attorney, Agent, or Firm* — Gene J. Yao; Barnes & Thornburg LLP

(57) ABSTRACT

A VAMP epitope suitable for generating an antibody against a VAMP C-terminal neurotoxin cleavage product. Method of using such an epitope to generate an antibody against cleaved VAMP. Method of using such an antibody to assay for cleavage of a VAMP by clostridial neurotoxin.

Figure 3:
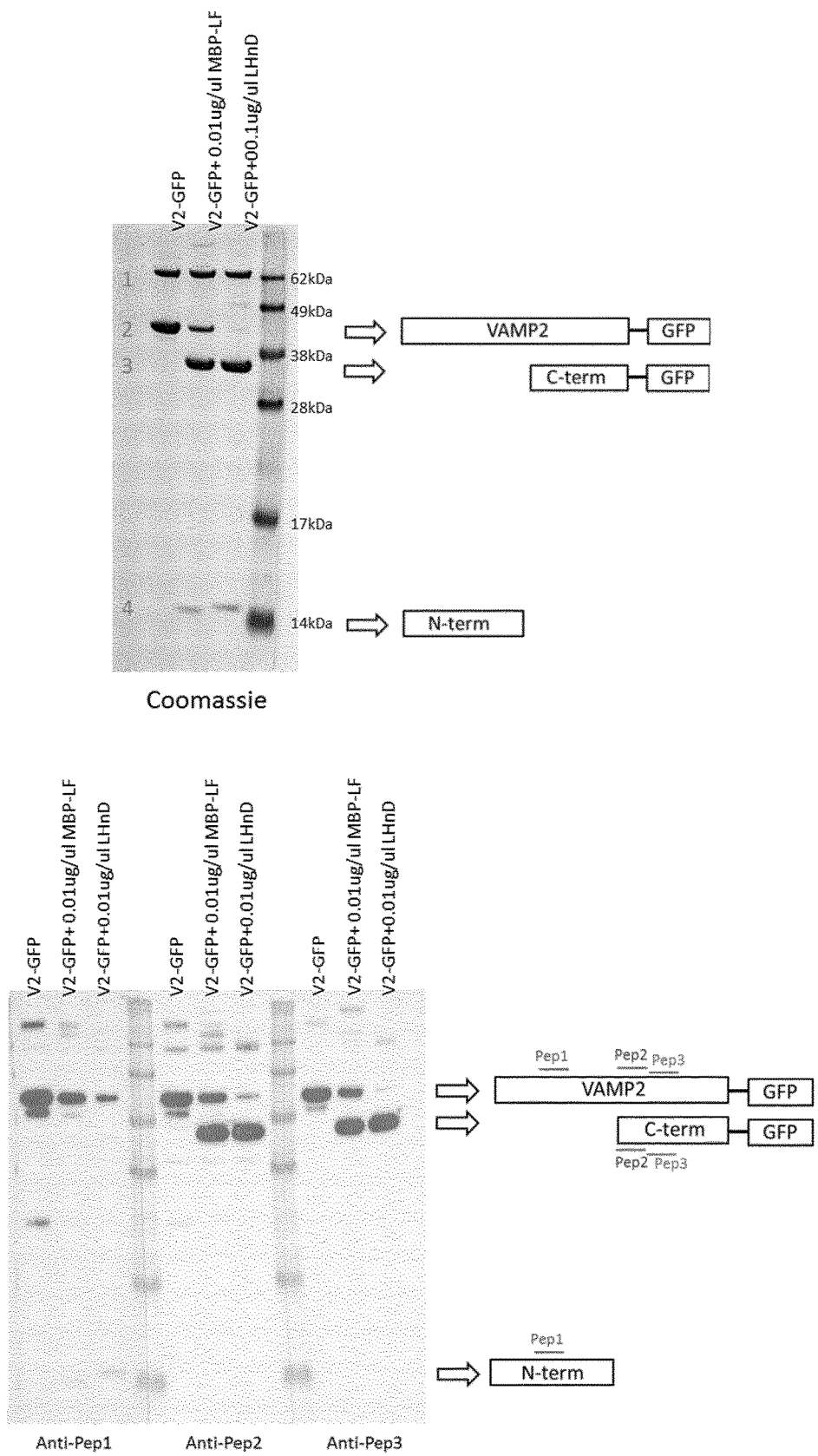
Figure 3:
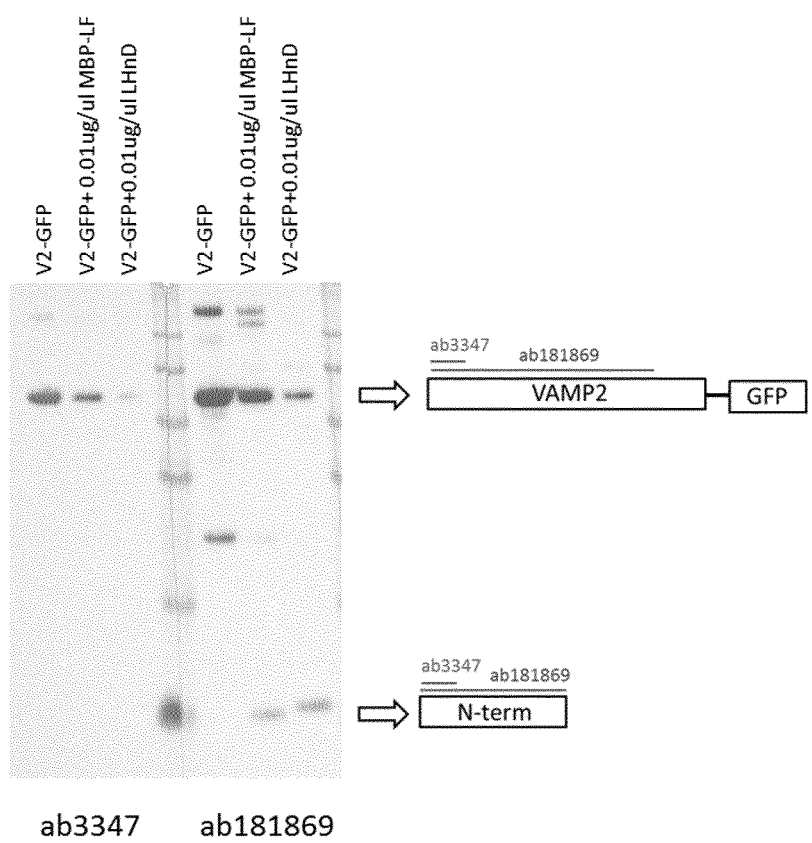

17 Claims, 7 Drawing Sheets
Specification includes a Sequence Listing.

Figure 1A

```
                                                                                             BoNT/F BoNT/D&DC       BoNT/B&TeTx
                                                                                    BoNT/F5&FA         BoNT/X          BoNT/G
SEQ ID NO 9  - VAMP1_Rat (Q63666)   MSAPAQPPAEGTEGAAPGGGPPGPPPNTTSNRRLQQTQAQVEEVVDIMRVNVDKVLERDQKLSELDDRADALQAGASVFESSAAKLKRKYWWKNCKMMIMLGAICAIIVVVIVIYIFT   118
SEQ ID NO 10 - VAMP1_Human (P23763) MSAPAQPPAEGTEGTAPGGGPPGPPPNMTSNRRLQQTQAQVEEVVDIIRVNVDKVLERDQKLSELDDRADALQAGASQFESSAAKLKRKYWWKNCKMMIMLGAICAIIVVVIVIYFFT   118

SEQ ID NO 11 - VAMP2_Rat (P63045)   MSATAATVPP--AAPAGEGGPPAPPPNLTSNRRLQQTQAQVDEVVDIMRVNVDKVLERDQKLSELDDRADALQAGASQFETSAAKLKRKYWWKNLKMMIILGVICAIILIIIIVYFST   116
SEQ ID NO 12 - VAMP2_Human (P63027) MSATAATAPP--AAPAGEGGPPAPPPNLTSNRRLQQTQAQVDEVVDIMRVNVDKVLERDQKLSELDDRADALQAGASQFETSAAKLKRKYWWKNLKMMIILGVICAIILIIIIVYFST   116

SEQ ID NO 13 - VAMP3_Rat (P63025)   MSTGV--------------PSGSSAATGSNRRLQQTQNQVDEVVDIMRVNVDKVLERDQKLSELDDRADALQAGASQFETSAAKLKRKYWWKNCKMWAIGISVLVIIVIIIIVWCVS   103
SEQ ID NO 14 - VAMP3_Human (Q15836) MST-------------------GPTAATGSNRRLQQTQNQVDEVVDIMRVNVDKVLERDQKLSELDDRADALQAGASQFETSAAKLKRKYWWKNCKMWAIGITVLVIFIIIIIVWVVSS   100
                                                                                  SNARE motif
```

Figure 1B

```
SEQ ID NO 42 - VAMP4_Rat (D4A560)   ------------------------------------------------------------------------------------MPPKFKRHLNDDDVTGSVKSERRNLLEDDSDEEE    34
SEQ ID NO 43 - VAMP4_Human (O75379) ------------------------------------------------------------------------------------MPPKFKRHLNDDDVTGSVKSERRNLLEDDSDEEE    34

SEQ ID NO 44 - VAMP5_Rat (Q9Z2J5)   ---------------------------------------------------------------------------------------------------------------------
SEQ ID NO 45 - VAMP5_Human (O95183) ---------------------------------------------------------------------------------------------------------------------

SEQ ID NO 46 - Ykt6_Rat (Q5EGY4)    MKLYSLSVFYKGEPKAVLLKAAYDVSSFSFFQRSSVQEFMTFTSQLIVERSAKGSRASVKEQEYLCHVYVRSDSLAGVVIADSEYPSRVAFTLLEKVLDEFSKQVDRIDWPVGSPATIHY   120
SEQ ID NO 43 - Ykt6_Human (O15498)  MKLYSLSVLYKGEAKVVLLKAAYDVSSFSFFQRSSVQEFMTFTSQLIVERSSKGTRASVKEQDYLCHVYVRNDSLAGVVIADNEYPSRVAFTLLEKVLDEFSKQVDRIDWPVGSPATIHY   120

BoNT/X
SEQ ID NO 42 - VAMP4_Rat (D4A560)   DFFLRGPSGPRFGPRNDKIKHVQNQVDEVIDVMQENITKVIERGERLDELQDKSESLSDNATAFSNRSKQLRRQMWWRGCKIKAIMALAAAILLLMIITQIILHLKK   141
SEQ ID NO 43 - VAMP4_Human (O75379) DFFLRGPSGPRFGPRNDKIKHVQNQVDEVIDVMQENITKVIERGERLDELQDKSESLSDNATAFSNRSKQLRRQMWWRGCKIKAIMALVAAILLLVIIILIVMKYRT   141

SEQ ID NO 44 - VAMP5_Rat (Q9Z2J5)   -------------MAGKELERCQRQADQVTEIMLNNFDKVLERDGKLSELQQRSDQLLDMSSAFSKTTKTLAQQKRWENIRCRVYLGLAVAGGLLLILVVLLVIFLP-SGEDSSKP   102
SEQ ID NO 45 - VAMP5_Human (O95183) -------------MAGIELERCQQQANEVTEIMRNNFGKVLERGVKLAELQQRSDQLLDMSSTFNKTTQNLAQKKCWENIRYRICVGLVVVGVLLIIILIVLLVVFLPQSSDSSSAPRTQDAGIASGPGN   116

SEQ ID NO 46 - Ykt6_Rat (Q5EGY4)    TALDGHLSRYQNPREADPMSKVQAELDETKIILHNTMESLLERGEKLDDLVSKSEVLGTQSKAFYKTARKQNSCCAIM   198
SEQ ID NO 43 - Ykt6_Human (O15498)  PALDGHLSRYQNPREADPMTKVQAELDETKIILHNTMESLLERGEKLDDLVSKSEVLGTQSKAFYKTARKQNSCCAIM   198
                                                           SNARE motif

```
                                                                                    BoNT/F
                                                   Pep1                              ↓
Q63666|VAMP1_RAT    MSAPAQPPAEGTEGAAPGGGPPPNTTSNRRLQQTQAQVEEVVDIMRVNVDKVLERDQ 60
P23763|VAMP1_HUMAN  MSAPAQPPAEGTEGTAPGGGPPPGPPPNMTSNRRLQQTQAQVEEVVDIRVNVDKVLERDQ 60
P63045|VAMP2_RAT    MSATAATVPP--AAPAGEGGPPAPPPNLTSNRRLQQTQAQVDEVVDIMRVNVDKVLERDQ 58
P63027|VAMP2_HUMAN  MSATAATAPP--AAPAGEGGPPAPPPNLTSNRRLQQTQAQVDEVVDIMRVNVDKVLERDQ 58
P63025|VAMP3_RAT    MSTGV-----------------PSGSSAATGSNRRLQQTQNQVDEVVDIMRVNVDKVLERDQ 45
Q15836|VAMP3_HUMAN  MST--------------------GPTAATGSNRRLQQTQNQVDEVVDIMRVNVDKVLERDQ 41

BoNT/D         BoNT/B

| Toxin | pEC$_{50}$ | n |
|---|---|---|
| BoNT/A1 | 12.38 ± 0.14 | 3 |
| BoNT/F1 | 10.77 ± 0.12 | 3 |
| BoNT/FA | 12.75 ± 0.09 | 4 |

FIGURE 5

CELLULAR VAMP CLEAVAGE ASSAY

CROSS REFERENCE TO RELATED APPLICATIONS

This application is a U.S. national stage filing of International Patent Application No. PCT/FT 2017/076569, filed Oct. 18, 2017, claims the priority of European Application No. 16194390.7, filed Oct. 18, 2016.

REFERENCE TO SEQUENCE LISTING

The instant application contains a Sequence Listing that has been submitted electronically in ASCII format and is hereby incorporated by reference in its entirety. Said ASCII copy, created on Mar. 22, 2019, is named 16335358SeqListing.txt and is 155,473 bytes in size.

FIELD OF THE INVENTION

The present invention relates to cell based assays for VAMP cleaving clostridial neurotoxins.

BACKGROUND

Bacteria in the genus *Clostridia* produce highly potent and specific protein toxins, which can poison neurons and other cells to which they are delivered. Examples of such clostridial toxins include the neurotoxins produced by *C. tetani* (Tetanus neurotoxin) and by *C. botulinum* (Botulinum neurotoxins serotypes A to G), as well as those produced by *C. baratii* and *C. butyricum*.

Clostridial neurotoxins act by inhibiting cholinergic transmission in the peripheral nervous system, in particular at the neuromuscular junction. In nature, clostridial neurotoxins are synthesised as a single-chain polypeptide that is modified post-translationally by a proteolytic cleavage event to form two polypeptide chains joined together by a disulphide bond. Cleavage occurs at a specific cleavage site, often referred to as the activation site, which is located between the cysteine residues that provide the inter-chain disulphide bond. It is this di-chain form that is the active form of the toxin. The two chains are termed the heavy chain (H-chain), which has a molecular mass of approximately 100 kDa, and the light chain (L-chain), which has a molecular mass of approximately 50 kDa. The H-chain comprises an N-terminal translocation component ($H_N$ domain) and a C-terminal targeting component ($H_C$ domain). The cleavage site is located between the L-chain and the $H_N$ domain. Following binding of the $H_C$ domain to its target neuron and internalisation of the bound toxin into the cell via an endosome, the $H_N$ domain translocates the L-chain across the endosomal membrane and into the cytosol, and the L-chain provides a protease function (also known as a non-cytotoxic protease).

Non-cytotoxic proteases act by proteolytically cleaving intracellular transport proteins known as SNARE proteins (e.g. SNAP25, VAMP, or syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. The acronym SNAP25 derives from the term Synaptosome Associated Protein of 25 kilo daltons. The acronym VAMP derives from the term Vesicle Associated Membrane Protein. SNARE proteins are integral to intracellular vesicle fusion, and thus to secretion of molecules via vesicle transport from a cell. The protease function is a zinc-dependent endopeptidase activity and exhibits high substrate specificity for SNARE proteins. Accordingly, once delivered to a desired target cell, the non-cytotoxic protease is capable of inhibiting cellular secretion from the target cell. The L-chain proteases of clostridial neurotoxins are non-cytotoxic proteases that cleave SNARE proteins. The L-chain proteases of BoNT/B, BoNT/D, BoNT/F, BoNT/G, BoNT/X and TeNT cleave VAMPs (also referred to as synaptobrevins), the L-chain proteases of BoNT/A and BoNT/E cleave SNAP25 and the L-chain protease of BoNT/C cleaves both SNAP25 and syntaxin, which result in the inhibition of neurotransmitter release and consequent neuroparalysis (Rossetto, O. et al., "Botulinum neurotoxins: genetic, structural and mechanistic insights." Nature Reviews Microbiology 12.8 (2014): 535-549) (Zhang et al., "Identification and characterization of a novel botulinum neurotoxin"; Nature Communications, 2017, 8:14130).

Clostridial neurotoxins target and enter neurons by binding to their specific receptors through their receptor binding domains ($H_C$), which are well-defined in the literature (Schiavo, G., Matteoli, M. & Montecucco, C. Neurotoxins affecting neuroexocytosis, Physiol Rev, 2000, 80, 717-766). Receptor binding dictates the efficacy and specificity of BoNTs to recognize neurons. BoNT/B, D-C, and G share two homologous synaptic vesicle proteins synaptotagmin I and II (Syt I/II) as their receptors, while BoNT/A, E, D, F and TeNT use another synaptic vesicle protein SV2. In addition to protein receptors, all BoNTs require lipid co-receptor gangliosides, which are abundant on neuronal surfaces.

Clostridial neurotoxins are used in therapy to treat motor and autonomic disorders. Several BoNT/A products (including Botox®, Dysport® and Xeomin®) and one BoNT/B product (Neurobloc®/Myobloc®) are approved by regulatory agencies for use in humans.

Traditionally, the potency of BoNT pharmaceutical products has been quantified in MLD50 (mouse lethal dose 50) units, one unit corresponding to the median lethal intraperitoneal dose in mice. However, the MLD50 unit for botulinum toxins is not a standardised unit. Indeed, assays used by different manufacturers of marketed toxins differ in particular in the choice of dilution buffer (Straughan, D. W., 2006, ATLA 34(3), 305-313; Hambleton and Pickett, Hambleton, P., and A. M. Pickett., 1994, Journal of the Royal Society of Medicine 87.11: 719). In addition, because of ethical concerns and recent regulations, it is now preferable to avoid the use of animal based potency assays. Cell-based potency assays avoid the requirement for animal testing and related ethical concerns.

Following cellular intoxication, the potency of a clostridial neurotoxin can be measured by assessing the degree of SNARE cleavage within the target cell, for example by Western blotting. Alternatively, SNARE cleavage can be detected and quantified using a sandwich ELISA method. Such methods work well for SNAP25 and syntaxin cleavage (see eg. Pellett, Sabine, et al. "Comparison of the primary rat spinal cord cell (RSC) assay and the mouse bioassay for botulinum neurotoxin type A potency determination." Journal of pharmacological and toxicological methods 61.3 (2010):304-310; Fernindez-Salas, Ester, et al. "Botulinum neurotoxin serotype A specific cell-based potency assay to replace the mouse bioassay." PLoS One 7.11 (2012): e49516; Kalandakanond S et al. "Cleavage of intracellular substrates of botulinum toxins A, C and D in mammalian target tissue" The Journal of Pharmacology and Experimental Therapeutics (2001):749-755; Peng L et al. "Cytotoxicity of botulinum neurotoxins reveals a direct role of syntaxin 1 and SNAP25 in neuron survival." Nature Communications (2013): 4:1472). However, to date the cleavage product for VAMPs from cellular lysates has proved extremely difficult to detect. Indeed, although VAMP cleavage-specific antibodies that recognise cleaved VAMP are available and suitable for detection of VAMP cleavage in extracellular or cell fraction assays (Hallis, Bassam, B. A. James, and Clifford C. Shone. "Development of novel assays for botulinum type A and B neurotoxins based on their endopeptidase activities." Journal of clinical microbiology 34.8 (1996): 1934-1938; Kegel, B., et al. "An in vitro assay for detection of tetanus neurotoxin activity: Using antibodies for recognizing the proteolytically generated cleavage product." Toxicology in Vitro 21.8 (2007): 1641-1649; Fujita-Yoshigaki, Junko, et al. "Vesicle-associated Membrane Protein 2 Is Essential for cAMP-regulated Exocytosis in Rat Parotid Acinar Cells The Inhibition of cAMP-dependent Amylase Release by Botulinum Neurotoxin B." Journal of Biological Chemistry 271.22 (1996): 13130-13134), these antibodies do not detect cleaved VAMP in cellular studies.

The general consensus in the field was so far that the cleaved VAMP product must be degraded very quickly in the cell and therefore does not contribute to the longevity of BoNT action (Foran, Patrick G., et al. "Evaluation of the Therapeutic Usefulness of Botulinum Neurotoxin B, Cl, E, and F Compared with the Long Lasting Type A Basis for Distinct Durations of Inhibition of Exocytosis in Central Neurons." Journal of biological chemistry 278.2 (2003): 1363-1371). However, Schiavo et al. have shown both VAMP cleavage products are present in small synaptic vesicle fractions prepared from rat cerebral cortex when treated with BoNT/B and TeNT using Coomassie blue staining (Schiavo G., et al (1992), Tetanus and Botulinum-B neurotoxins block neurotransmitter release by proteolytic cleavage of synaptobrevin. Nature 359 p 832-835). This suggests VAMP products from a cellular source can be present, although the synaptosome preparation may well not contain all the proteases present in a total cell lysate. Dong et al (2004) describe that in PC12 cells expressing YFP-Syb (FL)-CFP, signals from both VAMP products are detectable after cleavage by BoNT/B, and that the YFP-N-terminal cleaved VAMP product disperses into the cytosol and redistributes itself to the nucleus, whereas the CFP-C-terminal product remains localised to the vesicle (Dong M., et al (2004) Using fluorescent sensors to detect botulinum neurotoxin activity in vitro and in living cells. PNAS 101 (41) p 14701-14706). This evidence suggests both VAMP products could be present, but as yet unknown cellular processes are hampering the recognition of an antibody to the N-terminal product. It is therefore standard practice to measure VAMP cleavage by disappearance of the full-length band only (see eg. Pellett, Sabine, et al. "A neuronal cell-based botulinum neurotoxin assay for highly sensitive and specific detection of neutralizing serum antibodies." FEBS letters 581.25 (2007): 4803-4808; Whitemarsh, Regina C M, et al. "Novel application of human neurons derived from induced pluripotent stem cells for highly sensitive botulinum neurotoxin detection Biological Sciences: Applied Biological Sciences." Toxicological Sciences, 2012, 126(2):426-435). However, assays based on the loss of a signal convey a risk of error as there may be discrepancies in total protein loading which would then cause either an over- or underestimation of VAMP disappearance. A house keeping protein that is unchanged during BoNT treatment can be used to normalise VAMP disappearance to the density of the control protein. The disadvantage here is that the signal between the antibodies needs to be matched and in the linear scale in order to detect any differences for normalisation purposes. Although qualitatively this may be a reasonable indication of BoNT activity, it is not suitable for more detailed quantification and in particular for determining the potency of pharmaceutical BoNT formulations.

There is thus a need for cellular VAMP cleavage assays based on a gain of signal readout.

SUMMARY OF INVENTION

In a first aspect, the invention provides an antigenic polypeptide comprising a VAMP epitope, wherein said antigenic polypeptide consists of 10 to 65 amino acid residues, wherein said VAMP epitope comprises an amino acid sequence which is at least 90% identical to a VAMP sequence comprising at least 8 amino acid residues which are immediately C-terminal to a clostridial neurotoxin cleavage site in said VAMP.

In another aspect, the invention relates to a polypeptide comprising the antigenic polypeptide of the invention, wherein the polypeptide does not comprise a region of greater than 17, preferably 16, more preferably 15 consecutive amino acids having 100% sequence identity to a naturally-occurring VAMP amino acid sequence.

In another aspect, the invention provides an antigenic protein comprising a polypeptide according to the invention covalently linked to a carrier.

In another aspect, the invention provides the use of an antigenic polypeptide or protein according to the invention, to generate antibodies against a C-terminal VAMP cleavage product. In one embodiment, the epitope of the invention is used to generate a polyclonal antibody against a C-terminal VAMP cleavage product. In another embodiment, the epitope of the invention is used to generate a monoclonal antibody against a C-terminal VAMP cleavage product.

In another aspect, the invention provides an antibody that binds to an antigenic polypeptide or protein of the invention.

In another aspect, the invention provides the use of an antibody according to the invention in a gain of signal cellular assay for VAMP cleavage by a VAMP cleaving clostridial neurotoxin.

In another aspect, the invention provides a method for determining cleavage of VAMP by a VAMP cleaving clostridial neurotoxin in a cell, comprising:
  a) contacting the cell with the clostridial neurotoxin under conditions suitable for clostridial neurotoxin activity;
  b) contacting the cytoplasmic content of said cell with a first detection antibody against the C-terminal VAMP cleavage product following cleavage of a VAMP by the VAMP cleaving clostridial neurotoxin under conditions suitable for the binding of the first detection antibody to the C-terminal VAMP cleavage product, wherein said first detection antibody is an antibody according to the invention; and
  c) detecting by a suitable means the binding of said first detection antibody to the C-terminal VAMP cleavage product.

In another aspect, the invention provides a method for determining immunoresistance to a VAMP cleaving clostridial neurotoxin in a subject, comprising:
a) adding a VAMP cleaving clostridial neurotoxin to a test sample obtained from the subject;
b) contacting a cell with the test sample of step a) under conditions suitable for clostridial neurotoxin activity;
c) contacting the cytoplasmic content of said cell with a first detection antibody against the C-terminal VAMP cleavage product following cleavage of a VAMP by the VAMP cleaving clostridial neurotoxin under conditions suitable for the binding of the first detection antibody to the C-terminal VAMP cleavage product, wherein said first detection antibody is an antibody according to the invention;
d) detecting by a suitable means the binding of the first detection antibody to the C-terminal VAMP cleavage product;
e) quantifying the amount of the C-terminal VAMP cleavage product bound to the first detection antibody;
f) repeating steps a) to e) with a negative control sample instead of a test sample; and
g) comparing the amount of the C-terminal VAMP cleavage product bound to said first detection antibody in steps (e) and (f), wherein detection of a lower amount of the C-terminal VAMP cleavage product bound to said first detection antibody in step (e) relative to the amount of the C-terminal VAMP cleavage product bound to said first detection antibody in step (f) is indicative of the presence of neutralizing antibodies against the VAMP cleaving clostridial neurotoxin.

In another aspect, the invention provides a kit comprising a cell which is susceptible to intoxication by a VAMP cleaving neurotoxin; and a first detection antibody against cleaved VAMP, wherein said first detection antibody is an antibody according to the invention.

DETAILED DESCRIPTION OF THE INVENTION

The present invention is based on a finding by the inventors that it was possible to generate antibodies suitable for use in a cellular VAMP cleavage assay based on a gain of signal readout.

In particular, the inventors have shown that, in order to detect VAMP cleavage in vitro, it is key to detect epitopes located on the C-terminal side of BoNT cleavage site. Indeed, the inventors have demonstrated herein the successful detection of a neuronal VAMP2 cleavage product by Western Blot (WB) using antibodies binding epitopes located on the C-terminal side of the BoNT/F and/or BoNT/D and/or BoNT/B cleavage sites, which are adjacent to the BoNT/D and/or BoNT/F and/or BoNT/B cleavage sites. In particular, such antibodies are capable of detecting both full-length VAMP and the cleaved product in a cell lysate. This tool enables the quantitative assessment of the potency of BoNT in a gain of signal cellular assay by monitoring the appearance of the cleaved VAMP product.

In a first aspect, the invention provides an antigenic polypeptide comprising a VAMP epitope, wherein said antigenic polypeptide consists of 10 to 65 amino acid residues, wherein said VAMP epitope comprises an amino acid sequence which is at least 90% identical to a VAMP sequence comprising at least 8 amino acid residues which are immediately C-terminal to a clostridial neurotoxin cleavage site in said VAMP.

The term "clostridial neurotoxin" as used herein means any polypeptide that enters a neuron and inhibits neurotransmitter release. This process encompasses the binding of the neurotoxin to a low or high affinity receptor, the internalisation of the neurotoxin, the translocation of the endopeptidase portion of the neurotoxin into the cytoplasm and the enzymatic modification of the neurotoxin substrate. More specifically, the term "clostridial neurotoxin" encompasses any polypeptide produced by Clostridium bacteria that enters a neuron and inhibits neurotransmitter release, and such polypeptides produced by recombinant technologies or chemical techniques. It is the di-chain form that is the active form of the neurotoxin. The two chains are termed the heavy chain (H-chain), which has a molecular mass of approximately 100 kDa, and the light chain (L-chain), which has a molecular mass of approximately 50 kDa. Clostridial neurotoxins include botulinum neurotoxins (BoNTs) and Tetanus neurotoxin (TeNT). BoNT serotypes A to G can be distinguished based on inactivation by specific neutralising anti-sera, with such classification by serotype correlating with percentage sequence identity at the amino acid level. BoNT proteins of a given serotype are further divided into different subtypes on the basis of amino acid percentage sequence identity.

An example of a BoNT/A neurotoxin amino acid sequence is provided as SEQ ID NO: 1 (UniProt accession number A5HZZ9). An example of a BoNT/B neurotoxin amino acid sequence is provided as SEQ ID NO: 2 (UniProt accession number BIINP5). An example of a BoNT/C neurotoxin amino acid sequence is provided as SEQ ID NO: 3 (UniProt accession number P18640). An example of a BoNT/D neurotoxin amino acid sequence is provided as SEQ ID NO: 4 (UniProt accession number P19321). An example of a BoNT/E neurotoxin amino acid sequence is provided as SEQ ID NO: 5 (NCBI RefSeq accession number WP_003372387). An example of a BoNT/F neurotoxin amino acid sequence is provided as SEQ ID NO: 6 (UniProt accession number Q57236). An example of a BoNT/G neurotoxin amino acid sequence is provided as SEQ ID NO: 7 (NCBI RefSeq accession number WP_039635782). An example of a BoNT/X neurotoxin amino acid sequence is provided as SEQ ID NO: 41 (Genbank accession number BAQ12790.1). An example of a TeNT amino acid sequence is provided as SEQ ID NO: 8 (UniProt accession number P04958).

The term "$H_C$ domain" as used herein means a functionally distinct region of the neurotoxin heavy chain with a molecular weight of approximately 50 kDa that enables the binding of the neurotoxin to a receptor located on the surface of the target cell. The $H_C$ domain consists of two structurally distinct subdomains, the "$H_{CN}$ subdomain" (N-terminal part of the $H_C$ domain) and the "$H_{CC}$ subdomain" (C-terminal part of the $H_C$ domain), each of which has a molecular weight of approximately 25 kDa.

The term "$LH_N$ domain" as used herein means a neurotoxin that is devoid of the $H_C$ domain and consists of an endopeptidase domain ("L" or "light chain") and the domain responsible for translocation of the endopeptidase into the cytoplasm ($H_N$ domain of the heavy chain).

Exemplary L, $H_N$, $H_{CN}$ and $H_{CC}$ domains are shown in table 1.

TABLE 1

Exemplary L, $H_N$, $H_{CN}$ and $H_{CC}$ domains

| Clostridial neurotoxin | Accession Number | SEQ ID NO | L | $H_N$ | $H_{CN}$ | $H_{CC}$ |
|---|---|---|---|---|---|---|
| BoNT/A1 | A5HZZ9 | 1 | 1-448 | 449-872 | 873-1094 | 1095-1296 |
| BoNT/B1 | B1INP5 | 2 | 1-441 | 442-859 | 860-1081 | 1082-1291 |
| BoNT/C1 | P18640 | 3 | 1-449 | 450-867 | 868-1095 | 1096-1291 |
| BoNT/D | P19321 | 4 | 1-442 | 443-863 | 864-1082 | 1083-1276 |
| BoNT/E1 | WP_003372387 | 5 | 1-423 | 424-846 | 847-1069 | 1070-1252 |
| BoNT/F1 | Q57236 | 6 | 1-439 | 440-865 | 866-1087 | 1088-1278 |
| BoNT/G | WP_039635782 | 7 | 1-446 | 447-864 | 865-1089 | 1090-1297 |
| BoNT/X | BAQ12790.1 | 41 | 1-439 | 440-891 | 892-1105 | 1106-1306 |
| TeNT | P04958 | 8 | 1-456 | 457-880 | 881-1111 | 1112-1315 |

The above-identified reference sequences should be considered a guide, as slight variations may occur according to sub-serotypes. By way of example, US 2007/0166332 (hereby incorporated by reference in its entirety) cites slightly different clostridial sequences.

Vesicle-associated membrane proteins (VAMPs) are a family of SNARE proteins which have a similar structure and are involved in vesicle fusion and exocytosis, in particular neurotransmitter release. VAMPs are members of a family of SNARE proteins, which is called the Synaptobrevin family and includes members such as VAMP1, VAMP2 (both also known as synaptobrevins), VAMP3 (also known as cellubrevin), VAMP4, VAMP5, VAMP7 (also known as SYBL1, or tetanus-insensitive VAMP), VAMP8 (also known as endobrevin), YKT6, SEC22A and others. VAMP1, VAMP2 and VAMP3 are cleaved by the light chains of BoNT/B, BoNT/D, BoNT/F, BoNT/G, BoNT/X and TeNT. BoNT/X also cleaves VAMP4, VAMP5 and YKT6.

The term "VAMP epitope" as used herein means a portion of a VAMP protein to which an antibody binds.

In a preferred embodiment, the antigenic polypeptide of the invention consists of 10 to 65, 10 to 60, 10 to 55, 10 to 50, 10 to 45, 10 to 40, 10 to 35, 10 to 30, 10 to 25, 10 to 20, 10 to 19, 10 to 18, 10 to 17, 10 to 16 or 10 to 15 amino acid residues, preferably 10 to 15 amino acid residues. For example, the antigenic polypeptide of the invention may consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64 or 65 amino acid residues.

In a preferred embodiment, the antigenic polypeptide of the invention comprises, or consists of, a VAMP epitope which comprises an amino acid sequence which is at least 90%, 91%, 92%, 93%, 94%, 95%, 96%, 97%, 98%, 99%, or is 100% identical to a VAMP sequence comprising at least 8, 9, 10, 11, 12, 13, 14, 15, 16 or 17 amino acid residues which are immediately C-terminal to a clostridial neurotoxin cleavage site in said VAMP.

Amino acid sequences of naturally-occurring VAMPs, in particular rat and human VAMP1, VAMP2, VAMP3, VAMP4, VAMP5 and YKT6, and their corresponding clostridial neurotoxin VAMP cleavage sites are shown in table 2 and FIG. 1.

TABLE 2

Clostridial neurotoxin VAMP cleavage sites

| VAMP | SEQ ID NO | BoNT/F5 & BoNT/FA | Other BoNT/F | BoNT/D & BoNT/DC | BoNT/B & TeNT | BoNT/G | BoNT/X |
|---|---|---|---|---|---|---|---|
| VAMP1_Rat (Q63666) | 9 | Leu56-Glu57 | Gln60-Lys61 | Lys61-Leu62 | Not cleaved | Ala83-Ala84 | Arg68-Ala69 |
| VAMP1_human (P23763) | 10 | Leu56-Glu57 | Gln60-Lys61 | Lys61-Leu62 | Gln78-Phe79 | Ala83-Ala84 | Arg68-Ala69 |
| VAMP2_Rat (P63045) | 11 | Leu54-Glu55 | Gln58-Lys59 | Lys59-Leu60 | Gln76-Phe77 | Ala81-Ala82 | Arg66-Ala67 |
| VAMP2_human (P63027) | 12 | Leu54-Glu55 | Gln58-Lys59 | Lys59-Leu60 | Gln76-Phe77 | Ala81-Ala82 | Arg66-Ala67 |
| VAMP3_Rat (P63025) | 13 | Leu41-Glu42 | Gln45-Lys46 | Lys46-Leu47 | Gln63-Phe64 | Ala68-Ala69 | Arg53-Ala54 |
| VAMP3_human (Q15836) | 14 | Leu37-Glu38 | Gln41-Lys42 | Lys42-Leu43 | Gln59-Phe60 | Ala64-Ala65 | Arg49-Ala50 |
| VAMP4_Rat (D4A560) | 42 | Not cleaved | Not cleaved | Not cleaved | Not cleaved | Not cleaved | Lys87-Ser88 |
| VAMP4_human (O75379) | 43 | Not cleaved | Not cleaved | Not cleaved | Not cleaved | Not cleaved | Lys87-Ser88 |
| VAMP5_Rat (Q9Z2J5) | 44 | Not cleaved | Not cleaved | Not cleaved | Not cleaved | Not cleaved | Arg40-Ser41 |
| VAMP5_human (O95183) | 45 | Not cleaved | Not cleaved | Not cleaved | Not cleaved | Not cleaved | Arg40-Ser41 |
| YKT6_Rat (Q5EGY4) | 46 | Not cleaved | Not cleaved | Not cleaved | Not cleaved | Not cleaved | Lys173-Ser174 |
| YKT6_human (O15498) | 47 | Not cleaved | Not cleaved | Not cleaved | Not cleaved | Not cleaved | Lys173-Ser174 |

In one embodiment, the VAMP is selected from VAMP1, VAMP2, VAMP3, VAMP4, VAMP5, and/or YKT6.

In one embodiment, the VAMP is selected from VAMP1, VAMP2 and/or VAMP3.

In one embodiment, the VAMP is selected from VAMP4, VAMP5 and/or YKT6.

In a preferred embodiment, the VAMP is a human VAMP, more preferably, a human VAMP1, VAMP2, VAMP3, VAMP4, VAMP5, and/or YKT6.

In one embodiment, the VAMP is selected from a human VAMP1, VAMP2 and/or VAMP3.

In one embodiment, the VAMP is selected from a human VAMP4, VAMP5 and/or YKT6.

In one embodiment of the antigenic polypeptide of the invention, the VAMP epitope is a BoNT/F cleaved VAMP epitope wherein the at least 8 amino acid residues are immediately C-terminal to a BoNT/F cleavage site in the VAMP.

Examples of BoNT/F VAMP epitopes, more particularly BoNT/F VAMP1, VAMP2 and/or VAMP3 epitopes, include:

```
                                     (SEQ ID NO: 15)
        KLSELDDRADALQ (SEQ ID NO: 16)
        QKLSELDDRADALQ (SEQ ID NO: 17)
        KLSELDDRAD (SEQ ID NO: 18)
        KLSELDDRADALQAGAS (SEQ ID NO: 31)
        DQKLSELDDRADALQ.
```

In one embodiment, a BoNT/F VAMP epitope, in particular a BoNT/F VAMP1, VAMP2 and/or VAMP3 epitope, comprises or consists of an amino acid sequence which is at least 90%, 91%, 92%, 93%, 94%, 95%, 96%, 97%, 98%, 99%, or is 100% identical to a sequence selected from: SEQ ID NO: 15 to SEQ ID NO: 18, and SEQ ID NO: 31. In a preferred embodiment, a BoNT/F VAMP epitope comprises or consists of an amino acid sequence which is at least 90%, 91%, 92%, 93%, 94%, 95%, 96%, 97%, 98%, 99%, or is 100% identical to KLSELDDRADALQ (SEQ ID NO: 15). In a more preferred embodiment, a BoNT/F VAMP epitope comprises or consists of KLSELDDRADALQ (SEQ ID NO: 15).

In one embodiment of the antigenic polypeptide of the invention, the VAMP epitope is a BoNT/D VAMP epitope wherein the at least 8 amino acid residues are immediately C-terminal to a BoNT/D cleavage site in the VAMP.

Examples of BoNT/D VAMP epitopes, more particularly BoNT/D VAMP1, VAMP2 and/or VAMP3 epitopes, include:

```
                                     (SEQ ID NO: 15)
        KLSELDDRADALQ (SEQ ID NO: 19)
        LSELDDRADALQ (SEQ ID NO: 20)
        LSELDDRADA (SEQ ID NO: 21)
        LSELDDRADALQAGAS.
```

In one embodiment, a BoNT/D VAMP epitope, in particular a BoNT/D VAMP1, VAMP2 and/or VAMP3 epitope, comprises or consists of an amino acid sequence which is at least 90%, 91%, 92%, 93%, 94%, 95%, 96%, 97%, 98%, 99%, or is 100% identical to a sequence selected from: SEQ ID NO: 15, and SEQ ID NO: 19 to SEQ ID NO: 21. In a preferred embodiment, a BoNT/D VAMP epitope comprises or consists of an amino acid sequence which is at least 90%, 91%, 92%, 93%, 94%, 95%, 96%, 97%, 98%, 99%, or is 100% identical to KLSELDDRADALQ (SEQ ID NO:15). In a more preferred embodiment, a BoNT/D VAMP epitope comprises or consists of KLSELDDRADALQ (SEQ ID NO: 15).

In one embodiment of the antigenic polypeptide of the invention, the VAMP epitope is a BoNT/F5 or BoNT/FA cleaved VAMP epitope wherein the at least 8 amino acid residues are immediately C-terminal to a BoNT/F5 or BoNT/FA cleavage site in the VAMP.

Examples of BoNT/F5 or BoNT/FA VAMP epitopes, more particularly BoNT/F5 or BoNT/FA VAMP1, VAMP2 and/or VAMP3 epitopes, include:

```
                                     (SEQ ID NO: 32)
        ERDQKLSELDDRA (SEQ ID NO: 33)
        LERDQKLSELDDRA (SEQ ID NO: 34)
        VLERDQKLSELDDRA.
```

In one embodiment, a BoNT/F5 or BoNT/FA VAMP epitope, in particular a BoNT/F5 or BoNT/FA VAMP1, VAMP2 and/or VAMP3 epitope, comprises or consists of an amino acid sequence which is at least 90%, 91%, 92%, 93%, 94%, 95%, 96%, 97%, 98%, 99%, or is 100% identical to a sequence selected from: SEQ ID NO: 32 to SEQ ID NO: 34. In a preferred embodiment, a BoNT/F5 or BoNT/FA VAMP epitope comprises or consists of an amino acid sequence which is at least 90%, 91%, 92%, 93%, 94%, 95%, 96%, 97%, 98%, 99%, or is 100% identical to ERDQKLSELDDRA (SEQ ID NO: 32). In a more preferred embodiment, a BoNT/F5 or BoNT/FA VAMP epitope comprises or consists of ERDQKLSELDDRA (SEQ ID NO: 32).

In one embodiment of the antigenic polypeptide of the invention, the VAMP epitope is a BoNT/B or TeNT VAMP epitope wherein the at least 8 amino acid residues are immediately C-terminal to a BoNT/B or TeNT cleavage site in the VAMP.

Examples of BoNT/B or TeNT VAMP epitopes, more particularly BoNT/B or TeNT VAMP1, VAMP2 and/or VAMP3 epitopes, include:

```
                                     (SEQ ID NO: 22)
        FETSAAKLKRKYW (SEQ ID NO: 23)
        FESSAAKLKRKYW (SEQ ID NO: 24)
        QFETSAAKLKRKYW (SEQ ID NO: 25)
        FETSAAKLKR (SEQ ID NO: 26)
        FETSAAKLKRKYWWKN
```

-continued

ETSAAKLKRKYWWK (SEQ ID NO: 48)

FETSAAKLKRKYWWK (SEQ ID NO: 49)

QFESSAAKLKRKYW (SEQ ID NO: 50)

FESSAAKLKR (SEQ ID NO: 51)

FESSAAKLKRKYWWK. (SEQ ID NO: 52)

In one embodiment, a BoNT/B or TeNT VAMP epitope, in particular a BoNT/B or TeNT VAMP1, VAMP2 and/or VAMP3 epitope, comprises or consists of an amino acid sequence which is at least 90%, 91%, 92%, 93%, 94%, 95%, 96%, 97%, 98%, 99%, or is 100% identical to a sequence selected from: SEQ ID NO: 22 to SEQ ID NO: 26, and SEQ ID NO: 48 to SEQ ID NO: 52. In a preferred embodiment, a BoNT/B or TeNT VAMP epitope comprises or consists of an amino acid sequence which is at least 90%, 91%, 92%, 93%, 94%, 95%, 96%, 97%, 98%, 99%, or is 100% identical to FETSAAKLKRKYW (SEQ ID NO: 22) or FETSAAKLKRKYWWK (SEQ ID NO: 49). In a more preferred embodiment, a BoNT/B or TeNT VAMP epitope comprises or consists of FETSAAKLKRKYW (SEQ ID NO: 22) or FETSAAKLKRKYWWK (SEQ ID NO: 49).

Surprisingly, antibodies binding the latter epitope allow not only the detection of BoNT/B VAMP cleavage, but also of BoNT/F VAMP cleavage.

In one embodiment of the antigenic polypeptide of the invention, the VAMP epitope is a BoNT/G VAMP epitope wherein the at least 8 amino acid residues are immediately C-terminal to a BoNT/G cleavage site in the VAMP.

Examples of BoNT/G VAMP epitopes, more particularly BoNT/G, VAMP1, VAMP2 and/or VAMP3 epitopes, include:

AKLKRKYWWKN (SEQ ID NO: 27)

AAKLKRKYWWKN (SEQ ID NO: 28)

AKLKRKYWWKNCKM (SEQ ID NO: 29)

AKLKRKYWWKNLKM. (SEQ ID NO: 30)

In one embodiment, a BoNT/G VAMP epitope, in particular a BoNT/G VAMP1, VAMP2 and/or VAMP3 epitope, comprises or consists of an amino acid sequence which is at least 90%, 91%, 92%, 93%, 94%, 95%, 96%, 97%, 98%, 99%, or is 100% identical to a sequence selected from: SEQ ID NO: 27 to SEQ ID NO: 30. In a preferred embodiment, a BoNT/G VAMP epitope comprises or consists of an amino acid sequence which is at least 90%, 91%, 92%, 93%, 94%, 95%, 96%, 97%, 98%, 99%, or is 100% identical to AKLKRKYWWKN (SEQ ID NO: 27). In a more preferred embodiment, a BoNT/G VAMP epitope comprises or consists of AKLKRKYWWKN (SEQ ID NO: 27).

In one embodiment of the antigenic polypeptide of the invention, the VAMP epitope is a BoNT/X VAMP epitope wherein the at least 8 amino acid residues are immediately C-terminal to a BoNT/X cleavage site in the VAMP.

Examples of BoNT/X VAMP epitopes, more particularly BoNT/X VAMP1, VAMP2 and/or VAMP3 epitopes, include:

ADALQAGASQF (SEQ ID NO: 53)

ADALQAGASQ (SEQ ID NO: 54)

RADALQAGASQF (SEQ ID NO: 55)

ADALQAGASQFE (SEQ ID NO: 56)

ADALQAGASVF (SEQ ID NO: 57)

ADALQAGASV (SEQ ID NO: 58)

ADALQAGASVFE (SEQ ID NO: 59)

RADALQAGASVF (SEQ ID NO: 60)

RADALQAGAS. (SEQ ID NO: 61)

In one embodiment, a BoNT/X VAMP epitope, in particular a BoNT/X VAMP1, VAMP2 and/or VAMP3 epitope, comprises or consists of an amino acid sequence which is at least 90%, 91%, 92%, 93%, 94%, 95%, 96%, 97%, 98%, 99%, or is 100% identical to a sequence selected from: SEQ ID NO: 53 to SEQ ID NO: 61. In a preferred embodiment, a BoNT/X VAMP epitope comprises or consists of an amino acid sequence which is at least 90%, 91%, 92%, 93%, 94%, 95%, 96%, 97%, 98%, 99%, or is 100% identical to ADALQAGASQF (SEQ ID NO: 53). In a more preferred embodiment, a BoNT/X VAMP epitope comprises or consists of ADALQAGASQF (SEQ ID NO: 53).

Other examples of BoNT/X VAMP epitopes, and more particularly BoNT/X VAMP4 epitopes, include:

SESLSDNATAF (SEQ ID NO: 62)

SESLSDNATA (SEQ ID NO: 63)

KSESLSDNATAF (SEQ ID NO: 64)

SESLSDNATAFS. (SEQ ID NO: 65)

In one embodiment, a BoNT/X VAMP epitope, in particular a BoNT/X VAMP4 epitope, comprises or consists of an amino acid sequence which is at least 90%, 91%, 92%, 93%, 94%, 95%, 96%, 97%, 98%, 99%, or is 100% identical to a sequence selected from: SEQ ID NO: 62 to SEQ ID NO: 65. In a preferred embodiment, a BoNT/X VAMP epitope comprises or consists of an amino acid sequence which is at least 90%, 91%, 92%, 93%, 94%, 95%, 96%, 97%, 98%, 99%, or is 100% identical to SESLSDNATAF (SEQ ID NO: 62). In a more preferred embodiment, a BoNT/X VAMP epitope comprises or consists of SESLSDNATAF (SEQ ID NO: 62).

Other examples of BoNT/X VAMP epitopes, and more particularly BoNT/X VAMP5 epitopes, include:

| | |
|---|---|
| SDQLLDMSSTF | (SEQ ID NO: 66) |
| SDQLLDMSST | (SEQ ID NO: 67) |
| RSDQLLDMSSTF | (SEQ ID NO: 68) |
| SDQLLDMSSTFN | (SEQ ID NO: 69) |
| SDQLLDMSSAF | (SEQ ID NO: 70) |
| SDQLLDMSSA | (SEQ ID NO: 71) |
| RSDQLLDMSSAF | (SEQ ID NO: 72) |
| SDQLLDMSSAFS | (SEQ ID NO: 73) |
| RSDQLLDMSS. | (SEQ ID NO: 74) |

In one embodiment, a BoNT/X VAMP epitope, in particular a BoNT/X VAMP5 epitope, comprises or consists of an amino acid sequence which is at least 90%, 91%, 92%, 93%, 94%, 95%, 96%, 97%, 98%, 99%, or is 100% identical to a sequence selected from: SEQ ID NO: 66 to SEQ ID NO: 74. In a preferred embodiment, a BoNT/X VAMP epitope comprises or consists of an amino acid sequence which is at least 90%, 91%, 92%, 93%, 94%, 95%, 96%, 97%, 98%, 99%, or is 100% identical to SDQLLDMSSTF (SEQ ID NO: 66). In a more preferred embodiment, a BoNT/X VAMP epitope comprises or consists of SDQLLDMSSTF (SEQ ID NO: 66).

Other examples of BoNT/X VAMP epitopes, and more particularly BoNT/X YKT6 epitopes, include:

| | |
|---|---|
| SEVLGTQSKAF | (SEQ ID NO: 75) |
| SEVLGTQSKA | (SEQ ID NO: 76) |
| KSEVLGTQSKAF | (SEQ ID NO: 77) |
| SEVLGTQSKAFY. | (SEQ ID NO: 78) |

In one embodiment, a BoNT/X VAMP epitope, in particular a BoNT/X YKT6 epitope, comprises or consists of an amino acid sequence which is at least 90%, 91%, 92%, 93%, 94%, 95%, 96%, 97%, 98%, 99%, or is 100% identical to a sequence selected from: SEQ ID NO: 75 to SEQ ID NO: 78. In a preferred embodiment, a BoNT/X VAMP epitope comprises or consists of an amino acid sequence which is at least 90%, 91%, 92%, 93%, 94%, 95%, 96%, 97%, 98%, 99%, or is 100% identical to SEVLGTQSKAF (SEQ ID NO: 75). In a more preferred embodiment, a BoNT/X VAMP epitope comprises or consists of SEVLGTQSKAF (SEQ ID NO: 75).

Herein, the "percent sequence identity" between two or more nucleic acid or amino acid sequences is a function of the number of identical nucleotides or amino acids at identical positions shared by the aligned sequences. Thus, % identity may be calculated as the number of identical nucleotides or amino acids at each position in an alignment divided by the total number of nucleotides or amino acids in the aligned sequence, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, which will be familiar to a skilled person, for example a global alignment mathematical algorithm (such as described by Needleman and Wunsch, J. Mol. Biol. 48(3), 443-453, 1972).

In another aspect, the invention relates to a polypeptide comprising an antigenic polypeptide according to the invention, wherein the polypeptide does not comprise a region of greater than 17, 16, 15, 14, 13, 12, 11, 10, preferably 16, more preferably 15, consecutive amino acids having 100% sequence identity to a naturally-occurring VAMP amino acid sequence. The skilled person in the art would readily understand that such polypeptide is also antigenic.

In a preferred embodiment, the polypeptide comprises a covalent linker, preferably in its N-terminus and/or in C-terminus. Examples of covalent linkers that are suitable according to the invention are provided below.

In another aspect, the invention provides an antigenic protein comprising a polypeptide according to the invention covalently linked to a carrier.

Preferably, the carrier is a non-immunogenic or weakly immunogenic protein. Examples of suitable carriers include keyhole limpet hemacyanin (KLH), ovalbumin (OVA), thyroglobulin (THY), bovine serum albumin (BSA), soybean trypsin inhibitor (STI) or a multiple attachment peptide (MAP).

In one embodiment, the antigenic protein comprises a covalent linker between the polypeptide of the invention (which may already comprise the linker, as indicated above) and the carrier. Said linker can be one or more amino acids, natural or unnatural, which, as well-known in the art, can form covalent bonds with other amino acids (of the polypeptide and/or carrier) due to the presence of reactive groups present in their N-terminus, C-terminus and/or side chains. Notably, an amino acid having a primary amine group (—NH2) in N-terminus and/or side chain (such as lysine) can react with an amino acid having a carboxyl (—COOH) group in C-terminus and/or side chain (such as aspartic acid or glutamic acid) to form a covalent bond; an amino acid having a sulfhydryl (—SH) group in side chain (such as cysteine or selenocysteine) can react with an amino acid having a sulfhydryl (—SH) group in side chain (such as cysteine or selenocysteine) to form a covalent bond. For example, the covalent linker can be a cysteine added in C-terminus or N-terminus of the polypeptide of the invention, said cysteine forming a disulphide bridge with another cysteine added or present in the carrier. The covalent linker may alternatively, or in addition, be in the form of several amino acids forming a spacer, for example the linker can be a peptide comprising non-charged amino acids with small side-chain R groups, such as, e.g., glycine, alanine, valine, leucine or serine. Examples of suitable spacers of the invention include G-spacers such as GGG, GGGG and GGGGS or A-spacers such as AAA, AAAA and AAAAV. In one embodiment, the linker consists of about 1 to about 30 amino acid residues, preferably about 2 to about 25 amino acid residues, more preferably about 3 to about 20 amino acid residues, for example, 4, 5, 6, 7, 8, 9, 10, 11, 12, 13, 14 or 15 amino acid residues.

In another aspect, the invention provides the use of an antigenic polypeptide or protein according to the invention to generate antibodies against a C-terminal VAMP cleavage product. In one embodiment, the epitope of the invention is used to generate a polyclonal antibody against a C-terminal VAMP cleavage product. In another embodiment, the epitope of the invention is used to generate a monoclonal antibody against a C-terminal VAMP cleavage product.

Methods for generating antibodies are well known in the art, see eg. Greenfield, Edward A., ed. *Antibodies: a laboratory manual*. Cold Spring Harbor Laboratory Press, 2014; Leenaars, Marlies, and Coenraad F M Hendriksen. "Critical steps in the production of polyclonal and monoclonal antibodies: evaluation and recommendations." Ilar Journal 46.3 (2005): 269-279.

Polyclonal antibodies that bind to a VAMP epitope as described herein can be produced by injecting an animal, e.g. a mammal such as a rabbit, a goat, a mouse, a hamster or a monkey, or an egg, such as a chicken egg, with an antigenic polypeptide or protein of the invention. Polyclonal antibodies for a VAMP epitope as disclosed herein can be isolated from the animal (e.g. from the blood) or egg and further purified by well-known techniques, such as protein affinity chromatography to obtain the IgG fraction, or by affinity purification against the VAMP epitope used for producing the antibodies. Several contract research organisations provide custom antibody generation services, for example the company Eurogentec provides a "Speedy 28-day programme" in which they immunise day 0, and then have 3 booster injections day 7, 10 and 18. Medium bleed day 21 and final bleed day 28. This is one example of the general technique of polyclonal antibody production which is well known in the art.

Monoclonal antibodies that bind to a VAMP epitope as described herein can be produced using a hybridoma method. See e.g., Chapter 7, Greenfield, Edward A., ed. *Antibodies: a laboratory manual*. Cold Spring Harbor Laboratory Press, 2014. Briefly, a host animal, e.g. a mammal such as a rabbit, a goat, a mouse, a hamster or a monkey, is exposed to one or more injections of an antigenic polypeptide or protein of the invention to elicit lymphocytes that produce or are capable of producing antibodies that will specifically bind to a cleaved VAMP. The antibody titer in the immunized animal can be monitored over time by standard techniques, such as with an ELISA (enzyme linked immunosorbent assay). Alternatively, the lymphocytes can be immunized in vitro using a suitable cell culture line. At an appropriate time after immunization, e.g., when the antibody titers are highest, antibody-producing cells are isolated from the animal. Generally, either peripheral blood lymphocytes are used, if cells of human origin are desired, or spleen cells or lymph node cells are used, if non-human mammalian sources are desired. The isolated antibody-producing cells are fused with an immortal cell line using a suitable fusing agent, such as polyethylene glycol, to form a hybridoma cell. Immortalized cell lines are usually transformed mammalian cells, particularly myeloma cells of rodent, bovine and human origin. Typically, a murine myeloma cell line is fused with splenocytes harvested from an appropriately immunized mouse to produce the hybridoma. Preferred immortal cell lines are mouse myeloma cell lines that are sensitive to culture medium containing hypoxanthine, aminopterin and thymidine (HAT). Any of a number of myeloma cell lines can be used as a fusion partner according to standard techniques, e.g., the P3-NS1/1-Ag4-1, P3-x63-Ag8.653 or Sp2/O—Ag14 myeloma lines. Hybridoma cells resulting from the fusion are then selected using HAT medium, which kills unfused and unproductively fused myeloma cells (unfused splenocytes die after several days in culture because they are not transformed). The culture medium in which the hybridoma cells are grown can then be assayed for the presence of monoclonal antibodies that bind a VAMP epitope as described herein. For example, hybridoma supernatants can be screened using a cleaved VAMP positive media in an immunoprecipitation assay, in vitro binding assay, such as, e.g., a radioimmunoassay (RIA) or an enzyme-linked immunoabsorbent assay (ELISA), or in a cell-based activity assay. The binding affinity of a monoclonal antibody can also be determined, e.g., by Scatchard analysis. See, e.g., Peter J. Munson and David Rodbard, Ligand: A Versatile Computerized Approach For Characterization of Ligand-Binding Systems, 107(1) Anal. Biochem. 220-239 (1980). After the desired hybridoma cells are identified, limiting dilution procedures are used to isolate clones originating from a single cell until a clonal cell line expressing the desired monoclonal antibody is obtained. Alternatively, monoclonal antibodies that bind a VAMP epitope as described herein can be produced by screening a recombinant combinatorial immunoglobulin library, such as, e.g., an antibody phage display library, with an antigenic polypeptide, protein or peptide of the invention. Kits for generating and screening phage display libraries are commercially available, such as, e.g., the Recombinant Phage Antibody System (Amersham GE Healthcare, Piscataway, N.J.); and the SurfZAP™ Phage Display Kit (Stratagene, La Jolla, Calif.). Additionally, examples of methods and reagents useful in generating and screening antibody display library can be found in, for example, Ladner et al. U.S. Pat. No. 5,223,409; Borrebaeck et al. U.S. Pat. No. 5,712,089; Griffiths et al. U.S. Pat. No. 5,885,793; Griffiths et al. U.S. Pat. No. 5,962,255; McCafferty et al. U.S. Pat. No. 5,969,108; Griffiths et al. U.S. Pat. No. 6,010,884; Jespers et al. U.S. Pat. No. 6,017,732; Borrebaeck et al. U.S. Pat. No. 6,027,930; Johnson et al. U.S. Pat. No. 6,140,471; McCafferty et al. U.S. Pat. No. 6,172,197, each of which is hereby incorporated by reference in its entirety.

In another aspect, the invention provides an antibody that binds to an antigenic polypeptide or protein of the invention.

In one embodiment, the antibody is a polyclonal antibody.

In one embodiment, the antibody is a monoclonal antibody.

Binding affinity between the antibody and the antigenic polypeptide or protein can be assessed by determining the equilibrium dissociation constant ($K_D$) which measures the rate at which new antibody-antigen complexes formed equals the rate at which antibody-antigen complexes dissociate at equilibrium. The equilibrium dissociation constant is expressed in M, and is defined by the Kd/Ka ratio at equilibrium, where Ka is the antibody's association rate constant and Kd is the antibody's dissociation rate constant. $K_D=[Ab]\times[Ag]/[Ab+Ag]$, where [Ab] is the molar concentration of the antibody, [Ag] is the molar concentration of the antigen, and [Ab+Ag] is the of molar concentration of the antibody-antigen complex, where all concentrations are of such components when the system is at equilibrium. The smaller the equilibrium dissociation constant, the more tightly bound the antibody is to its antigen, or the higher the binding affinity between antibody and antigen.

In a one embodiment, the $K_D$ between the antibody of the invention and the antigenic polypeptide or protein epitope is lower than $10^{-6}$ M. In a preferred embodiment, the $K_D$ between the antibody of the invention and the antigenic polypeptide or protein is lower than $10^{-7}$ M. In a more preferred embodiment, the $K_D$ between the antibody of the invention and the antigenic polypeptide or protein is lower than $10^{-8}$ M. In a more preferred embodiment, the $K_D$ between the antibody of the invention and the antigenic polypeptide or protein is lower than $10^{-9}$ M. In a more preferred embodiment, the $K_D$ between the antibody of the invention and the antigenic polypeptide or protein is lower than $10^{-10}$ M. In a more preferred embodiment, the $K_D$ between the antibody of the invention and the antigenic polypeptide or protein is lower than $10^{-11}$ M. In a more preferred embodiment, the $K_D$ between the antibody of the invention and the antigenic polypeptide or protein is lower than $10^{-12}$ M.

In another aspect, the invention provides the use of an antibody according to the invention in a gain of signal cellular assay for VAMP cleavage by a VAMP cleaving clostridial neurotoxin.

In one embodiment, the use is an in vitro or an ex vivo use.

In another aspect, the invention provides a method for determining cleavage of VAMP by a VAMP cleaving clostridial neurotoxin in a cell, comprising:
a) contacting the cell with the clostridial neurotoxin under conditions suitable for clostridial neurotoxin activity;
b) contacting the cytoplasmic content of said cell with a first detection antibody against the C-terminal VAMP cleavage product following cleavage of a VAMP by the VAMP cleaving clostridial neurotoxin under conditions suitable for the binding of the first detection antibody to the C-terminal VAMP cleavage product, wherein said first detection antibody is an antibody according to the invention; and
c) detecting by a suitable means the binding of said first detection antibody to the C-terminal VAMP cleavage product.

In one embodiment, the method according to the invention, further comprises d) quantifying by a suitable means the amount of the C-terminal VAMP cleavage product bound to said first detection antibody.

In one embodiment of the method of the invention, step b) comprises contacting the cytoplasmic content of said cell with a second detection antibody against full-length VAMP under conditions suitable for the binding of said second detection antibody to full-length VAMP; step c) comprises detecting by a suitable means the binding of the second detection antibody to full-length VAMP, and step d) comprises quantifying by a suitable means the amount of full-length VAMP bound to said second detection antibody.

In one embodiment, the method is an in vitro or an ex vivo method.

It will be clear to the person skilled in the art that an increase in the amount of C-terminal VAMP cleavage product bound to the first antibody and/or a decrease in the amount of full-length VAMP bound to the second detection antibody are indicative of an increase in VAMP cleavage by the VAMP cleaving clostridial neurotoxin.

In one embodiment, the second detection antibody is the same as the first detection antibody and binds to the C-terminal VAMP cleavage product and to full-length VAMP.

In an alternative embodiment, the second detection antibody is different from said first detection antibody, and binds to full-length VAMP but not to the C-terminal VAMP cleavage product. Suitably, the second detection antibody binds to a VAMP epitope which is N-terminal to a clostridial neurotoxin cleavage site. Examples of suitable antibodies include commercially available antibodies such as ab3347 (Abcam) or ab181869 (Abcam).

In a particular embodiment, the method for determining cleavage of VAMP by a VAMP cleaving clostridial neurotoxin in a cell, comprises:
a) contacting the cell with the clostridial neurotoxin under conditions suitable for clostridial neurotoxin activity;
b) contacting the cytoplasmic content of said cell with
a first detection antibody against the C-terminal VAMP cleavage product following cleavage of a VAMP by the VAMP cleaving clostridial neurotoxin under conditions suitable for the binding of the first detection antibody to the C-terminal VAMP cleavage product, wherein said first detection antibody is an antibody according to the invention which binds to the C-terminal VAMP cleavage product and to full-length VAMP; and with
a second detection antibody which binds to full-length VAMP but not to the C-terminal VAMP cleavage product;
c) detecting by a suitable means
the binding of the first antibody to the C-terminal VAMP cleavage product and to full-length VAMP; and
the binding of the second detection antibody to the full-length VAMP; and
d) quantifying by a suitable means:
the combined amount of C-terminal VAMP cleavage product and full-length VAMP bound to the first detection antibody; and
the amount of full-length VAMP bound to the second detection antibody.

It will be clear to the person skilled in the art that a decrease in the amount of full-length VAMP bound to the second detection antibody and no change in the combined amount of full-length and C-terminal VAMP cleavage product bound to the first detection antibody is indicative of VAMP cleavage by the VAMP cleaving clostridial neurotoxin.

In another particular embodiment, the method for determining cleavage of VAMP by a VAMP cleaving clostridial neurotoxin in a cell, comprises:
a) contacting the cell with the clostridial neurotoxin under conditions suitable for clostridial neurotoxin activity;
b) contacting the cytoplasmic content of said cell with a first detection antibody against the C-terminal VAMP cleavage product following cleavage of a VAMP by the VAMP cleaving clostridial neurotoxin under conditions suitable for the binding of the first detection antibody to the C-terminal VAMP cleavage product, wherein said first detection antibody is an antibody according to the invention which binds to the C-terminal VAMP cleavage product and to full-length VAMP;
c) detecting by a suitable means
the binding of the first antibody to the C-terminal VAMP cleavage product; and
the binding of the first detection antibody to the full-length VAMP;
wherein the signal generated from binding of the first detection antibody to the C-terminal VAMP cleavage product can be distinguished from the signal generated from binding of the first detection antibody to full-length VAMP; and
d) quantifying by a suitable means:
the amount of C-terminal VAMP cleavage product bound to the first detection antibody; and
the amount of full-length VAMP bound to the first detection antibody.

It will be clear to the person skilled in the art that an increase in the amount of C-terminal VAMP cleavage product bound to the first antibody and a decrease in the amount of full-length VAMP bound to the first detection antibody are indicative of an increase in VAMP cleavage by the VAMP cleaving clostridial neurotoxin.

In another aspect, the invention provides a method for determining immunoresistance to a VAMP cleaving clostridial neurotoxin in a subject, comprising:
a) adding a VAMP cleaving clostridial neurotoxin to a test sample obtained from the subject;
b) contacting a cell with the test sample of step a) under conditions suitable for clostridial neurotoxin activity;
c) contacting the cytoplasmic content of said cell with a first detection antibody against the C-terminal VAMP cleavage product following cleavage of a VAMP by the VAMP cleaving clostridial neurotoxin under conditions suitable for the binding of the first detection antibody to the C-terminal VAMP cleavage product, wherein said first detection antibody is an antibody according to the invention;
d) detecting by a suitable means the binding of the first detection antibody to the C-terminal VAMP cleavage product;
e) quantifying the amount of the C-terminal VAMP cleavage product bound to the first detection antibody;
f) repeating steps a) to e) with a negative control sample instead of a test sample; and
g) comparing the amount of the C-terminal VAMP cleavage product bound to said first detection antibody in steps (e) and (f), wherein detection of a lower amount of the C-terminal VAMP cleavage product bound to said first detection antibody in step (e) relative to the amount of the C-terminal VAMP cleavage product bound to said first detection antibody in step (f) is indicative of the presence of neutralizing antibodies against the VAMP cleaving clostridial neurotoxin.

In one embodiment, step f) further comprises repeating steps a) to e) with a positive control sample.

As used herein, the term "neutralizing antibodies against a VAMP cleaving clostridial neurotoxin" means any antibody that will, under physiological conditions, bind to a region of a VAMP cleaving clostridial neurotoxin in such a manner as to reduce or prevent the VAMP cleaving clostridial neurotoxin from exerting its therapeutic effect in a subject.

In one embodiment, the subject is a mammal. In a preferred embodiment, the subject is a human being.

In one embodiment, the sample is selected from blood, plasma, serum and lymph fluid obtained from the subject.

A test sample can be obtained from a subject prior to exposure to a VAMP cleaving clostridial neurotoxin, after a single treatment with a VAMP cleaving clostridial neurotoxin or after multiple treatments with a VAMP cleaving clostridial neurotoxin. In a particular embodiment, the test sample is from a subject which is resistant to treatment with a VAMP cleaving clostridial neurotoxin.

As used herein, the term "control sample" means any sample in which the presence or absence of the test sample is known and includes both negative and positive control samples. With respect to neutralizing antibodies against VAMP cleaving clostridial neurotoxin, a negative control sample can be obtained from an individual who had never been exposed to the VAMP cleaving clostridial neurotoxin and may include, without limitation, a sample from the same individual supplying the test sample, but taken before undergoing a treatment with a VAMP cleaving clostridial neurotoxin; a sample taken from a different individual never been exposed to a VAMP cleaving clostridial neurotoxin; a pooled sample taken from a plurality of different individuals never been exposed to a VAMP cleaving clostridial neurotoxin.

With respect to neutralizing antibodies against a VAMP cleaving clostridial neurotoxin, a positive control sample can be obtained from an individual manifesting immunoresistance to the VAMP cleaving clostridial neurotoxin and includes, without limitation, individual testing positive in a patient-based testing assays; individual testing positive in an in vivo bioassay; and individual showing hyperimmunity, e.g., a subject vaccinated against a VAMP cleaving clostridial neurotoxin.

In one embodiment, the method is an in vitro or an ex vivo method.

In one embodiment of the method for determining immunoresistance, step c) comprises contacting the cytoplasmic content of said cell with a second detection antibody against full-length VAMP under conditions suitable for the binding of said second detection antibody to full-length VAMP; step d) comprises detecting by a suitable means the binding of the second detection antibody to full-length VAMP, and step e) comprises quantifying the amount of full-length VAMP bound to said second detection antibody.

In one embodiment, the second detection antibody is the same as the first detection antibody and binds to the C-terminal VAMP cleavage product and to full-length VAMP.

In an alternative embodiment, the second detection antibody is different from said first detection antibody, and binds to full-length VAMP but not to the C-terminal VAMP cleavage product. Suitably, the second detection antibody binds to a VAMP epitope which is N-terminal to a clostridial neurotoxin cleavage site. Examples of suitable antibodies include commercially available antibodies such as ab3347 (Abcam) or ab181869 (Abcam).

In a particular embodiment, the method for determining immunoresistance to a VAMP cleaving clostridial neurotoxin in a subject, comprises:
a) adding a VAMP cleaving clostridial neurotoxin to a test sample obtained from the subject;
b) contacting a cell with the test sample of step a) under conditions suitable for clostridial neurotoxin activity;
c) contacting the cytoplasmic content of said cell with
   a first detection antibody against the C-terminal VAMP cleavage product following cleavage of a VAMP by the VAMP cleaving clostridial neurotoxin under conditions suitable for the binding of the first detection antibody to the C-terminal VAMP cleavage product, wherein said first detection antibody is an antibody according to the invention which binds to the C-terminal VAMP cleavage product and to full-length VAMP; and with
   a second detection antibody which binds to full-length VAMP but not to the C-terminal VAMP cleavage product;
d) detecting by a suitable means
   the binding of the first antibody to the C-terminal VAMP cleavage product and to full-length VAMP; and
   the binding of the second detection antibody to the full-length VAMP;
e) quantifying
   the combined amount of C-terminal VAMP cleavage product and full-length VAMP bound to the first detection antibody; and
   the amount of full-length VAMP bound to the second detection antibody;
f) repeating steps a) to e) with a negative control sample instead of a test sample; and g) comparing the amount of the C-terminal VAMP cleavage product bound to said first detection antibody in steps (e) and (f), wherein detection of a lower combined amount of the C-terminal VAMP cleavage product and full-length VAMP bound to the first detection antibody and/or a higher amount of the full-length VAMP bound to the second detection antibody in step (e) relative to the corresponding amounts in step (f) is indicative of the presence of neutralizing antibodies against the VAMP cleaving clostridial neurotoxin.

In another particular embodiment, the method for determining immunoresistance to a VAMP cleaving clostridial neurotoxin in a subject, comprises:

a) adding a VAMP cleaving clostridial neurotoxin to a test sample obtained from the subject;
b) contacting a cell with the test sample of step a) under conditions suitable for clostridial neurotoxin activity;
c) contacting the cytoplasmic content of said cell with a first detection antibody against the C-terminal VAMP cleavage product following cleavage of a VAMP by the VAMP cleaving clostridial neurotoxin under conditions suitable for the binding of the first detection antibody to the C-terminal VAMP cleavage product, wherein said first detection antibody is an antibody according to the invention which binds to the C-terminal VAMP cleavage product and to full-length VAMP;
d) detecting by a suitable means
   the binding of the first antibody to the C-terminal VAMP cleavage product and to full-length VAMP; and
   the binding of the first detection antibody to the full-length VAMP;
   wherein the signal generated from binding of the first detection antibody to the C-terminal VAMP cleavage product can be distinguished from the signal generated from binding of the first detection antibody to full-length VAMP;
e) quantifying
   the amount of C-terminal VAMP cleavage product bound to the first detection antibody; and
   the amount of full-length VAMP bound to the first detection antibody;
f) repeating steps a) to e) with a negative control sample instead of a test sample; and
g) comparing the amount of the C-terminal VAMP cleavage product bound to said first detection antibody in steps (e) and (f), wherein detection of a lower amount of the C-terminal VAMP cleavage product bound to said first detection antibody and/or a higher amount of the full-length VAMP bound to the first detection antibody in step (e) relative to the corresponding amounts in step (f) is indicative of the presence of neutralizing antibodies against the VAMP cleaving clostridial neurotoxin.

Herein, a "VAMP cleaving clostridial neurotoxin" means a clostridial neurotoxin which binds to a receptor on a target cell, translocates a clostridial light chain (L) into the cytosol, which in turn proteolytically cleaves a VAMP thereby disrupting the secretion of molecules via vesicle transport by the cell.

Preferably, in the methods or use of the invention, the VAMP cleaving clostridial neurotoxin comprises a BoNT/B, BoNT/D, BoNT/F, BoNT/G, BoNT/X or TeNT light chain. Suitably, the BoNT/B, BoNT/D, BoNT/F, BoNT/G, BoNT/X or TeNT light chain comprises a sequence selected from:

amino acid residues 1 to 441 of SEQ ID NO: 2, or a polypeptide sequence having at least 70%, preferably at least 75%, 80%, 85%, 90%, 95% or 99% sequence identity thereto, amino acid residues 1 to 442 of SEQ ID NO: 4, or a polypeptide sequence having at least 70%, preferably at least 75%, 80%, 85%, 90%, 95% or 99% sequence identity thereto, amino acid residues 1 to 439 of SEQ ID NO: 6, or a polypeptide sequence having at least 70%, preferably at least 75%, 80%, 85%, 90%, 95% or 99% sequence identity thereto, amino acid residues 1 to 446 of SEQ ID NO: 7, or a polypeptide sequence having at least 70%, preferably at least 75%, 80%, 85%, 90%, 95% or 99% sequence identity thereto, amino acid residues 1 to 439 of SEQ ID NO: 41, or a polypeptide sequence having at least 70%, preferably at least 75%, 80%, 85%, 90%, 95% or 99% sequence identity thereto, and amino acid residues 1 to 456 of SEQ ID NO: 8, or a polypeptide sequence having at least 70%, preferably at least 75%, 80%, 85%, 90%, 95% or 99% sequence identity thereto.

It is understood that a BoNT/B, BoNT/D, BoNT/F, BoNT/G, BoNT/X or TeNT light chain as described herein has the ability to cleave a VAMP.

In one embodiment of methods or uses of the invention, the VAMP cleaving clostridial neurotoxin is selected from a BoNT/B, BoNT/D, BoNT/F, BoNT/G, BoNT/X and a TeNT. Suitably, the BoNT/B, BoNT/D, BoNT/F, BoNT/G, BoNT/X or TeNT comprises a sequence selected from:

SEQ ID NO: 2 or a polypeptide sequence having at least 70%, preferably at least 75%, 80%, 85%, 90%, 95% or 99% sequence identity thereto, SEQ ID NO: 4, or a polypeptide sequence having at least 70%, preferably at least 75%, 80%, 85%, 90%, 95% or 99% sequence identity thereto, SEQ ID NO: 6, or a polypeptide sequence having at least 70%, preferably at least 75%, 80%, 85%, 90%, 95% or 99% sequence identity thereto, SEQ ID NO: 7, or a polypeptide sequence having at least 70%, preferably at least 75%, 80%, 85%, 90%, 95% or 99% sequence identity thereto, SEQ ID NO: 41, or a polypeptide sequence having at least 70%, preferably at least 75%, 80%, 85%, 90%, 95% or 99% sequence identity thereto and SEQ ID NO: 8, or a polypeptide sequence having at least 70%, preferably at least 75%, 80%, 85%, 90%, 95% or 99% sequence identity thereto.

It is understood that a BoNT/B, BoNT/D, BoNT/F, BoNT/G, BoNT/X or TeNT clostridial neurotoxin as described herein has the ability to bind to a receptor on a target cell, translocate the clostridial light chain into the cytosol and cleave a VAMP.

In one embodiment, the VAMP cleaving clostridial neurotoxin is a mosaic neurotoxin. The term "mosaic neurotoxin" as used in this context refers to a naturally occurring clostridial neurotoxin that comprises at least one functional domain from another type of clostridial neurotoxins (e.g. a clostridial neurotoxin of a different serotype), the clostridial neurotoxin not usually comprising the at least one functional domain. Examples of naturally occurring VAMP cleaving mosaic neurotoxins are BoNT/DC and BoNT/FA. BoNT/DC comprises the L chain and $H_N$ domain of serotype D and the $H_C$ domain of serotype C Nakamura K, et al. "Characterization of the D/C mosaic neurotoxin produced by

*Clostridium botulinum* associated with bovine botulism in Japan." Vet. Microbiol. (2010): 140:147-154, whereas BoNT/FA consists of a BoNT/F5 light chain, a $H_N$ domain closely related to subtype F1 and a BoNT/A1 $H_C$ domain (Pellett, Sabine, et al. "Purification and Characterization of Botulinum Neurotoxin FA from a Genetically Modified *Clostridium botulinum* Strain." mSphere 1.1 (2016): e00100-15).

In one embodiment, the VAMP cleaving clostridial neurotoxin is a mosaic neurotoxin selected from BoNT/DC and BoNT/FA.

In one embodiment, the VAMP cleaving clostridial neurotoxin is a chimeric neurotoxin. The term "chimeric neurotoxin" as used herein means a neurotoxin comprising one or more domains originating from a first neurotoxin and one or more domains originating from a second neurotoxin. For example, a chimeric neurotoxin may comprise an $LH_N$ domain originating from a first neurotoxin and a $H_C$ domain originating from a second neurotoxin. Another example of a chimeric neurotoxin is a neurotoxin comprising an $LH_NH_{CN}$ domain originating from a first neurotoxin and a $H_{CC}$ domain originating from a second neurotoxin. Examples of chimeric neurotoxins are provided in GB1607901.4 (not yet published), herein incorporated by reference.

In one embodiment, the VAMP cleaving clostridial neurotoxin is a chimeric neurotoxin which comprises:
  a light chain (L) from a BoNT/B, BoNT/D, BoNT/F, BoNT/G, BoNT/X or TeNT,
  a $H_N$ domain from a BoNT/A, BoNT/B, BoNT/C, BoNT/D, BoNT/E, BoNT/F, BoNT/G, BoNT/X or TeNT,
  a $H_{CN}$ domain from a BoNT/A, BoNT/B, BoNT/C, BoNT/D, BoNT/E, BoNT/F, BoNT/G, BoNT/X or TeNT,
  a $H_{CC}$ domain from a BoNT/A, BoNT/B, BoNT/C, BoNT/D, BoNT/E, BoNT/F, BoNT/G, BoNT/X or TeNT, and wherein at least two of the domains are from different clostridial neurotoxins.

In one embodiment, the VAMP cleaving clostridial neurotoxin is a chimeric neurotoxin which comprises:
  a $LH_N$ domain from a first clostridial neurotoxin selected from BoNT/B, BoNT/D, BoNT/F, BoNT/G, BoNT/X or TeNT,
  a $H_{CN}H_{CC}$ domain from a second clostridial neurotoxin selected from BoNT/A, BoNT/B, BoNT/C, BoNT/D, BoNT/E, BoNT/F, BoNT/G, BoNT/X or TeNT wherein the first and second clostridial neurotoxins are different.

In one embodiment, the VAMP cleaving clostridial neurotoxin is a chimeric neurotoxin which comprises:
  a $LH_NH_{CN}$ domain from a first clostridial neurotoxin selected from BoNT/B, BoNT/D, BoNT/F, BoNT/G, BoNT/X or TeNT,
  a $H_{CC}$ domain from a second clostridial neurotoxin selected from BoNT/A, BoNT/B, BoNT/C, BoNT/D, BoNT/E, BoNT/F, BoNT/G, BoNT/X or TeNT wherein the first and second clostridial neurotoxins are different.

The VAMP cleaving clostridial neurotoxin can be a modified neurotoxin or a derivative thereof, including but not limited to those described below. A modified neurotoxin or derivative may contain one or more amino acids that has been modified as compared to the native (unmodified) form of the neurotoxin, or may contain one or more inserted amino acids that are not present in the native (unmodified) form of the toxin. By way of example, a modified clostridial neurotoxin may have modified amino acid sequences in one or more domains relative to the native (unmodified) clostridial neurotoxin sequence. Such modifications may modify functional aspects of the neurotoxin, for example biological activity or persistence.

A modified VAMP cleaving clostridial neurotoxin as described herein retains the ability to bind to a receptor on a target cell, to translocate the light chain into the cell cytoplasm and cleave a VAMP.

A modified VAMP cleaving clostridial neurotoxin may have one or more modifications in the amino acid sequence of the heavy chain (such as a modified $H_C$ domain), wherein said modified heavy chain binds to target nerve cells with a higher or lower affinity than the native (unmodified) neurotoxin. Such modifications in the $H_C$ domain can include modifying residues in the ganglioside binding site or in the protein receptor binding site of the $H_{CC}$ domain that alter binding to the ganglioside receptor and/or the protein receptor of the target nerve cell. Examples of such modified neurotoxins are described in WO 2006/027207 and WO 2006/114308, both of which are hereby incorporated by reference in their entirety. For example, the $H_{CC}$ domain from a BoNT/B neurotoxin comprises at least one amino acid residue substitution, addition or deletion which has the effect of increasing the binding affinity of the BoNT/B $H_{CC}$ domain for human Syt II as compared to the natural BoNT/B $H_{CC}$ sequence. Suitable amino acid residue substitution, addition or deletion in the BoNT/B $H_{CC}$ subdomain have been disclosed in WO2013/180799 and in PCT/US2016/024211 which is not yet published (both herein incorporated by reference). Suitable amino acid residue substitution, addition or deletion in the $H_{CC}$ subdomain include substitution mutations selected from the group consisting of: V1118M; Y1183M; E1191M; E1191I; E1191Q; E1191T; S1199Y; S1199F; S1199L; S1201V; E1191C, E1191V, E1191L, E1191Y, S1199W, S1199E, S1199H, W1178Y, W1178Q, W1178A, W1178S, Y1183C, Y1183P and combinations thereof.

In one embodiment, the VAMP cleaving clostridial neurotoxin is a retargeted neurotoxin. The term "retargeted neurotoxin" (also referred to as "targeted secretion inhibitors", "TSIs", "TVEMPs" or "TEMs") as used herein means a clostridial neurotoxin comprising a Targeting Moiety™ which binds to a non clostridial receptor. The TM can replace part or all of the $H_C$ or $H_{CC}$ domain of the clostridial neurotoxin heavy chain. Examples of retargeted neurotoxins are disclosed in WO96/33273, WO98/07864, WO00/10598, WO01/21213, WO01/53336; WO02/07759 WO2005/023309, WO2006/026780, WO2006/099590, WO2006/056093, WO2006/059105, WO2006/059113, WO2007/138339, WO2007/106115, WO2007/106799, WO2009/150469, WO2009/150470, WO2010/055358, WO2010/020811, WO2010/138379, WO2010/138395, WO2010/138382, WO2011/020052, WO2011/020056, WO2011/020114, WO2011/020117, WO2011/20119, WO2012/156743, WO2012/134900, WO2012/134897, WO2012/134904, WO2012/134902, WO2012/135343, WO2012/135448, WO2012/135304, WO2012/134902, WO2014/033441, WO2014/128497, WO2014/053651, WO2015/004464, all of which are herein incorporated by reference.

Examples of cells suitable for use in the methods or use according to the invention include a prokaryotic cell, eg. an *E. coli* cell, a yeast cell, an insect cell, an animal cell, a mammalian cell, a human cell, a mouse cell, a primate cell, and/or a neuronal cell. Preferably, the cell is a neuronal cell, in particular cells with a high sensitivity to BoNT, A cell with a high sensitivity to BoNT is a cell which is susceptible to BoNT intoxication. In some embodiments, a cell with a high sensitivity to BoNT is a cell which is susceptible to BoNT intoxication by, e.g., about 500 pM or less, about 400 pM or less, about 300 pM or less, about 200 pM or less, about 100 pM or less, about 90 pM or less, about 80 pM or less, about 70 pM or less, about 60 pM or less, about 50 pM or less, about 40 pM or less, about 30 pM or less, about 20 pM or less, about 10 pM or less, about 9 pM or less, about 8 pM or less, about 7 pM or less, about 6 pM or less, about 5 pM or less, about 4 pM or less, about 3 pM or less, about 2 pM or less, about 1 pM or less, about 0.9 pM or less, about 0.8 pM or less, about 0.7 pM or less, about 0.6 pM or less, about 0.5 pM or less, about 0.4 pM or less, about 0.3 pM or less, about 0.2 pM, about 0.1 pM or less, about 90 fM or less, about 80 fM or less, about 70 fM or less, about 60 fM or less, about 50 fM or less, about 40 fM or less, about 30 fM or less, about 20 fM or less, or about 10 fM or less.

Preferably, the cell has a high sensitivity (as defined above) to a VAMP cleaving BoNT.

In one embodiment, the cell is a primary neuronal cell with a high sensitivity to BoNT, e.g., cortical neurons, hippocampal neurons, and/or spinal cord neurons. For example, the cell is a rat cortical neuron.

In one embodiment, the cell is from a neuronal cell line with a high sensitivity to BoNT, e.g. BE(2)-M17, Kelly, LA1-55n, N1 E-115, N4TG3, N18, Neuro-2a, NG108-15, PC12, SH-SY5Y, SiMa, and/or SK-N-BE(2)-C.

In one embodiment, the cell is a neuronal cell derived from a stem cell, in particular from an induced pluripotent stem cell (iPS cell), eg. i-Cell® Neurons, i-Cell® DopaNeurons iCell Glutamatergic Neurons, iCell MotoNeurons (Cellular dynamics Inc) Cerebral Cortical Neurons, Neural Stem Cells (Axol Biosciences), Peri.4U neurons, CNS.4U neurons, Dopa.4UNeurons (Axiogenesis), MNP cells (Lonza), Cortical Neurons, Motor Neurons (iStem), and/or iPSC-Derived Neural Cells (MTI-GlobalStem).

In one embodiment, the cell can be modified by recombinant technology to express high levels of VAMP, such as VAMP1, VAMP2 VAMP3, VAMP4, VAMP5 and/or YKT6, more preferably VAMP1, VAMP2 and/or VAMP3.

In one embodiment in which the VAMP cleaving neurotoxin is a BoNT/B, a BoNT/DC or a BoNT/G, the cell expresses high levels of synaptotagmin I and/or synaptotagmin II (Syt I/Syt II). In one embodiment in which the VAMP cleaving neurotoxin is a BoNT/B, a BoNT/D-C or a BoNT/G, the cell is modified by recombinant technology to express high levels of synaptotagmin I and/or synaptotagmin II (Syt I/Syt II).

In one embodiment in which the VAMP cleaving neurotoxin is a BoNT/FA, a BoNT/F, a BoNT/D or a TeNT, the cell expresses high levels of synaptic vesicle protein (SV2). In one embodiment in which the VAMP cleaving neurotoxin is a BoNT/FA, a BoNT/F, a BoNT/D or a TeNT, the cell is modified by recombinant technology to express high levels of synaptic vesicle protein (SV2).

As used herein, "conditions suitable for clostridial neurotoxin activity" refers to conditions (e.g. temperature, pH, cofactors, etc) under which the clostridial neurotoxin can bind to a clostridial neurotoxin receptor present on the cell membrane, translocate the clostridial neurotoxin light chain into the cell cytoplasm and cleave a VAMP.

In one embodiment of the methods of the invention, the conditions suitable for clostridial neurotoxin activity can comprise incubation at about 37° C. for a period of from about 1 hour to about 48 hours. In one embodiment of the method of the invention, the conditions suitable for clostridial neurotoxin activity can comprise incubation at about 37° C. for a period of from about 2 hours to about 36 hours. In one embodiment of the method of the invention, the conditions suitable for clostridial neurotoxin activity can comprise incubation at about 37° C. for a period of from about 4 hours to about 24 hours.

For example, conditions suitable for clostridial neurotoxin activity can comprise incubation at 37° C. for 24 hours.

As used herein, "conditions suitable for the binding of a first detection antibody to cleaved VAMP" and "conditions suitable for the binding of a second detection antibody to full-length VAMP" refer to conditions (e.g. temperature, pH, cofactors, etc) under which the first and/or second detection antibody can bind to cleaved VAMP and/or full-length VAMP.

In one embodiment of the method of the invention, the conditions suitable for antibody binding can comprise incubation at about 4° C. for a period of from about 8 hours to about 48 hours. In one embodiment of the method of the invention, the conditions suitable for antibody binding can comprise incubation at about 4° C. for a period of from about 10 hours to about 24 hours. In one embodiment of the method of the invention, the conditions suitable for antibody binding can comprise incubation at about 4° C. for a period of from about 12 hours to about 16 hours.

In one embodiment of the method of the invention, the conditions suitable for antibody binding can comprise incubation at about 25° C. for a period of from about 30 minutes hour to about 8 hours. In one embodiment of the method of the invention, the conditions suitable for antibody binding can comprise incubation at about 25° C. for a period of from about 1 hour to about 4 hours. In one embodiment of the method of the invention, the conditions suitable for antibody binding can comprise incubation at about 25° C. for a period of from about 1.5 hours to about 3 hours.

Means suitable for detecting and quantifying the binding of a detection antibody to cleaved or full-length VAMP are well known in the art. For example, binding of a detection antibody to cleaved or full-length VAMP can be detected and quantified by Western blotting. As each protein runs at a specific molecular weight via SDS-PAGE, the cleaved VAMP will be detected at lower molecular weights than the full-length VAMP. Analysis of the bands by densitometry allows a percentage cleavage readout using both the full-length band and the cleavage band within the same lane on the gel. Alternatively, VAMP cleavage can be detected and quantified using an enzyme-linked immunosorbent assay (ELISA), for example a sandwich ELISA.

In one embodiment of the methods of the invention, the first detection antibody is a polyclonal antibody and the binding of the first detection antibody to the C-terminal VAMP cleavage product is detected and quantified in an enzyme-linked immunosorbent assay.

In one embodiment of the methods of the invention, the first detection antibody is a polyclonal antibody and the binding of the first detection antibody to the C-terminal VAMP cleavage product is detected and quantified in a western blot assay.

In one embodiment of the methods of the invention, the first detection antibody is a monoclonal antibody and the binding of the first detection antibody to the C-terminal VAMP cleavage product is detected and quantified in an enzyme-linked immunosorbent assay.

In one embodiment of the methods of the invention, the first detection antibody is a monoclonal antibody and the binding of the first detection antibody to the C-terminal VAMP cleavage product is detected and quantified in a western blot assay.

In one embodiment of the methods of the invention, the cell is lysed prior to contacting of its cytoplasmic content with the detection antibody(ies).

In an alternative embodiment of the methods of the invention, the cell is permeabilized prior to contacting of its cytoplasmic content with the detection antibody(ies).

In another aspect, the invention provides a kit comprising a cell which is susceptible to intoxication by a VAMP cleaving neurotoxin; and a first detection antibody against cleaved VAMP, wherein said first detection antibody is an antibody according to the invention.

In one embodiment, the kit further comprises a second detection antibody which binds to full-length VAMP but not to the C-terminal VAMP cleavage product. Suitably, the second detection antibody binds to a VAMP epitope which is N-terminal to a clostridial neurotoxin cleavage site. Examples of suitable antibodies include commercially available antibodies such as ab3347 (Abcam) or ab181869 (Abcam).

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a clostridial neurotoxin" includes a plurality of such candidate agents and reference to "the clostridial neurotoxin" includes reference to one or more clostridial neurotoxins and equivalents thereof known to those skilled in the art, and so forth.

The invention will now be described, by way of example only, with reference to the following Figures and Examples.

FIGURES

FIG. 1—VAMP sequences with clostridial neurotoxin cleavages sites. (A) human and rat VAMP1, VAMP2 and VAMP3 sequences with BoNT/F5 and BoNT/FA, BoNT/F, BoNT/D and BoNT/DC, BoNT/B, BoNT/G, TeNT and BoNT/X cleavage sites. (B) human and rat VAMP4, VAMP5 and YKT6 sequences with BoNT/X cleavage sites.

FIG. 2—VAMP sequences with Ab epitopes (i.e. immunogenic epitope regions) and BoNT/F, BoNT/D and BoN/B cleavages sites. The sequences for human and rat VAMP1, VAMP2 and VAMP3 are shown for comparison. Rat and human VAMP2 sequences are identical in the epitope regions selected. The cleavage sites are indicated by arrows: the VAMP2 cleavage points for BoNT/F and BoNT/D are located on adjacent amino acids, Q58-K59 and K59-L60 respectively, while the cleavage point for BoNT/B is located on amino acids Q76-F77 (based on human VAMP2 sequence amino acid position).

FIG. 3—Cell-free cleavage of recombinant VAMP2-GFP with MBP-LF and $LH_ND$. Recombinant VAMP2-GFP was incubated with 0.01 µg/µl $LH_ND$ or MBP-LF for 1 hr at 37° C. Equal volumes of sample buffer were added and 0.5 µg (Coomassie) and 0.3 µg (blots) protein run via SDS-PAGE and either stained with Coomassie or blotted with various anti-VAMP2 antibodies. The cartoon indicates the location of the antibody epitopes. The representation of the recombinant protein and the line length of the epitopes are not to scale. 1—BSA, 2—VAMP2-GFP, 3—Cleaved VAMP2-GFP (aa59/60-end), 4—Cleaved VAMP2-GFP (aa1-58/59).

Figure 4:
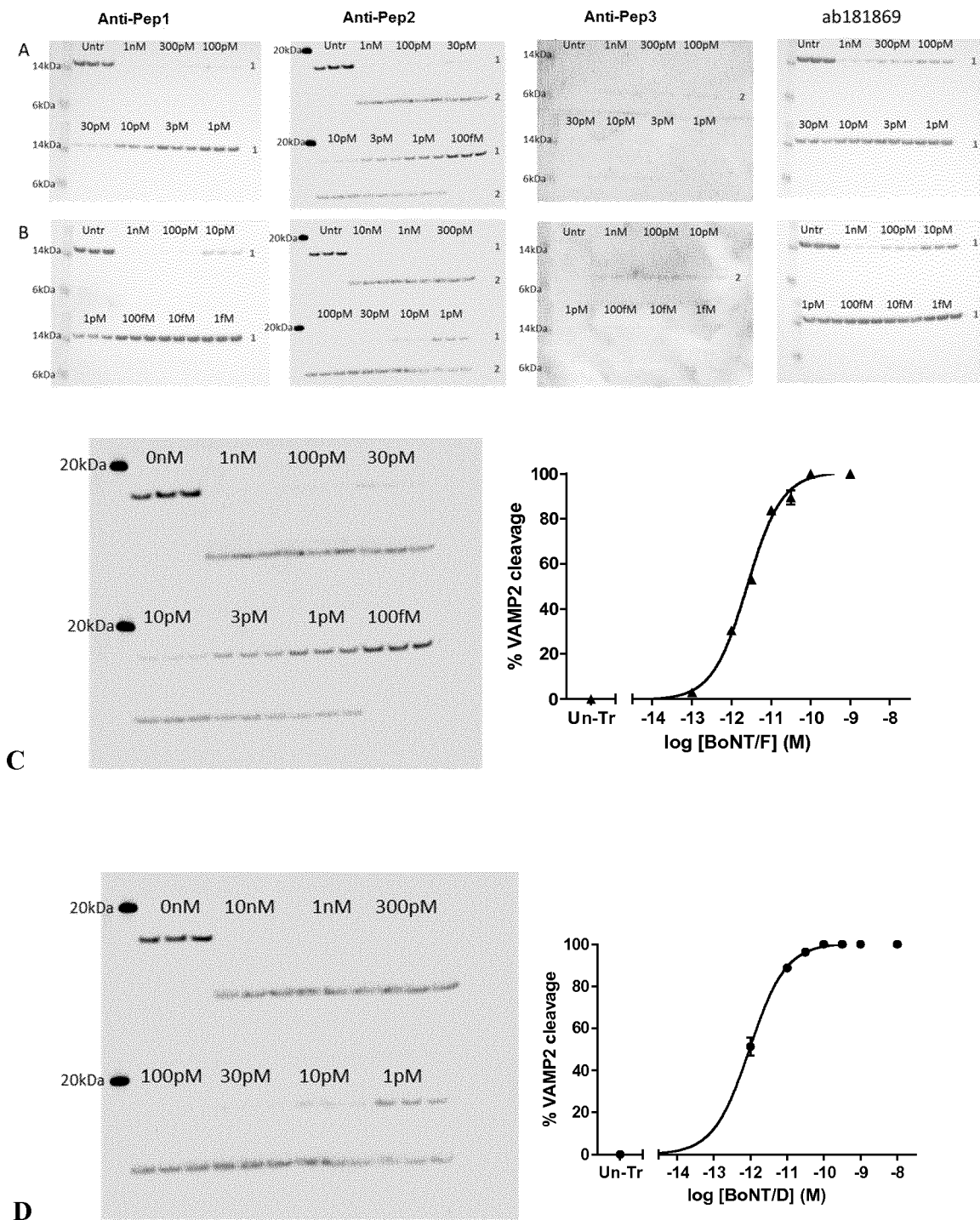

FIG. 4—In vitro VAMP cleavage after BoNT/F and BoNT/D treatment. Rat cortical neurons grown in 96 well plates until DIV18-21 were treated for 24 hours with either BoNT/F (A) or BoNT/D (B). Lysates were run via SDS-PAGE and blotted with the custom-made anti-VAMP2 antibodies: anti-Pep1, anti-Pep2 or anti-Pep3, or with the commercial antibody ab181869. 1—full-length VAMP2, 2—cleaved VAMP2. The anti-pep 2 data show the dose dependent disappearance of full-length VAMP2 and the appearance of the lower molecular weight cleaved fragment. Both band signals were used to quantify the dose dependent percentage of VAMP2 cleavage by BoNT/F (C) and BoNT/D (D).

FIG. 5—Rat cortical neurons were treated with natural BoNT/F1 (□), natural BoNT/A1 (●) or recombinant BoNT/FA (Δ) for 24 hours. Cell were lysed, run on SDS-PAGE and blotted for VAMP-2 or SNAP-25 cleavage. Percent SNARE cleavage was determined from the ratio of full-length to cleaved protein by densitometric analysis. Data were fitted using a four-parameter logistic equation and the concentration of BoNT required for 50% maximal SNARE cleavage (pEC50) determined. Data are mean±s.e.m. (n=3 (BoNT/F1 and BoNT/A1) or 4 (BoNT/FA) independent experiments in triplicate).

Figure 6:
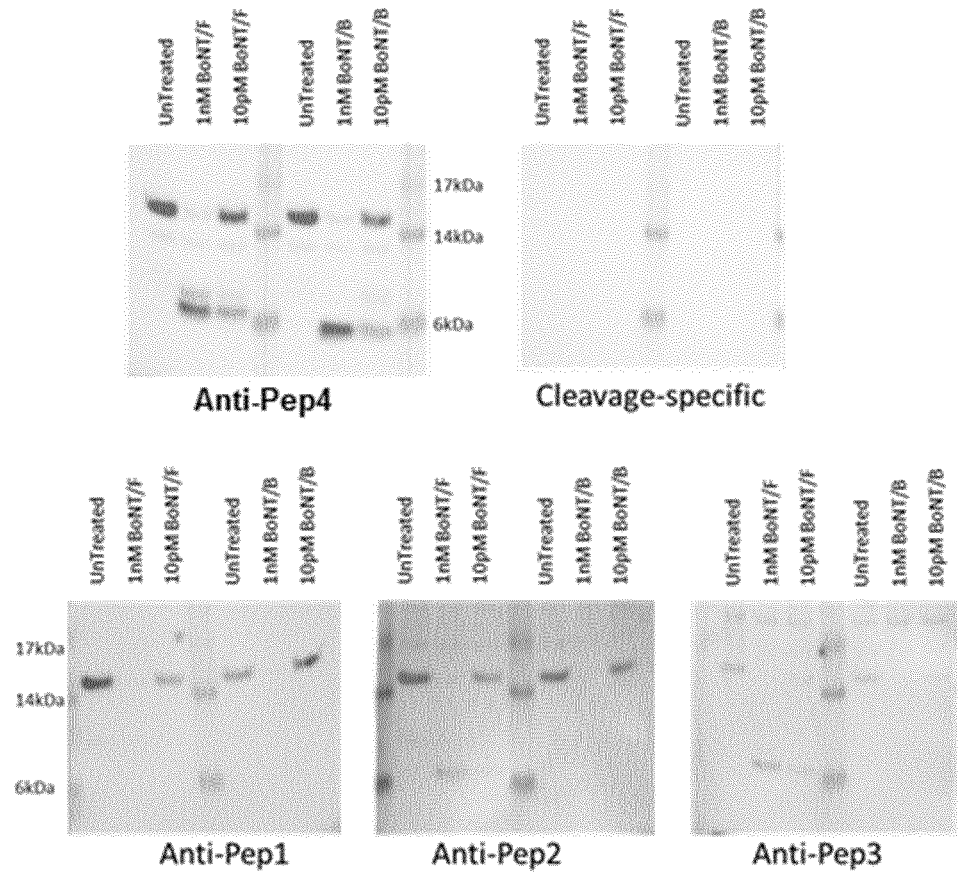

FIG. 6—in vitro VAMP cleavage after BoNT/B and BoNT/F treatment. Rat cortical neurons grown until DIV18-21 were treated for 24 hours with either BoNT/F or BoNT/B. Lysates were run via SDS-PAGE and blotted with a new custom-made anti-VAMP2 antibody (anti-Pep4), a BoNT/B cleavage-specific anti-VAMP2 antibody or anti-Pep1, anti-Pep2 or anti-Pep3 antibodies.

EXAMPLES

Example 1: Detection of VAMP Proteolytic Cleavage by BoNT/D and BoNT/F

A—Methods

1. Antibody Generation

Antibodies were generated by Eurogentec using their Speedy 28 day programme (https://secure.eurogentec.com/product/research-anti-protein-28-day-speedy-polyclonal-packages.html?country=gbr). Two rabbits per peptide were immunised with the following peptides:

```
VAMP PEP1:
                               (SEQ ID NO: 39)
H2N-SNR RLQ QTQ AQV DEC-CONH2;

VAMP PEP2:
                               (SEQ ID NO: 15)
AcNH-KLS ELD DRA DAL Q-CONH2;
```

-continued or

VAMP PEP3:

(SEQ ID NO: 40)

H2N-CLQ AGA SQ-CONH2.

Animals underwent a first immunisation and three subsequent boosters. A pre-immune bleed, medium bleed and a final bleed were taken.

2. Recombinant Protein Cleavage

Active constructs containing the light chain and translocation domain of BoNT/D or the equivalent BoNT/F domains fused to a maltose-binding protein (MPB) were generated as previously described (Masuyer et al., "Structure and activity of a functional derivative of Clostridium botulinum neurotoxin B. J Struct Biol", 174, p 52-57, 2011; Sutton et al., "Preparation of specifically activatable endopeptidase derivatives of Clostridium botulinum toxins type A, B, and C and their applications. Protein Expression and Purification 40:31-41, 2005). Briefly, either $LH_ND$ (SEQ ID NO: 35) or a fusion protein called MBP-LF (SEQ ID NO: 36) (the latter being a fusion of MBP with the light chain of BoNT/F1 and a C-terminal 6-histidine motif; MPB and the 6-histidine motif being commonly known affinity tags) were diluted to 0.01 µg/µl in assay buffer (50 mM HEPES pH7.2, 200 µM ZnCl2, 1 µg/µl BSA, 10 mM DTT). VAMP2-GFP (SEQ ID NO: 37) (a fusion protein of amino acids 2-94 of human VAMP2 and the detectable marker green fluorescent protein (GFP)) was diluted to 8 µM in assay buffer (50 mM HEPES pH7.2, 200 µM ZnCl2, 1 µg/µl BSA, 10 mM DTT). Equal volumes of $LH_ND$ or MBP-LF and VAMP2-GFP (SEQ ID NO: 37) (8 µM) were combined and incubated at 37° C. for 1 hour. Reactions were stopped by adding 2× reducing sample buffer (NuPage LDS sample buffer, 100 mM DTT).

3. Rat Cortical Neuronal Cell Culture

Rat cortical neurons were prepared from E17-E18 CD rat embryos. Dissected cortical tissue was collected into ice-cold Hank's Balanced Salt Solution (HBSS) w/o Ca2+ or Mg2+, and then dissociated in papain solution for 40 minutes at 37° C. following the manufacturer's instructions (Worthington Biochemical, NJ, US). Cortical cells were plated on poly-L-ornithine (PLO) coated 96-well plates at a density of 20,000 cells/well in 125 µl Neurobasal media containing 2% B27 supplement, 0.5 mM GlutaMAX, 1% foetal bovine serum (FBS) and 100 U/ml penicillin/streptomycin. Cells were maintained at 37° C. in a humidified atmosphere containing 5% CO2. A further 125 µl Neurobasal media containing 2% B27, 0.5 mM GlutaMAX was added on DIV (days in vitro) 4. Cells were maintained by replacement of half media twice per week. On DIV 11, 1.5 µM cytosine 3-D-arabinofuranoside (AraC) was added to the media to prevent proliferation of non-neuronal cells.

4. BoNT Treatment

Rat cortical neurons at DIV 18-21 were treated with a concentration range of native BoNT/F1 (Metabiologics, US) (1 nM-0.1 pM), or BoNT/D (Metabiologics, US) (10 nM-1 pM) in triplicate wells for 24 hours at 37° C. Media were removed and cells washed once with PBS. Cells were lysed in 40 µl LDS sample buffer (NuPage LDS buffer, 1 mM DTT, 1:500 Benzonase) for 10 minutes at room temperature.

5. SDS-PAGE and Western Blot

Neuronal lysates were boiled at 90° C. for 5 minutes. 15 µl lysates were loaded per lane to 12% Bis-Tris gels and run in MES buffer at 200V for 50 min. Proteins were transferred to nitrocellulose membranes via a Transblot Turbo (Biorad) using the low MW programme. Membranes were blocked for 1 hour at room temperature with 5% low fat milk/PBS-Tween and then incubated with the custom made anti-Pep1, anti-Pep2 or anti-Pep3 anti-VAMP2 primary antibodies, or with the commercial anti-VAMP2 antibodies (Abcam ab3347 and ab181869), overnight at 4° C. Membranes were washed 3 times in PBS-Tween and incubated with anti-rabbit-HRP secondary antibody for 1 hour at room temperature.

Membranes were washed for 3×5 mins in PBS-Tween, then developed with SuperSignal West Femto chemiluminescent substrate and visualised using a Syngene PXi system.

B—Results

Assessment of Recombinant Protein Detection

The regions of the chosen three peptide epitopes from VAMP2 relative to BoNT cleavage sites are shown in FIG. 2. The sequences for human and rat VAMP1, VAMP2 and VAMP3 are shown for comparison. Rat and human VAMP2 sequences are identical in the epitopes regions selected. The cleavage sites for BoNT/B and BoNT/D are located on adjacent amino acids.

Initially, the antibodies were tested in a cell free assay using recombinant VAMP2-GFP. BoNT/F and BoNT/D substitutes (MBP-LF and $LH_ND$) containing the enzymatic light chain domains of the toxin were used to cleave the VAMP protein (FIG. 3). In addition, two other commercially available VAMP2 antibodies were used as a comparison; ab3347 (epitope aa1-18) and ab181869 (epitope within aa1-100). FIG. 3 shows that anti-Pep1 antibody detected full-length VAMP2 and the N-terminal cleaved portion (aa1-58/59) with much reduced signal. As expected, there was no C-terminal cleavage product detection by this antibody, since its epitope was not located on this portion. Anti-Pep2 and Anti-Pep3 antibodies detected both the full-length protein and the C-terminal cleaved products of VAMP2-GFP. Ab3347 only detected full-length VAMP2 and not the N-terminal cleavage fragment whereas ab181869 detected both.

These first results show that the antibodies were able to detect full-length and the expected cleaved products of recombinant VAMP2. The exception was ab3347 which only detected full-length VAMP2 and not the N-terminal cleavage fragment.

Assessment of Endogenous Protein Detection

The next question was whether these antibodies could detect any cleavage products in a neuronal cell assay in which endogenous proteases would be present. Rat primary cortical neurons were treated with either BoNT/F or BoNT/D and lysed for WB analysis (FIG. 4). The anti-Pep1 antibody only recognised the full-length protein and there was no detectable cleavage product. The anti-Pep 2 antibody detected both the full-length and the C-terminal cleaved product. The anti-Pep3 antibody showed a weak signal very poor affinity for monomer VAMP within a cell lysate and detected higher molecular weight species which were most likely to be dimers and other proteins (data not shown). The full-length monomer signal was very low but there was a band for the BoNT/F and BoNT/D cleaved C-terminal product. In other words, anti-Pep3 did not detect full-length VAMP but weakly detected the BoNT/F and BoNT/D cleaved C-terminal fragment. This was in contrast to the earlier cell-free results which showed a strong signal from the full-length and cleaved recombinant VAMP. The commercial antibody Ab3347 was not tested in vitro due to the absence of cleaved protein detection in the cell-free assay. Despite the positive binding to the N-terminal cleaved recombinant fragment in the cell-free assay, the commercial antibody ab181869 detected full-length VAMP2 in the cortical lysates, but not a cleaved fragment in the cortical lysates. The Pep 2 data was used to quantify the dose dependent cleavage of VAMP2 by BoNT/F (FIG. 4C) and BoNT/D (FIG. 4D).

The inventors have initially shown that, in a cell-free system, both recombinant VAMP cleavage products can be detected. However, when transferred to a cellular lysate, the inventors have also shown that the N-terminal product is not detectable, but there may be other mechanisms involved, apart from degradation, that are yet unknown. In contrast, the inventors have shown that the C-terminal VAMP fragment which is still bound to the vesicle membrane is not degraded or altered in a manner that would prevent antibody binding and detection by Western Blot. The Pep2 epitope is adjacent to the BoNT/D and BoNT/F cleavage site and the antibody generated against this peptide detects both full-length VAMP and the cleaved product. In contrast, the anti-Pep3 antibody, which was generated against a shorter epitope further away from the BoNT F/D cleavage site, also detects, albeit weakly, the cleaved product.

Example 2: Detection of VAMP Proteolytic Cleavage by BoNT/FA and BoNT/F1 in Rat Cortical Neurons A—Methods 1. Rat Cortical Neuronal Cell Culture Rat cortical neurons were prepared as detailed in Example 1.

2. BoNT Treatment

Rat cortical neurons at DIV 18-21 were treated with a concentration range (1 pM-1 fM) of recombinant BoNT/FA (SEQ ID NO: 38), or a concentration range (1 nM-1 p B—Results Based on the results obtained in the above-described Examples 1 and 2, which implied the location of the epitope was key to detection of cleaved VAMP in vitro, a new monoclonal antibody was generated against the epitope adjacent to the BoNT/B cleavage site located on the C-Terminal side.

This antibody was tested in the same rat cortical assay following BoNT/B and BoNT/F treatment and compared with anti-Pep1, anti-Pep2, anti-Pep3 and a BoNT/B cleavage-specific antibody (FIG. 6). The epitope regions for all comparison antibodies were located on the N-terminal side of the BoNT/B cleavage site. FIG. 6 show that the location of the epitope of the new antibody directed against Pep4 enabled detection of the full-length VAMP2, as well as of the cleaved products for both BoNT/B and BoNT/F treatment. In contrast, the anti-Pep2 and anti-Pep3 antibodies only detected the BoNT/F cleaved product but not the BoNT/B cleaved product. The anti-Pep1 antibody did not detect any cleavage product as expected. The BoNT/B cleavage-specific antibody also did not detect any BoNT/B cleavage product in these cell lysates.

Overall, the present data show that an important consideration for cleaved VAMP detection is the location of the antibody epitope. Only antibodies raised against epitopes located on the membrane-bound VAMP fragment, post-cleavage, were able to detect the fragment. By locating the monoclonal antibody epitope towards the C-terminal end of VAMP, it was hypothesized that this region should be present in the VAMP fragments produced by the VAMP-cleaving neurotoxin serotypes B, D and F. This proved to be the case, enabling to generate a single antibody (anti-Pep4 Mab) which provided positive results for BoNT/B and BoNT/F treated neurons. Besides, since TeNT shares the same cleavage site as BoNT/B and BoNT/D cleavage site is in close vicinity to BoNT/F cleavage site, it is expected that this antibody will also be applicable to TeNT and BoNT/D cleavage.

An additional advantage of the Pep4 epitope region is that antibodies directed against this region can detect both full length and cleaved VAMP with similar sensitivity. The ability to simultaneously detect both protein forms within the same sample provides a robust tool for normalisation, without the need to blot for additional housekeeping proteins. This provides a very useful and straightforward gain of signal Western blot assay for quantification of BoNT potency in cell models.

The present data also show differences in VAMP detection between cell-free recombinant protein assays and a whole cell model. It was precisely this inability to detect cellular cleaved VAMP which formed the basis of the hypothesis that VAMP degradation in the cell occurred very quickly (Foran et al., "Evaluation of the therapeutic usefulness of botulinum neurotoxin B, C1, E and F compared with the long-lasting type A". J. Biol Chem 278 (2) pp 1363-1371 2003). In contrast to the antibodies of the present invention, the majority of commercially available VAMP antibodies are raised against epitopes within the N-terminal region of the protein and therefore the N-terminal VAMP fragment was the focus of those earlier studies. Although it is shown herein that the smaller C-terminal VAMP fragment is not degraded in a cell, the larger N-terminal fragment was not detected either. It is interesting to note however that, our cell-free results show that not all commercial antibodies are able to detect the expected N-terminal fragment even when it is present in a cell-free system lacking any proteases. From the present data, it can be concluded that the VAMP degradation hypothesis most certainly relates only to the N-terminal fragment, and that the C-terminal VAMP fragment is not degraded and remains bound to the vesicle membrane.

Sequence Information

-BoNT/A1-UniProtKB Accession Number P10845 (*Clostridium botulinum*)

SEQ ID NO: 1

MPFVNKQFNYKDPVNGVDIAYIKIPNAGQMQPVKAFKIHNKIWVIPERDTFT

NPEEGDLNPPPEAKQVPVSYYDSTYLSTDNEKDNYLKGVTKLFERIYSTDLG

RMLLTSIVRGIPFWGGSTIDTELKVIDTNCINVIQPDGSYRSEELNLVIIGPSADI

IQFECKSFGHEVLNLTRNGYGSTQYIRFSPDFTFGFEESLEVDTNPLLGAGKFA

TDPAVTLAHELIHAGHRLYGIAINPNRVFKVNTNAYYEMSGLEVSFEELRTFG

GHDAKFIDSLQENEFRLYYYNKFKDIASTLNKAKSIVGTTASLQYMKNVFKE

KYLLSEDTSGKFSVDKLKFDKLYKMLTEIYTEDNFVKFFKVLNRKTYLNFDK

AVFKINIVPKVNYTIYDGFNLRNTNLAANFNGQNTEINNMNFTKLKNFTGLFE

FYKLLCVRGIITSKTKSLDKGYNKALNDLCIKVNNWDLFFSPSEDNFTNDLNK

GEEITSDTNIEAAEENISLDLIQQYYLTFNFDNEPENISIENLSSDIIGQLELMPNI

ERFPNGKKYELDKYTMFHYLRAQEFEHGKSRIALTNSVNEALLNPSRVYTFF

SSDYVKKVNKATEAAMFLGWVEQLVYDFTDETSEVSTTDKIADITIIIPYIGPA

LNIGNMLYKDDFVGALIFSGAVILLEFIPEIAIPVLGTFALVSYIANKVLTVQTI

DNALSKRNEKWDEVYKYIVTNWLAKVNTQIDLIRKKMKEALENQAEATKAI

INYQYNQYTEEEKNNINFNIDDLSSKLNESINKAMININKFLNQCSVSYLMNS

MIPYGVKRLEDFDASLKDALLKYIYDNRGTLIGQVDRLKDKVNNTLSTDIPFQ

LSKYVDNQRLLSTFTEYIKNIINTSILNLRYESNHLIDLSRYASKINIGSKVNFD

-continued

PIDKNQIQLFNLESSKIEVILKNAIVYNSMYENFSTSFWIRIPKYFNSISLNNEYT

IINCMENNSGWKVSLNYGEIIWTLQDTQEIKQRVVFKYSQMINISDYINRWIF

VTITNNRLNNSKIYINGRLIDQKPISNLGNIHASNNIMFKLDGCRDTHRYIWIK

YFNLFDKELNEKEIKDLYDNQSNSGILKDFWGDYLQYDKPYYMLNLYDPNK

YVDVNNVGIRGYMYLKGPRGSVMTTNIYLNSSLYRGTKFIIKKYASGNKDNI

VRNNDRVYINVVVKNKEYRLATNASQAGVEKILSALEIPDVGNLSQVVVMK

SKNDQGITNKCKMNLQDNNGNDIGFIGFHQFNNIAKLVASNWYNRQIERSSR

TLGCSWEFIPVDDGWGERPL

-BoNT/B1-UniProtKB Accession Number P10844 (*Clostridium botulinum*)

SEQ ID NO: 2

MPVTINNFNYNDPIDNNNIIMMEPPFARGTGRYYKAFKITDRIWIIPERYTFGY

KPEDFNKSSGIFNRDVCEYYDPDYLNTNDKKNIFLQTMIKLFNRIKSKPLGEK

LLEMIINGIPYLGDRRVPLEEFNTNIASVTVNKLISNPGEVERKKGIFANLIIFGP

GPVLNENETIDIGIQNHFASREGFGGIMQMKFCPEYVSVFNNVQENKGASIFN

RRGYFSDPALILMHELIHVLHGLYGIKVDDLPIVPNEKKFFMQSTDAIQAEEL

YTFGGQDPSIITPSTDKSIYDKVLQNFRGIVDRLNKVLVCISDPNININIYKNKF

KDKYKFVEDSEGKYSIDVESFDKLYKSLMFGFTETNIAENYKIKTRASYFSDS

LPPVKIKNLLDNEIYTIEEGFNISDKDMEKEYRGQNKAINKQAYEEISKEHLAV

YKIQMCKSVKAPGICIDVDNEDLFFIADKNSFSDDLSKNERIEYNTQSNYIEND

FPINELILDTDLISKIELPSENTESLTDFNVDVPVYEKQPAIKKIFTDENTIFQYL

YSQTFPLDIRDISLTSSFDDALLFSNKVYSFFSMDYIKTANKVVEAGLFAGWV

KQIVNDFVIEANKSNTMDKIADISLIVPYIGLALNVGNETAKGNFENAFEIAGA

SILLEFIPELLIPVVGAFLLESYIDNKNKIIKTIDNALTKRNEKWSDMYGLIVAQ

WLSTVNTQFYTIKEGMYKALNYQAQALEEIIKYRYNIYSEKEKSNINIDFNDI

NSKLNEGINQAIDNINNFINGCSVSYLMKKMIPLAVEKLLDFDNTLKKNLLNY

IDENKLYLIGSAEYEKSKVNKYLKTIMPFDLSIYTNDTILIEMFNKYNSEILNNI

ILNLRYKDNNLIDLSGYGAKVEVYDGVELNDKNQFKLTSSANSKIRVTQNQN

IIFNSVFLDFSVSFWIRIPKYKNDGIQNYIHNEYTIINCMKNNSGWKISIRGNRII

WTLIDINGKTKSVFFEYNIREDISEYINRWFFVTITNNLNNAKIYINGKLESNTD

IKDIREVIANGEIIFKLDGDIDRTQFIWMKYFSIFNTELSQSNIEERYKIQSYSEY

LKDFWGNPLMYNKEYYMFNAGNKNSYIKLKKDSPVGEILTRSKYNQNSKYI

NYRDLYIGEKFIIRRKSNSQSINDDIVRKEDYIYLDFFNLNQEWRVYTYKYFK

KEEEKLFLAPISDSDEFYNTIQIKEYDEQPTYSCQLLFKKDEESTDEIGLIGIHRF

YESGIVFEEYKDYFCISKWYLKEVKRKPYNLKLGCNWQFIPKDEGWTE

-BoNT/C1-UniProtKB Accession Number P18640 (*Clostridium botulinum*)

SEQ ID NO: 3

MPITINNFNYSDPVDNKNILYLDTHLNTLANEPEKAFRITGNIWVIPDRFSRNS

NPNLNKPPRVTSPKSGYYDPNYLSTDSDKDPFLKEIIKLFKRINSREIGEELIYR

LSTDIPFPGNNNTPINTFDFDVDFNSVDVKTRQGNNWVKTGSINPSVIITGPRE

NIIDPETSTFKLTNNTFAAQEGFGALSIISISPRFMLTYSNATNDVGEGRFSKSE

FCMDPILILMHELNHAMHNLYGIAIPNDQTISSVTSNIFYSQYNVKLEYAEIYA

-continued

```
FGGPTIDLIPKSARKYFEEKALDYYRSIAKRLNSITTANPSSFNKYIGEYKQKLI

RKYRFVVESSGEVTVNRNKFVELYNELTQIFTEFNYAKIYNVQNRKIYLSNVY

TPVTANILDDNVYDIQNGFNIPKSNLNVLFMGQNLSRNPALRKVNPENMLYL

FTKFCHKAIDGRSLYNKTLDCRELLVKNTDLPFIGDISDVKTDIFLRKDINEET

EVIYYPDNVSVDQVILSKNTSEHGQLDLLYPSIDSESEILPGENQVFYDNRTQN

VDYLNSYYYLESQKLSDNVEDFTFTRSIEEALDNSAKVYTYFPTLANKVNAG

VQGGLFLMWANDVVEDFTTNILRKDTLDKISDVSAIIPYIGPALNISNSVRRG

NFTEAFAVTGVTILLEAFPEFTIPALGAFVIYSKVQERNEIIKTIDNCLEQRIKR

WKDSYEWMMGTWLSRIITQFNNISYQMYDSLNYQAGAIKAKIDLEYKKYSG

SDKENIKSQVENLKNSLDVKISEAMNNINKFIRECSVTYLFKNMLPKVIDELN

EFDRNTKAKLINLIDSHNIILVGEVDKLKAKVNNSFQNTIPFNIFSYTNNSLLK

DIINEYFNNINDSKILSLQNRKNTLVDTSGYNAEVSEEGDVQLNPIFPFDFKLG

SSGEDRGKVIVTQNENIVYNSMYESFSISFWIRINKWVSNLPGYTIIDSVKNNS

GWSIGIISNFLVFTLKQNEDSEQSINFSYDISNNAPGYNKWFFVTVTNNMMGN

MKIYINGKLIDTIKVKELTGINFSKTITFEINKIPDTGLITSDSDNINMWIRDFYIF

AKELDGKDINILFNSLQYTNVVKDYWGNDLRYNKEYYMVNIDYLNRYMYA

NSRQIVFNTRRNNNDFNEGYKIIIKRIRGNTNDTRVRGGDILYFDMTINNKAY

NLFMKNETMYADNHSTEDIYAIGLREQTKDINDNIIFQIQPMNNTYYYASQIF

KSNFNGENISGICSIGTYRFRLGGDWYRHNYLVPTVKQGNYASLLESTSTHW

GFVPVSE

-BoNT/D-UniProtKB Accession Number P19321 (Clostridium
botulinum)
                                                SEQ ID NO: 4
MTWPVKDFNYSDPVNDNDILYLRIPQNKLITTPVKAFMITQNIWVIPERFSSDT

NPSLSKPPRPTSKYQSYYDPSYLSTDEQKDTFLKGIIKLFKRINERDIGKKLINY

LVVGSPFMGDSSTPEDTFDFTRHTTNIAVEKFENGSWKVTNIITPSVLIFGPLP

NILDYTASLTLQGQQSNPSFEGFGTLSILKVAPEFLLTFSDVTSNQSSAVLGKSI

FCMDPVIALMHELTHSLHQLYGINIPSDKRIRPQVSEGFFSQDGPNVQFEELYT

FGGLDVEIIPQIERSQLREKALGHYKDIAKRLNNINKTIPSSWISNIDKYKKIFSE

KYNFDKDNTGNFVVNIDKFNSLYSDLTNVMSEVVYSSQYNVKNRTHYFSRH

YLPVFANILDDNIYTIRDGFNLTNKGFNIENSGQNIERNPALQKLSSESVVDLF

TKVCLRLTKNSRDDSTCIKVKNNRLPYVADKDSISQEIFENKIITDETNVQNYS

DKFSLDESILDGQVPINPEIVDPLLPNVNMEPLNLPGEEIVFYDDITKYVDYLN

SYYYLESQKLSNNVENITLTTSVEEALGYSNKIYTFLPSLAEKVNKGVQAGLF

LNWANEVVEDFTTNIMKKDTLDKISDVSVIIPYIGPALNIGNSALRGNFNQAF

ATAGVAFLLEGFPEFTIPALGVFTFYSSIQEREKIIKTIENCLEQRVKRWKDSY

QWMVSNWLSRITTQFNHINYQMYDSLSYQADAIKAKIDLEYKKYSGSDKENI

KSQVENLKNSLDVKISEAMNNINKFIRECSVTYLFKNMLPKVIDELNKFDLRT

KTELINLIDSHNIILVGEVDRLKAKVNESFENTMPFNIFSYTNNSLLKDIINEYF

NSINDSKILSLQNKKNALVDTSGYNAEVRVGDNVQLNTIYTNDFKLSSSGDKI

IVNLNNNILYSAIYENSSVSFWIKISKDLTNSHNEYTIINSIEQNSGWKLCIRNG

NIEWILQDVNRKYKSLIFDYSESLSHTGYTNKWFFVTITNNIMGYMKLYINGE
```

-continued

LKQSQKIEDLDEVKLDKTIVFGIDENIDENQMLWIRDFNIFSKELSNEDINIVYE

GQILRNVIKDYWGNPLKFDTEYYIINDNYIDRYIAPESNVLVLVQYPDRSKLY

TGNPITIKSVSDKNPYSRILNGDNIILHMLYNSRKYMIIRDTDTIYATQGGECS

QNCVYALKLQSNLGNYGIGIFSIKNIVSKNKYCSQIFSSFRENTMLLADIYKPW

RFSFKNAYTPVAVTNYETKLLSTSSFWKFISRDPGWVE

-BoNT/E-Accession number WP_003372387 (*Clostridium botulinum*)

SEQ ID NO: 5

MPKINSFNYNDPVNDRTILYIKPGGCQEFYKSFNIMKNIWIIPERNVIGTTPQDF

HPPTSLKNGDSSYYDPNYLQSDEEKDRFLKIVTKIFNRINNNLSGGILLEELSK

ANPYLGNDNTPDNQFHIGDASAVEIKFSNGSQDILLPNVIIMGAEPDLFETNSS

NISLRNNYMPSNHGFGSIAIVTFSPEYSFRFNDNSMNEFIQDPALTLMHELIHS

LHGLYGAKGITTKYTITQKQNPLITNIRGTNIEEFLTFGGTDLNIITSAQSNDIY

TNLLADYKKIASKLSKVQVSNPLLNPYKDVFEAKYGLDKDASGIYSVNINKF

NDIFKKLYSFTEFDLATKFQVKCRQTYIGQYKYFKLSNLLNDSIYNISEGYNIN

NLKVNFRGQNANLNPRIITPITGRGLVKKIIRFCKNIVSVKGIRKSICIEINNGEL

FFVASENSYNDDNINTPKEIDDTVTSNNNYENDLDQVILNFNSESAPGLSDEK

LNLTIQNDAYIPKYDSNGTSDIEQHDVNELNVFFYLDAQKVPEGENNVNLTSS

IDTALLEQPKIYTFFSSEFINNVNKPVQAALFVSWIQQVLVDFTTEANQKSTVD

KIADISIVVPYIGLALNIGNEAQKGNFKDALELLGAGILLEFEPELLIPTILVFTI

KSFLGSSDNKNKVIKAINNALKERDEKWKEVYSFIVSNWMTKINTQFNKRKE

QMYQALQNQVNAIKTIIESKYNSYTLEEKNELTNKYDIKQIENELNQKVSIAM

NNIDRFLTESSISYLMKLINEVKINKLREYDENVKTYLLNYIIQHGSILGESQQE

LNSMVTDTLNNSIPFKLSSYTDDKILISYFNKFFKRIKSSSVLNMRYKNDKYV

DTSGYDSNININGDVYKYPTNKNQFGIYNDKLSEVNISQNDYIIYDNKYKNFSI

SFWVRIPNYDNKIVNVNNEYTIINCMRDNNSGWKVSLNHNEIIWTLQDNAGI

NQKLAFNYGNANGISDYINKWIFVTITNDRLGDSKLYINGNLIDQKSILNLGNI

HVSDNILFKIVNCSYTRYIGIRYFNIFDKELDETEIQTLYSNEPNTNILKDFWGN

YLLYDKEYYLLNVLKPNNFIDRRKDSTLSINNIRSTILLANRLYSGIKVKIQRV

NNSSTNDNLVRKNDQVYINFVASKTHLFPLYADTATTNKEKTIKISSSGNRFN

QVVVMNSVGNNCTMNFKNNNGNNIGLLGFKADTVVASTWYYTHMRDHTN

SNGCFWNFISEEHGWQEK

-BoNT/F-UniProtKB Accession Number YP_001390123 (*Clostridium botulinum*)

SEQ ID NO: 6

MPVVINSFNYNDPVNDDTILYMQIPYEEKSKKYYKAFEIMRNVWIIPERNTIG

TDPSDFDPPASLENGSSAYYDPNYLTTDAEKDRYLKTTIKLFKRINSNPAGEV

LLQEISYAKPYLGNEHTPINEFHPVTRTTSVNIKSSTNVKSSIILNLLVLGAGPD

IFENSSYPVRKLMDSGGVYDPSNDGFGSINIVTFSPEYEYTFNDISGGYNSSTE

SFIADPAISLAHELIHALHGLYGARGVTYKETIKVKQAPLMIAEKPIRLEEFLTF

GGQDLNIITSAMKEKIYNNLLANYEKIATRLSRVNSAPPEYDINEYKDYFQWK

YGLDKNADGSYTVNENKFNEIYKKLYSFTEIDLANKFKVKCRNTYFIKYGFL

KVPNLLDDDIYTVSEGFNIGNLAVNNRGQNIKLNPKIIDSIPDKGLVEKIVKFC

KSVIPRKGTKAPPRLCIRVNNRELFFVASESSYNENDINTPKEIDDTTNLNNNY

-continued

```
RNNLDEVILDYNSETIPQISNQTLNTLVQDDSYVPRYDSNGTSEIEEHNVVDL
NVFFYLHAQKVPEGETNISLTSSIDTALSEESQVYTFFSSEFINTINKPVHAALFI
SWINQVIRDFTTEATQKSTFDKIADISLVVPYVGLALNIGNEVQKENFKEAFEL
LGAGILLEFVPELLIPTILVFTIKSFIGSSENKNKIIKAINNSLMERETKWKEIYS
WIVSNWLTRINTQFNKRKEQMYQALQNQVDAIKTVIEYKYNNYTSDERNRL
ESEYNINNIREELNKKVSLAMENIERFITESSIFYLMKLINEAKVSKLREYDEG
VKEYLLDYISEHRSILGNSVQELNDLVTSTLNNSIPFELSSYTNDKILILYFNKL
YKKIKDNSILDMRYENNKFIDISGYGSNISINGDVYIYSTNRNQFGIYSSKPSEV
NIAQNNDIIYNGRYQNFSISFWVRIPKYFNKVNLNNEYTIIDCIRNNNSGWKIS
LNYNKIIWTLQDTAGNNQKLVFNYTQMISISDYINKWIFVTITNNRLGNSRIYI
NGNLIDEKSISNLGDIHVSDNILFKIVGCNDTRYVGIRYFKVFDTELGKTEIETL
YSDEPDPSILKDFWGNYLLYNKRYYLLNLLRTDKSITQNSNFLNINQQRGVY
QKPNIFSNTRLYTGVEVIIRKNGSTDISNTDNFVRKNDLAYINVVDRDVEYRL
YADISIAKPEKIIKLIRTSNSNNSLGQIIVMDSIGNNCTMNFQNNNGGNIGLLGF
HSNNLVASSWYYNNIRKNTSSNGCFWSFISKEHGWQEN
```

-BoNT/G-UniProtKB Accession Number WP_039635782
(*Clostridium botulinum*)

SEQ ID NO: 7

```
MPVNIKNFNYNDPINNDDIIMMEPFNDPGPGTYYKAFRIIDRIWIVPERFTYGF
QPDQFNASTGVFSKDVYEYYDPTYLKTDAEKDKFLKTMIKLFNRINSKPSGQ
RLLDMIVDAIPYLGNASTPPDKFAANVANVSINKKIIQPGAEDQIKGLMTNLII
FGPGPVLSDNFTDSMIMNGHSPISEGFGARMMIRFCPSCLNVFNNVQENKDTS
IFSRRAYFADPALTLMHELIHVLHGLYGIKISNLPITPNTKEFFMQHSDPVQAE
ELYTFGGHDPSVISPSTDMNIYNKALQNFQDIANRLNIVSSAQGSGIDISLYKQI
YKNKYDFVEDPNGKYSVDKDKFDKLYKALMFGFTETNLAGEYGIKTRYSYF
SEYLPPIKTEKLLDNTIYTQNEGFNIASKNLKTEFNGQNKAVNKEAYEEISLEH
LVIYRIAMCKPVMYKNTGKSEQCIIVNNEDLFFIANKDSFSKDLAKAETIAYN
TQNNTIENNFSIDQLILDNDLSSGIDLPNENTEPFTNFDDIDIPVYIKQSALKKIF
VDGDSLFEYLHAQTFPSNIENLQLTNSLNDALRNNNKVYTFFSTNLVEKANT
VVGASLFVNWVKGVIDDFTSESTQKSTIDKVSDVSIIIPYIGPALNVGNETAKE
NFKNAFEIGGAAILMEFIPELIVPIVGFFTLESYVGNKGHIIMTISNALKKRDQK
WTDMYGLIVSQWLSTVNTQFYTIKERMYNALNNQSQAIEKIIEDQYNRYSEE
DKMNINIDFNDIDFKLNQSINLAINNIDDFINQCSISYLMNRMIPLAVKKLKDF
DDNLKRDLLEYIDTNELYLLDEVNILKSKVNRHLKDSIPFDLSLYTKDTILIQV
FNNYISNISSNAILSLSYRGGRLIDSSGYGATMNVGSDVIFNDIGNGQFKLNNS
ENSNITAHQSKFVVYDSMFDNFSINFWVRTPKYNNNDIQTYLQNEYTIISCIKN
DSGWKVSIKGNRIIWTLIDVNAKSKSIFFEYSIKDNISDYINKWFSITITNDRLG
NANIYINGSLKKSEKILNLDRINSSNDIDFKLINCTDTTKFVWIKDFNIFGRELN
ATEVSSLYWIQSSTNTLKDFWGNPLRYDTQYYLFNQGMQNIYIKYFSKASMG
ETAPRTNFNNAAINYQNLYLGLRFIIKKASNSRNINNDNIVREGDYIYLNIDNIS
DESYRVYVLVNSKEIQTQLFLAPINDDPTFYDVLQIKKYYEKTTYNCQILCEK
```

```
DTKTFGLFGIGKFVKDYGYVWDTYDNYFCISQWYLRRISENINKLRLGCNWQ

FIPVDEGWTE
```

-TeNT-UniProtKB Accession Number P04958 (*Clostridium tetani*)

SEQ ID NO: 8
```
MPITINNFRYSDPVNNDTIIMMEPPYCKGLDIYYKAFKITDRIWIVPERYEFGT

KPEDFNPPSSLIEGASEYYDPNYLRTDSDKDRFLQTMVKLFNRIKNNVAGEAL

LDKIINAIPYLGNSYSLLDKFDTNSNSVSFNLLEQDPSGATTKSAMLTNLIIFGP

GPVLNKNEVRGIVLRVDNKNYFPCRDGFGSIMQMAFCPEYVPTFDNVIENITS

LTIGKSKYFQDPALLLMHELIHVLHGLYGMQVSSHEIIPSKQEIYMQHTYPISA

EELFTFGGQDANLISIDIKNDLYEKTLNDYKAIANKLSQVTSCNDPNIDIDSYK

QIYQQKYQFDKDSNGQYIVNEDKFQILYNSIMYGFTEIELGKKFNIKTRLSYFS

MNHDPVKIPNLLDDTIYNDTEGFNIESKDLKSEYKGQNMRVNTNAFRNVDGS

GLVSKLIGLCKKIIPPTNIRENLYNRTASLTDLGGELCIKIKNEDLTFIAEKNSFS

EEPFQDEIVSYNTKNKPLNFNYSLDKIIVDYNLQSKITLPNDRTTPVTKGIPYA

PEYKSNAASTIEIHNIDDNTIYQYLYAQKSPTTLQRITMTNSVDDALINSTKIYS

YFPSVISKVNQGAQGILFLQWVRDIIDDFTNESSQKTTIDKISDVSTIVPYIGPA

LNIVKQGYEGNFIGALETTGVVLLLEYIPEITLPVIAALSIAESSTQKEKIIKTID

NFLEKRYEKWIEVYKLVKAKWLGTVNTQFQKRSYQMYRSLEYQVDAIKKII

DYEYKIYSGPDKEQIADEINNLKNKLEEKANKAMININIFMRESSRSFLVNQMI

NEAKKQLLEFDTQSKNILMQYIKANSKFIGITELKKLESKINKVFSTPIPFSYSK

NLDCWVDNEEDIDVILKKSTILNLDINNDIISDISGFNSSVITYPDAQLVPGING

KAIHLVNNESSEVIVHKAMDIEYNDMFNNFTVSFWLRVPKVSASHLEQYGTN

EYSIISSMKKHSLSIGSGWSVSLKGNNLIWTLKDSAGEVRQITFRDLPDKFNA

YLANKWVFITITNDRLSSANLYINGVLMGSAEITGLGAIREDNNITLKLDRCN

NNNQYVSIDKFRIFCKALNPKEIEKLYTSYLSITFLRDFWGNPLRYDTEYYLIP

VASSSKDVQLKNITDYMYLTNAPSYTNGKLNIYYRRLYNGLKFIIKRYTPNNE

IDSFVKSGDFIKLYVSYNNNEHIVGYPKDGNAFNNLDRILRVGYNAPGIPLYK

KMEAVKLRDLKTYSVQLKLYDDKNASLGLVGTHNGQIGNDPNRDILIASNW

YFNHLKDKILGCDWYFVPTDEGWTND
```

-VAMP1 Rat (Q63666)

SEQ ID NO: 9
```
MSAPAQPPAEGTEGAAPGGGPPGPPPNTTSNRRLQQTQAQVEEVVDIMRVNV

DKVLERDQKLSELDDRADALQAGASVFESSAAKLKRKYWWKNCKMMIML

GAICAIIVVVIVIYIFT
```

-VAMP1 human (P23763)

SEQ ID NO: 10
```
MSAPAQPPAEGTEGTAPGGGPPGPPPNMTSNRRLQQTQAQVEEVVDIIRVNV

DKVLERDQKLSELDDRADALQAGASQFESSAAKLKRKYWWKNCKMMIML

GAICAIIVVVIVIYFFT
```

-VAMP2 Rat (P63045)

SEQ ID NO: 11
```
MSATAATVPPAAPAGEGGPPAPPPNLTSNRRLQQTQAQVDEVVDIMRVNVD

KVLERDQKLSELDDRADALQAGASQFETSAAKLKRKYWWKNLKMMIILGVI

CAIILIIIIVYFST
```

-continued

-VAMP2 human (P63027) SEQ ID NO: 12
MSATAATAPPAAPAGEGGPPAPPPNLTSNRRLQQTQAQVDEVVDIMRVNVD
KVLERDQKLSELDDRADALQAGASQFETSAAKLKRKYWWKNLKMMIILGVI
CAIILIIIIVYFST -VAMP3_Rat (P63025) SEQ ID NO: 13
MSTGVPSGSSAATGSNRRLQQTQNQVDEVVDIMRVNVDKVLERDQKLSELD
DRADALQAGASQFETSAAKLKRKYWWKNCKMWAIGISVLVIIVIIIIVWCVS VAMP3 human (Q15836) SEQ ID NO: 14
MSTGPTAATGSNRRLQQTQNQVDEVVDIMRVNVDKVLERDQKLSELDDRA
DALQAGASQFETSAAKLKRKYWWKNCKMWAIGITVLVIFIIIIIVWVSS -VAMP epitope SEQ ID NO: 15
KLSELDDRADALQ -VAMP epitope SEQ ID NO: 16
QKLSELDDRADALQ -VAMP epitope SEQ ID NO: 17
KLSELDDRAD -VAMP epitope SEQ ID NO: 18
KLSELDDRADALQAGAS -VAMP epitope SEQ ID NO: 19
LSELDDRADALQ -VAMP epitope SEQ ID NO: 20
LSELDDRADA -VAMP epitope SEQ ID NO: 21
LSELDDRADALQAGAS -VAMP epitope SEQ ID NO: 22
FETSAAKLKRKYW -VAMP epitope SEQ ID NO: 23
FESSAAKLKRKYW -VAMP epitope SEQ ID NO: 24
QFETSAAKLKRKYW -VAMP epitope SEQ ID NO: 25
FETSAAKLKR -VAMP epitope SEQ ID NO: 26
FETSAAKLKRKYWWKN -VAMP epitope SEQ ID NO: 27
AKLKRKYWWKN -VAMP epitope SEQ ID NO: 28
AAKLKRKYWWKN -VAMP epitope SEQ ID NO: 29
AKLKRKYWWKNCKM -VAMP epitope
SEQ ID NO: 30
AKLKRKYWWKNLKM -VAMP epitope
SEQ ID NO: 31
DQKLSELDDRADALQ -VAMP epitope
SEQ ID NO: 32
ERDQKLSELDDRA -VAMP epitope
SEQ ID NO: 33
LERDQKLSELDDRA -VAMP epitope
SEQ ID NO: 34
VLERDQKLSELDDRA

-LHND
SEQ ID NO: 35
MGSMTWPVKDFNYSDPVNDNDILYLRIPQNKLITTPVKAFMITQNIWVIPERF

SSDTNPSLSKPPRPTSKYQSYYDPSYLSTDEQKDTFLKGIIKLFKRINERDIGKK

LINYLVVGSPFMGDSSTPEDTFDFTRHTTNIAVEKFENGSWKVTNIITPSVLIFG

PLPNILDYTASLTLQGQQSNPSFEGFGTLSILKVAPEFLLTFSDVTSNQSSAVLG

KSIFCMDPVIALMHELTHSLHQLYGINIPSDKRIRPQVSEGFFSQDGPNVQFEE

LYTFGGLDVEIIPQIERSQLREKALGHYKDIAKRLNNINKTIPSSWISNIDKYKK

IFSEKYNFDKDNTGNFVVNIDKFNSLYSDLTNVMSEVVYSSQYNVKNRTHYF

SRHYLPVFANILDDNIYTIRDGFNLTNKGFNIENSGQNIERNPALQKLSSESVV

DLFTKVCVDKSEEKLYDDDDKDRWGSSLQCIKVKNNRLPYVADKDSISQEIF

ENKIITDETNVQNYSDKFSLDESILDGQVPINPEIVDPLLPNVNMEPLNLPGEEI

VFYDDITKYVDYLNSYYYLESQKLSNNVENITLTTSVEEALGYSNKIYTFLPS

LAEKVNKGVQAGLFLNWANEVVEDFTTNIMKKDTLDKISDVSVIIPYIGPALN

IGNSALRGNFNQAFATAGVAFLLEGFPEFTIPALGVFTFYSSIQEREKIIKTIENC

LEQRVKRWKDSYQWMVSNWLSRITTQFNHINYQMYDSLSYQADAIKAKIDL

EYKKYSGSDKENIKSQVENLKNSLDVKISEAMNNINKFIRECSVTYLFKNMLP

KVIDELNKFDLRTKTELINLIDSHNIILVGEVDRLKAKVNESFENTMPFNIFSYT

NNSLLKDIINEYFNLEAHHHHHHHHH

-MBP-LF
SEQ ID NO: 36
MKIEEGKLVIWINGDKGYNGLAEVGKKFEKDTGIKVTVEHPDKLEEKFPQVA

ATGDGPDIIFWAHDRFGGYAQSGLLAEITPDKAFQDKLYPFTWDAVRYNGKL

IAYPIAVEALSLIYNKDLLPNPPKTWEEIPALDKELKAKGKSALMFNLQEPYFT

WPLIAADGGYAFKYENGKYDIKDVGVDNAGAKAGLTFLVDLIKNKHMNAD

TDYSIAEAAFNKGETAMTINGPWAWSNIDTSKVNYGVTVLPTFKGQPSKPFV

GVLSAGINAASPNKELAKEFLENYLLTDEGLEAVNKDKPLGAVALKSYEEEL

AKDPRIAATMENAQKGEIMPNIPQMSAFWYAVRTAVINAASGRQTVDEALK

DAQTNSSSNNNNNNNNNLGIEGRISEFGSMPVAINSFNYNDPVNDDTILYM

QIPYEEKSKKYYKAFEIMRNVWIIPERNTIGTNPSDFDPPASLKNGSSAYYDPN

YLTTDAEKDRYLKTTIKLFKRINSNPAGKVLLQEISYAKPYLGNDHTPIDEFSP

VTRTTSVNIKLSTNVESSMLLNLLVLGAGPDIFESCCYPVRKLIDPDVVYDPSN

YGFGSINIVTFSPEYEYTFNDISGGHNSSTESFIADPAISLAHELIHALHGLYGA

-continued

RGVTYEETIEVKQAPLMIAEKPIRLEEFLTFGGQDLNIITSAMKEKIYNNLLAN

YEKIATRLSEVNSAPPEYDINEYKDYFQWKYGLDKNADGSYTVNENKFNEIY

KKLYSFTESDLANKFKVKCRNTYFIKYEFLKVPNLLDDDIYTVSEGFNIGNLA

VNNRGQSIKLNPKIIDSIPDKGLVEKIVKFAVDKLAAALEHHHHHH (recombinant VAMP2-GFP)

SEQ ID NO: 37

GPLGSSATAATAPPAAPAGEGGPPAPPPNLTSNRRLQQTQAQVDEVVDIMRV

NVDKVLERDQKLSELDDRADALQAGASQFETSAAKLKRKYWWKNLKLEN

VSKGEELFTGVVPILVELDGDVNGHKFSVSGEGEGDATYGKLTLKFICTTGK

LPVPWPTLVTTLTYGVQCFSRYPDHMKQHDFFKSAMPEGYVQERTIFFKDD

GNYKTRAEVKFEGDTLVNRIELKGIDFKEDGNILGHKLEYNYNSHNVYIMA

DKQKNGIKVNFKIRHNIEDGSVQLADHYQQNTPIGDGPVLLPDNHYLSTQSA

LSKDPNEKRDHMVLLEFVTAAGITLGMDELYK

-recombinant BoNT/FA

SEQ ID NO: 38

MPVVINSFNYDDPVNDNTIIYIRPPYYETSNTYFKAFQIMDNVWIIPERYRLGI

DPSLFNPPVSLKAGSDGYFDPNYLSTNTEKNKYLQIMIKLFKRINSKPAGQILL

EEIKNAIPYLGNSYTQEEQFTTNNRTVSFNVKLANGNIVQQMANLIIWGPGPD

LTTNKTGGIIYSPYQSMEATPYKDGFGSIMTVEFSPEYATAFNDISIASHSPSLF

IKDPALILMHELIHVLHGLYGTYITEYKITPNVVQSYMKVTKPITSAEFLTFGG

RDRNIVPQSIQSQLYNKVLSDYKRIASRLNKVNTATALINIDEFKNLYEWKYQ

FAKDSNGVYSVDLNKFEQLYKKIYSFTEFNLAYEFKIKTRLGYLAENFGPFYL

PNLLDDSIYTEVDGFNIGALSINYQGQNIGSDINSIKKLQGQGVVSRVVRLCKS

VIPRKGTKAPPRLCITVNNRDLFFIASQESYGENTINTYKEIDDTTTLDPSFEDI

LDKVILNFNEQVIPQMPNRNVSTDIQKDNYIPKYDYNRTDIIDSYEVGRNYNT

FFYLNAQKFSPNESNITLTSSFDTGLLEGSKVYTFFSSDFINNINKPVQALLFIE

WVKQVIRDFTTEATKTSTVDKLKDISLVVPYIGLALNIGDEIYKQHFAEAVEL

VGAGLLLEFSPEFLIPTLLIFTIKGYLTGSIRDKDKIIKTLDNALNVRDQKWKEL

YRWVVSKWLTTINTQFNKRKEQMYKALKNQATAIKKIIENKYNNYTTDEKS

KIDSSYNINEIERTLNEKINLAMKNIEQFITESSIAYLINIINNETIQKLKSYDDLV

RRYLLGYIRNHSSILGNSVEELNSKVNNHLDNGIPFELSSYTNDSLLIRYFNKN

YGELKYNCILNIKYEMDRDKLVDSSGYRSRINIGTGVKFSEIDKNQVQLSNLE

SSKIEVILNNGVIYNSMYENFSTSFWIRIPKYFRNINNEYKIISCMQNNSGWEV

SLNFSNMNSKIIWTLQDTEGIKKTVVFQYTQNINISDYINRWIFVTITNNRLSNS

KIYINGRLINEESISDLGNIHASNNIMFKLDGCRDPHRYIWIKYFNLFDKELNK

KEIKDLYDNQSNSGILKDFWGDYLQYDKPYYMLNLYDPNKYLDVNNVGIRG

YMYLKGPRGRIVTTNIYLNSTLYMGTKFIIKKYASGNKDNIVRNNDRVYINV

VVKNKEYRLATNASQAGVEKILSAVEIPDVGNLSQVVVMKSENDQGIRNKC

KMNLQDNNGNDIGFIGFHQFNNIAKLVASNWYNRQIGKASRTFGCSWEFIPV

DDGWGESSLHHHHHHHHHH

-continued

-Pep1
SEQ ID NO: 39
SNRRLQQTQAQVDEC

-Pep3
SEQ ID NO: 40
CLQAGASQ

-BoNT/X Genbank Accession Number BAQ12790 (*Clostridium botulinum*)
SEQ ID NO: 41
MKLEINKFNYNDPIDGINVITMRPPRHSDKINKGKGPFKAFQVIKNIWIVPERY

NFTNNTNDLNIPSEPIMEADAIYNPNYLNTPSEKDEFLQGVIKVLERIKSKPEG

EKLLELISSSIPLPLVSNGALTLSDNETIAYQENNNIVSNLQANLVIYGPGPDIA

NNATYGLYSTPISNGEGTLSEVSFSPFYLKPFDESYGNYRSLVNIVNKFVKREF

APDPASTLMHELVHVTHNLYGISNRNFYYNFDTGKIETSRQQNSLIFEELLTF

GGIDSKAISSLIIKKIIETAKNNYTTLISERLNTVTVENDLLKYIKNKIPVQGRLG

NFKLDTAEFEKKLNTILFVLNESNLAQRFSILVRKHYLKERPIDPIYVNILDDN

SYSTLEGFNISSQGSNDFQGQLLESSYFEKIESNALRAFIKICPRNGLLYNAIYR

NSKNYLNNIDLEDKKTTSKTNVSYPCSLLNGCIEVENKDLFLISNKDSLNDINL

SEEKIKPETTVFFKDKLPPQDITLSNYDFTEANSIPSISQQNILERNEELYEPIRN

SLFEIKTIYVDKLTTFHFLEAQNIDESIDSSKIRVELTDSVDEALSNPNKVYSPF

KNMSNTINSIETGITSTYIFYQWLRSIVKDFSDETGKIDVIDKSSDTLAIVPYIGP

LLNIGNDIRHGDFVGAIELAGITALLEYVPEFTIPILVGLEVIGGELAREQVEAI

VNNALDKRDQKWAEVYNITKAQWWGTIHLQINTRLAHTYKALSRQANAIK

MNMEFQLANYKGNIDDKAKIKNAISETEILLNKSVEQAMKNTEKFMIKLSNS

YLTKEMIPKVQDNLKNFDLETKKTLDKFIKEKEDILGTNLSSSLRRKVSIRLNK

NIAFDINDIPFSEFDDLINQYKNEIEDYEVLNLGAEDGKIKDLSGTTSDINIGSDI

ELADGRENKAIKIKGSENSTIKIAMNKYLRFSATDNFSISFWIKHPKPTNLLNN

GIEYTLVENFNQRGWKISIQDSKLIWYLRDHNNSIKIVTPDYIAFNGWNLITIT

NNRSKGSIVYVNGSKIEEKDISSIWNTEVDDPIIFRLKNNRDTQAFTLLDQFSIY

RKELNQNEVVKLYNYYFNSNYIRDIWGNPLQYNKKYYLQTQDKPGKGLIRE

YWSSFGYDYVILSDSKTITFPNNIRYGALYNGSKVLIKNSKKLDGLVRNKDFI

QLEIDGYNMGISADRFNEDTNYIGTTYGTTHDLTTDFEIIQRQEKYRNYCQLK

TPYNIFHKSGLMSTETSKPTFHDYRDWVYSSAWYFQNYENLNLRKHTKTNW

YFIPKDEGWDED

-VAMP4_Rat (D4A560)
SEQ ID NO: 42
MPPKFKRHLNDDDVTGSVKSERRNLLEDDSDEEEDFFLRGPSGPRFGPRNDKI

KHVQNQVDEVIDVMQENITKVIERGERLDELQDKSESLSDNATAFSNRSKQLR

RQMWWRGCKIKAIMALAAAILLLMIITQIILHLKK

-VAMP4_human (O75379)
SEQ ID NO: 43
MPPKFKRHLNDDDVTGSVKSERRNLLEDDSDEEEDFFLRGPSGPRFGPRNDKI

KHVQNQVDEVIDVMQENITKVIERGERLDELQDKSESLSDNATAFSNRSKQLR

RQMWWRGCKIKAIMALVAAILLLVIIILIVMKYRT

-VAMP8_Rat (Q9Z2J5)
SEQ ID NO: 44
MAGKELERCQRQADQVTEIMLNNFDKVLERDGKLSELQQRSDQLLDMSSAFS
KTTKTLAQQKRWENIRCRVYLGLAVAGGLLLILVVLLVIFLPSGEDSSKP

-VAMP8_human (O95183)
SEQ ID NO: 45
MAGIELERCQQQANEVTEIMRNNFGKVLERGVKLAELQQRSDQLLDMSSTFN
KTTQNLAQKKCWENIRYRICVGLVVVGVLLIILIVLLVVFLPQSSDSSSAPRTQ
DAGIASGPGN -YKT6_Rat (Q5EGY4)
SEQ ID NO: 46
MKLYSLSVFYKGEPKAVLLKAAYDVSSFSFFQRSSVQEFMTFTSQLIVERSAK
GSRASVKEQEYLCHVYVRSDSLAGVVIADSEYPSRVAFTLLEKVLDEFSKQVD
RIDWPVGSPATIHYTALDGHLSRYQNPREADPMSKVQAELDETKIILHNTMES
LLERGEKLDDLVSKSEVLGTQSKAFYKTARKQNSCCAIM -YKT6_human (O15498)
SEQ ID NO: 47
MKLYSLSVLYKGEAKVVLLKAAYDVSSFSFFQRSSVQEFMTFTSQLIVERSSK
GTRASVKEQDYLCHVYVRNDSLAGVVIADNEYPSRVAFTLLEKVLDEFSKQV
DRIDWPVGSPATIHYPALDGHLSRYQNPREADPMTKVQAELDETKIILHNTME
SLLERGEKLDDLVSKSEVLGTQSKAFYKTARKQNSCCAIM -VAMP epitope
SEQ ID NO: 48
ETSAAKLKRKYWWK -VAMP epitope
SEQ ID NO: 49
FETSAAKLKRKYWWK -VAMP epitope
SEQ ID NO: 50
QFESSAAKLKRKYW -VAMP epitope
SEQ ID NO: 51
FESSAAKLKR -VAMP epitope
SEQ ID NO: 52
FESSAAKLKRKYWWK -VAMP epitope
SEQ ID NO: 53
ADALQAGASQF -VAMP epitope
SEQ ID NO: 54
ADALQAGASQ -VAMP epitope
SEQ ID NO: 55
RADALQAGASQF -VAMP epitope
SEQ ID NO: 56
ADALQAGASQFE -VAMP epitope
SEQ ID NO: 57
ADALQAGASVF -VAMP epitope
SEQ ID NO: 58
ADALQAGASV -continued -VAMP epitope
ADALQAGASVFE                                    SEQ ID NO: 59

-VAMP epitope
RADALQAGASVF                                    SEQ ID NO: 60

-VAMP epitope
RADALQAGAS                                      SEQ ID NO: 61

-VAMP epitope
SESLSDNATAF                                     SEQ ID NO: 62

-VAMP epitope
SESLSDNATA                                      SEQ ID NO: 63

-VAMP epitope
KSESLSDNATAF                                    SEQ ID NO: 64

-VAMP epitope
SESLSDNATAFS                                    SEQ ID NO: 65

-VAMP epitope
SDQLLDMSSTF                                     SEQ ID NO: 66

-VAMP epitope
SDQLLDMSST                                      SEQ ID NO: 67

-VAMP epitope
RSDQLLDMSSTF                                    SEQ ID NO: 68

-VAMP epitope
SDQLLDMSSTFN                                    SEQ ID NO: 69

-VAMP epitope
SDQLLDMSSAF                                     SEQ ID NO: 70

-VAMP epitope
SDQLLDMSSA                                      SEQ ID NO: 71

-VAMP epitope
RSDQLLDMSSAF                                    SEQ ID NO: 72

-VAMP epitope
SDQLLDMSSAFS                                    SEQ ID NO: 73

-VAMP epitope
RSDQLLDMSS                                      SEQ ID NO: 74

-VAMP epitope
SEVLGTQSKAF                                     SEQ ID NO: 75

-VAMP epitope
SEVLGTQSKA                                      SEQ ID NO: 76

-VAMP epitope
KSEVLGTQSKAF                                    SEQ ID NO: 77

-VAMP epitope
SEVLGTQSKAFY                                    SEQ ID NO: 78

The invention claimed is:

1. An antigenic polypeptide consisting of 16 to 65 amino acid residues, the polypeptide comprising an amino acid sequence that is at least 90% identical to the amino acid sequence of any one of SEQ ID NOs: 22-3o and 48-78, wherein the antigenic polypeptide shares no more than 15 consecutive amino acid residues in common with a naturally-occurring VAMP amino acid sequence.

2. The antigenic polypeptide of claim 1, wherein the polypeptide consists of 16 or 17 amino acid residues.

3. An antigenic protein comprising a polypeptide covalently linked to a carrier, wherein the polypeptide:
consists of 16 to 65 amino acid residues;
comprises a VAMP epitope comprising an amino acid sequence that is at least 90% identical to the amino acid sequence of any one of SEO ID NOs: 15-34 and 48-78; and shares no more than 15 consecutive amino acid residues in common with a naturally-occurring VAMP amino acid sequence.

4. A method of generating an antibody against a C-terminal VAMP cleavage product, the method comprising using a polypeptide that:
consists of 16 to 65 amino acid residues;
comprises a VAMP epitope comprising an amino acid sequence that is at least 90% identical to the amino acid sequence of any one of SEQ ID NOs: 15-34 and 48-78; and shares no more than 15 consecutive amino acid residues in common with a naturally-occurring VAMP amino acid sequence;
the method comprising immunizing an animal or an egg with the polypeptide; or the method comprising immunizing a lymphocyte in vitro with the polypeptide.

5. An antigenic protein comprising an antigenic polypeptide covalently linked to a carrier, the antigenic polypeptide consisting of 10 to 3o amino acid residues and comprising a VAMP epitope comprising an amino acid sequence that is at least 90% identical to the amino acid sequence of any one of SEQ ID NOs: 1S-24 and 48-78.

6. The polypeptide of claim 1, comprising an amino acid sequence that is at least 90% identical to the amino acid sequence of any one of SEQ ID NOs: 53-78.

7. The polypeptide of claim 1, comprising an amino acid sequence that is at least 90% identical to the amino acid sequence of any one of SEQ ID NOs: 62, 66, and 75.

8. The antigenic protein of claim 3, wherein the VAMP is $VAMP_1$, $VAMP_2$, $VAMP_3$, $VAMP_4$, $VAMP_5$ or YKT6.

9. The antigenic protein of claim 3, wherein the VAMP epitope comprises an amino acid sequence that is at least 90% identical to the amino acid sequence of any one of SEQ ID NOs: 15, 22, 27, 32, 49, and 53.

10. The antigenic protein of claim 3, wherein the VAMP epitope comprises an amino acid sequence that is at least 90% identical to the amino acid sequence of any one of SEQ ID NOs: 22-30 and 48-78.

11. The antigenic protein of claim 3, wherein the VAMP epitope comprises an amino acid sequence that is at least 90% identical to the amino acid sequence of any one of SEQ ID NOs: 53-78.

12. The antigenic protein of claim 3, wherein the VAMP epitope comprises an amino acid sequence that is at least 90% identical to the amino acid sequence of any one of SEQ ID NOs: 62, 66, and 75.

13. The method of claim 4, wherein the VAMP is $VAMP_1$, $VAMP_2$, $VAMP_3$, $VAMP_4$, $VAMP_5$ or YKT6.

14. The method of claim 4, wherein the VAMP epitope comprises an amino acid sequence that is at least 90% identical to the amino acid sequence of any one of SEQ ID NOs: 15, 22, 27, 32, 49, and 53.

15. The method of claim 4, wherein the VAMP epitope comprises an amino acid sequence that is at least 90% identical to the amino acid sequence of any one of SEQ ID NOs: 22-30 and 48-78.

16. The method of claim 4, wherein the VAMP epitope comprises an amino acid sequence that is at least 90% identical to the amino acid sequence of any one of SEQ ID NOs: 53-78.

17. The method of claim 4, wherein the VAMP epitope comprises an amino acid sequence that is at least 90% identical to the amino acid sequence of any one of SEQ ID NOs: 62, 66, and 75.

* * * * *

SEQUENCE LISTING

<160> NUMBER OF SEQ ID NOS: 78

<210> SEQ ID NO 1
<211> LENGTH: 1296
<212> TYPE: PRT
<213> ORGANISM: Clostridium botulinum

<400> SEQUENCE: 1

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
                20                  25                  30

Val Lys Ala Phe Lys Ile His Asn Lys Ile Trp Val Ile Pro Glu Arg
            35                  40                  45

Asp Thr Phe Thr Asn Pro Glu Glu Gly Asp Leu Asn Pro Pro Pro Glu
        50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
        130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
        210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
        290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
            355                 360                 365
```

-continued

```
Phe Asp Lys Ala Val Phe Lys Ile Asn Ile Val Pro Lys Val Asn Tyr
    370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Asp Lys Gly Tyr Asn Lys
        435                 440                 445
Ala Leu Asn Asp Leu Cys Ile Lys Val Asn Asn Trp Asp Leu Phe Phe
450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
        515                 520                 525
Glu Leu Met Pro Asn Ile Glu Arg Phe Pro Asn Gly Lys Lys Tyr Glu
530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
                565                 570                 575
Leu Asn Pro Ser Arg Val Tyr Thr Phe Phe Ser Ser Asp Tyr Val Lys
            580                 585                 590
Lys Val Asn Lys Ala Thr Glu Ala Ala Met Phe Leu Gly Trp Val Glu
        595                 600                 605
Gln Leu Val Tyr Asp Phe Thr Asp Glu Thr Ser Glu Val Ser Thr Thr
610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
            660                 665                 670
Ile Pro Val Leu Gly Thr Phe Ala Leu Val Ser Tyr Ile Ala Asn Lys
        675                 680                 685
Val Leu Thr Val Gln Thr Ile Asp Asn Ala Leu Ser Lys Arg Asn Glu
690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Lys Met Lys Glu Ala Leu
                725                 730                 735
Glu Asn Gln Ala Glu Ala Thr Lys Ala Ile Ile Asn Tyr Gln Tyr Asn
            740                 745                 750
Gln Tyr Thr Glu Glu Lys Asn Asn Ile Asn Phe Asn Ile Asp Asp
        755                 760                 765
Leu Ser Ser Lys Leu Asn Glu Ser Ile Asn Lys Ala Met Ile Asn Ile
770                 775                 780
Asn Lys Phe Leu Asn Gln Cys Ser Val Ser Tyr Leu Met Asn Ser Met
```

-continued

```
                785                 790                 795                 800
Ile Pro Tyr Gly Val Lys Arg Leu Glu Asp Phe Asp Ala Ser Leu Lys
                    805                 810                 815

Asp Ala Leu Leu Lys Tyr Ile Tyr Asp Asn Arg Gly Thr Leu Ile Gly
                    820                 825                 830

Gln Val Asp Arg Leu Lys Asp Lys Val Asn Asn Thr Leu Ser Thr Asp
                    835                 840                 845

Ile Pro Phe Gln Leu Ser Lys Tyr Val Asp Asn Gln Arg Leu Leu Ser
                    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                    885                 890                 895

Lys Ile Asn Ile Gly Ser Lys Val Asn Phe Asp Pro Ile Asp Lys Asn
                    900                 905                 910

Gln Ile Gln Leu Phe Asn Leu Glu Ser Ser Lys Ile Glu Val Ile Leu
                    915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                    965                 970                 975

Ser Leu Asn Tyr Gly Glu Ile Ile Trp Thr Leu Gln Asp Thr Gln Glu
                    980                 985                 990

Ile Lys Gln Arg Val Val Phe Lys Tyr Ser Gln Met Ile Asn Ile Ser
                    995                 1000                1005

Asp Tyr Ile Asn Arg Trp Ile Phe Val Thr Ile Thr Asn Asn Arg
            1010                1015                1020

Leu Asn Asn Ser Lys Ile Tyr Ile Asn Gly Arg Leu Ile Asp Gln
            1025                1030                1035

Lys Pro Ile Ser Asn Leu Gly Asn Ile His Ala Ser Asn Asn Ile
            1040                1045                1050

Met Phe Lys Leu Asp Gly Cys Arg Asp Thr His Arg Tyr Ile Trp
            1055                1060                1065

Ile Lys Tyr Phe Asn Leu Phe Asp Lys Glu Leu Asn Glu Lys Glu
            1070                1075                1080

Ile Lys Asp Leu Tyr Asp Asn Gln Ser Asn Ser Gly Ile Leu Lys
            1085                1090                1095

Asp Phe Trp Gly Asp Tyr Leu Gln Tyr Asp Lys Pro Tyr Tyr Met
            1100                1105                1110

Leu Asn Leu Tyr Asp Pro Asn Lys Tyr Val Asp Val Asn Asn Val
            1115                1120                1125

Gly Ile Arg Gly Tyr Met Tyr Leu Lys Gly Pro Arg Gly Ser Val
            1130                1135                1140

Met Thr Thr Asn Ile Tyr Leu Asn Ser Ser Leu Tyr Arg Gly Thr
            1145                1150                1155

Lys Phe Ile Ile Lys Lys Tyr Ala Ser Gly Asn Lys Asp Asn Ile
            1160                1165                1170

Val Arg Asn Asn Asp Arg Val Tyr Ile Asn Val Val Val Lys Asn
            1175                1180                1185

Lys Glu Tyr Arg Leu Ala Thr Asn Ala Ser Gln Ala Gly Val Glu
            1190                1195                1200
```

```
Lys Ile Leu Ser Ala Leu Glu Ile Pro Asp Val Gly Asn Leu Ser
    1205                1210                1215

Gln Val Val Met Lys Ser Lys Asn Asp Gln Gly Ile Thr Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295

<210> SEQ ID NO 2
<211> LENGTH: 1291
<212> TYPE: PRT
<213> ORGANISM: Clostridium botulinum

<400> SEQUENCE: 2

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
```

```
                260                 265                 270
Gly Gly Gln Asp Pro Ser Ile Ile Thr Pro Ser Thr Asp Lys Ser Ile
            275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
            325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
            370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
            530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
            610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
            675                 680                 685
```

-continued

Arg Asn Glu Lys Trp Ser Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
            725                 730                 735

Arg Tyr Asn Ile Tyr Ser Glu Lys Lys Ser Asn Ile Asn Ile Asp
            740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Gly Cys Ser Val Ser Tyr Leu Met
770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
            805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
            835                 840                 845

Leu Ile Glu Met Phe Asn Lys Tyr Asn Ser Glu Ile Leu Asn Asn Ile
850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
            885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
            915                 920                 925

Ser Phe Trp Ile Arg Ile Pro Lys Tyr Lys Asn Asp Gly Ile Gln Asn
930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
            965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
            995                 1000                1005

Asn Asn Leu Asn Asn Ala Lys Ile Tyr Ile Asn Gly Lys Leu Glu
    1010                1015                1020

Ser Asn Thr Asp Ile Lys Asp Ile Arg Glu Val Ile Ala Asn Gly
    1025                1030                1035

Glu Ile Ile Phe Lys Leu Asp Gly Asp Ile Asp Arg Thr Gln Phe
    1040                1045                1050

Ile Trp Met Lys Tyr Phe Ser Ile Phe Asn Thr Glu Leu Ser Gln
    1055                1060                1065

Ser Asn Ile Glu Glu Arg Tyr Lys Ile Gln Ser Tyr Ser Glu Tyr
    1070                1075                1080

Leu Lys Asp Phe Trp Gly Asn Pro Leu Met Tyr Asn Lys Glu Tyr
    1085                1090                1095

Tyr Met Phe Asn Ala Gly Asn Lys Asn Ser Tyr Ile Lys Leu Lys
1100             1105                 1110

Lys Asp Ser Pro Val Gly Glu Ile Leu Thr Arg Ser Lys Tyr Asn
1115             1120                 1125

Gln Asn Ser Lys Tyr Ile Asn Tyr Arg Asp Leu Tyr Ile Gly Glu
1130             1135                 1140

Lys Phe Ile Ile Arg Arg Lys Ser Asn Ser Gln Ser Ile Asn Asp
1145             1150                 1155

Asp Ile Val Arg Lys Glu Asp Tyr Ile Tyr Leu Asp Phe Phe Asn
1160             1165                 1170

Leu Asn Gln Glu Trp Arg Val Tyr Thr Tyr Lys Tyr Phe Lys Lys
1175             1180                 1185

Glu Glu Glu Lys Leu Phe Leu Ala Pro Ile Ser Asp Ser Asp Glu
1190             1195                 1200

Phe Tyr Asn Thr Ile Gln Ile Lys Glu Tyr Asp Glu Gln Pro Thr
1205             1210                 1215

Tyr Ser Cys Gln Leu Leu Phe Lys Lys Asp Glu Glu Ser Thr Asp
1220             1225                 1230

Glu Ile Gly Leu Ile Gly Ile His Arg Phe Tyr Glu Ser Gly Ile
1235             1240                 1245

Val Phe Glu Glu Tyr Lys Asp Tyr Phe Cys Ile Ser Lys Trp Tyr
1250             1255                 1260

Leu Lys Glu Val Lys Arg Lys Pro Tyr Asn Leu Lys Leu Gly Cys
1265             1270                 1275

Asn Trp Gln Phe Ile Pro Lys Asp Glu Gly Trp Thr Glu
1280             1285                 1290

<210> SEQ ID NO 3
<211> LENGTH: 1291
<212> TYPE: PRT
<213> ORGANISM: Clostridium botulinum

<400> SEQUENCE: 3

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
                20                  25                  30

Pro Glu Lys Ala Phe Arg Ile Thr Gly Asn Ile Trp Val Ile Pro Asp
            35                  40                  45

Arg Phe Ser Arg Asn Ser Asn Pro Asn Leu Asn Lys Pro Pro Arg Val
        50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

```
Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
            275                 280                 285

Phe Glu Glu Lys Ala Leu Asp Tyr Tyr Arg Ser Ile Ala Lys Arg Leu
        290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590
```

-continued

Val Gln Gly Gly Leu Phe Leu Met Trp Ala Asn Asp Val Glu Asp
            595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
            645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
            675                 680                 685

Thr Ile Asp Asn Cys Leu Glu Gln Arg Ile Lys Arg Trp Lys Asp Ser
            690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
            725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
            755                 760                 765

Asp Val Lys Ile Ser Glu Ala Met Asn Asn Ile Asn Lys Phe Ile Arg
            770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
            805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
            835                 840                 845

Phe Ser Tyr Thr Asn Asn Ser Leu Leu Lys Asp Ile Ile Asn Glu Tyr
850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
            885                 890                 895

Gly Asp Val Gln Leu Asn Pro Ile Phe Pro Phe Asp Phe Lys Leu Gly
            900                 905                 910

Ser Ser Gly Glu Asp Arg Gly Lys Val Ile Val Thr Gln Asn Glu Asn
            915                 920                 925

Ile Val Tyr Asn Ser Met Tyr Glu Ser Phe Ser Ile Ser Phe Trp Ile
            930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
            965                 970                 975

Leu Val Phe Thr Leu Lys Gln Asn Glu Asp Ser Glu Gln Ser Ile Asn
            980                 985                 990

Phe Ser Tyr Asp Ile Ser Asn Asn Ala Pro Gly Tyr Asn Lys Trp Phe
            995                 1000                1005

Phe Val Thr Val Thr Asn Asn Met Met Gly Asn Met Lys Ile Tyr

-continued

```
                   1010                1015                1020

Ile Asn Gly Lys Leu Ile Asp Thr Ile Lys Val Lys Glu Leu Thr
            1025                1030                1035

Gly Ile Asn Phe Ser Lys Thr Ile Thr Phe Glu Ile Asn Lys Ile
        1040                1045                1050

Pro Asp Thr Gly Leu Ile Thr Ser Asp Ser Asp Asn Ile Asn Met
    1055                1060                1065

Trp Ile Arg Asp Phe Tyr Ile Phe Ala Lys Glu Leu Asp Gly Lys
1070                1075                1080

Asp Ile Asn Ile Leu Phe Asn Ser Leu Gln Tyr Thr Asn Val Val
        1085                1090                1095

Lys Asp Tyr Trp Gly Asn Asp Leu Arg Tyr Asn Lys Glu Tyr Tyr
    1100                1105                1110

Met Val Asn Ile Asp Tyr Leu Asn Arg Tyr Met Tyr Ala Asn Ser
1115                1120                1125

Arg Gln Ile Val Phe Asn Thr Arg Arg Asn Asn Asn Asp Phe Asn
        1130                1135                1140

Glu Gly Tyr Lys Ile Ile Ile Lys Arg Ile Arg Gly Asn Thr Asn
    1145                1150                1155

Asp Thr Arg Val Arg Gly Gly Asp Ile Leu Tyr Phe Asp Met Thr
1160                1165                1170

Ile Asn Asn Lys Ala Tyr Asn Leu Phe Met Lys Asn Glu Thr Met
        1175                1180                1185

Tyr Ala Asp Asn His Ser Thr Glu Asp Ile Tyr Ala Ile Gly Leu
    1190                1195                1200

Arg Glu Gln Thr Lys Asp Ile Asn Asp Asn Ile Ile Phe Gln Ile
1205                1210                1215

Gln Pro Met Asn Asn Thr Tyr Tyr Tyr Ala Ser Gln Ile Phe Lys
        1220                1225                1230

Ser Asn Phe Asn Gly Glu Asn Ile Ser Gly Ile Cys Ser Ile Gly
    1235                1240                1245

Thr Tyr Arg Phe Arg Leu Gly Gly Asp Trp Tyr Arg His Asn Tyr
1250                1255                1260

Leu Val Pro Thr Val Lys Gln Gly Asn Tyr Ala Ser Leu Leu Glu
        1265                1270                1275

Ser Thr Ser Thr His Trp Gly Phe Val Pro Val Ser Glu
    1280                1285                1290

<210> SEQ ID NO 4
<211> LENGTH: 1276
<212> TYPE: PRT
<213> ORGANISM: Clostridium botulinum

<400> SEQUENCE: 4

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80
```

-continued

```
Glu Gln Lys Asp Thr Phe Leu Lys Gly Ile Lys Leu Phe Lys Arg
                85              90              95

Ile Asn Glu Arg Asp Ile Gly Lys Lys Leu Ile Asn Tyr Leu Val Val
            100             105             110

Gly Ser Pro Phe Met Gly Asp Ser Ser Thr Pro Glu Asp Thr Phe Asp
            115             120             125

Phe Thr Arg His Thr Thr Asn Ile Ala Val Glu Lys Phe Glu Asn Gly
            130             135             140

Ser Trp Lys Val Thr Asn Ile Ile Thr Pro Ser Val Leu Ile Phe Gly
145             150             155             160

Pro Leu Pro Asn Ile Leu Asp Tyr Thr Ala Ser Leu Thr Leu Gln Gly
                165             170             175

Gln Gln Ser Asn Pro Ser Phe Glu Gly Phe Gly Thr Leu Ser Ile Leu
            180             185             190

Lys Val Ala Pro Glu Phe Leu Leu Thr Phe Ser Asp Val Thr Ser Asn
            195             200             205

Gln Ser Ser Ala Val Leu Gly Lys Ser Ile Phe Cys Met Asp Pro Val
210             215             220

Ile Ala Leu Met His Glu Leu Thr His Ser Leu His Gln Leu Tyr Gly
225             230             235             240

Ile Asn Ile Pro Ser Asp Lys Arg Ile Arg Pro Gln Val Ser Glu Gly
                245             250             255

Phe Phe Ser Gln Asp Gly Pro Asn Val Gln Phe Glu Glu Leu Tyr Thr
            260             265             270

Phe Gly Gly Leu Asp Val Glu Ile Ile Pro Gln Ile Glu Arg Ser Gln
            275             280             285

Leu Arg Glu Lys Ala Leu Gly His Tyr Lys Asp Ile Ala Lys Arg Leu
            290             295             300

Asn Asn Ile Asn Lys Thr Ile Pro Ser Ser Trp Ile Ser Asn Ile Asp
305             310             315             320

Lys Tyr Lys Lys Ile Phe Ser Glu Lys Tyr Asn Phe Asp Lys Asp Asn
                325             330             335

Thr Gly Asn Phe Val Val Asn Ile Asp Lys Phe Asn Ser Leu Tyr Ser
            340             345             350

Asp Leu Thr Asn Val Met Ser Glu Val Val Tyr Ser Ser Gln Tyr Asn
            355             360             365

Val Lys Asn Arg Thr His Tyr Phe Ser Arg His Tyr Leu Pro Val Phe
            370             375             380

Ala Asn Ile Leu Asp Asp Asn Ile Tyr Thr Ile Arg Asp Gly Phe Asn
385             390             395             400

Leu Thr Asn Lys Gly Phe Asn Ile Glu Asn Ser Gly Gln Asn Ile Glu
                405             410             415

Arg Asn Pro Ala Leu Gln Lys Leu Ser Ser Glu Ser Val Val Asp Leu
            420             425             430

Phe Thr Lys Val Cys Leu Arg Leu Thr Lys Asn Ser Arg Asp Asp Ser
            435             440             445

Thr Cys Ile Lys Val Lys Asn Asn Arg Leu Pro Tyr Val Ala Asp Lys
450             455             460

Asp Ser Ile Ser Gln Glu Ile Phe Glu Asn Lys Ile Ile Thr Asp Glu
465             470             475             480

Thr Asn Val Gln Asn Tyr Ser Asp Lys Phe Ser Leu Asp Glu Ser Ile
                485             490             495

Leu Asp Gly Gln Val Pro Ile Asn Pro Glu Ile Val Asp Pro Leu Leu
```

```
            500                 505                 510
Pro Asn Val Asn Met Glu Pro Leu Asn Leu Pro Gly Glu Glu Ile Val
    515                 520                 525
Phe Tyr Asp Asp Ile Thr Lys Tyr Val Asp Tyr Leu Asn Ser Tyr Tyr
    530                 535                 540
Tyr Leu Glu Ser Gln Lys Leu Ser Asn Asn Val Glu Asn Ile Thr Leu
545                 550                 555                 560
Thr Thr Ser Val Glu Glu Ala Leu Gly Tyr Ser Asn Lys Ile Tyr Thr
                565                 570                 575
Phe Leu Pro Ser Leu Ala Glu Lys Val Asn Lys Gly Val Gln Ala Gly
                580                 585                 590
Leu Phe Leu Asn Trp Ala Asn Glu Val Val Glu Asp Phe Thr Thr Asn
                595                 600                 605
Ile Met Lys Lys Asp Thr Leu Asp Lys Ile Ser Asp Val Ser Val Ile
            610                 615                 620
Ile Pro Tyr Ile Gly Pro Ala Leu Asn Ile Gly Asn Ser Ala Leu Arg
625                 630                 635                 640
Gly Asn Phe Asn Gln Ala Phe Ala Thr Ala Gly Val Ala Phe Leu Leu
                645                 650                 655
Glu Gly Phe Pro Glu Phe Thr Ile Pro Ala Leu Gly Val Phe Thr Phe
                660                 665                 670
Tyr Ser Ser Ile Gln Glu Arg Glu Lys Ile Ile Lys Thr Ile Glu Asn
                675                 680                 685
Cys Leu Glu Gln Arg Val Lys Arg Trp Lys Asp Ser Tyr Gln Trp Met
            690                 695                 700
Val Ser Asn Trp Leu Ser Arg Ile Thr Thr Gln Phe Asn His Ile Asn
705                 710                 715                 720
Tyr Gln Met Tyr Asp Ser Leu Ser Tyr Gln Ala Asp Ala Ile Lys Ala
                725                 730                 735
Lys Ile Asp Leu Glu Tyr Lys Lys Tyr Ser Gly Ser Asp Lys Glu Asn
                740                 745                 750
Ile Lys Ser Gln Val Glu Asn Leu Lys Asn Ser Leu Asp Val Lys Ile
            755                 760                 765
Ser Glu Ala Met Asn Asn Ile Asn Lys Phe Ile Arg Glu Cys Ser Val
    770                 775                 780
Thr Tyr Leu Phe Lys Asn Met Leu Pro Lys Val Ile Asp Glu Leu Asn
785                 790                 795                 800
Lys Phe Asp Leu Arg Thr Lys Thr Glu Leu Ile Asn Leu Ile Asp Ser
                805                 810                 815
His Asn Ile Ile Leu Val Gly Glu Val Asp Arg Leu Lys Ala Lys Val
            820                 825                 830
Asn Glu Ser Phe Glu Asn Thr Met Pro Phe Asn Ile Phe Ser Tyr Thr
            835                 840                 845
Asn Asn Ser Leu Leu Lys Asp Ile Ile Asn Glu Tyr Phe Asn Ser Ile
            850                 855                 860
Asn Asp Ser Lys Ile Leu Ser Leu Gln Asn Lys Lys Asn Ala Leu Val
865                 870                 875                 880
Asp Thr Ser Gly Tyr Asn Ala Glu Val Arg Val Gly Asp Asn Val Gln
                885                 890                 895
Leu Asn Thr Ile Tyr Thr Asn Asp Phe Lys Leu Ser Ser Ser Gly Asp
                900                 905                 910
Lys Ile Ile Val Asn Leu Asn Asn Asn Ile Leu Tyr Ser Ala Ile Tyr
            915                 920                 925
```

```
Glu Asn Ser Ser Val Ser Phe Trp Ile Lys Ile Ser Lys Asp Leu Thr
            930                 935                 940
Asn Ser His Asn Glu Tyr Thr Ile Ile Asn Ser Ile Glu Gln Asn Ser
945                 950                 955                 960
Gly Trp Lys Leu Cys Ile Arg Asn Gly Asn Ile Glu Trp Ile Leu Gln
                965                 970                 975
Asp Val Asn Arg Lys Tyr Lys Ser Leu Ile Phe Asp Tyr Ser Glu Ser
                980                 985                 990
Leu Ser His Thr Gly Tyr Thr Asn Lys Trp Phe Phe Val Thr Ile Thr
        995                 1000                1005
Asn Asn Ile Met Gly Tyr Met Lys Leu Tyr Ile Asn Gly Glu Leu
    1010                1015                1020
Lys Gln Ser Gln Lys Ile Glu Asp Leu Asp Glu Val Lys Leu Asp
    1025                1030                1035
Lys Thr Ile Val Phe Gly Ile Asp Glu Asn Ile Asp Glu Asn Gln
    1040                1045                1050
Met Leu Trp Ile Arg Asp Phe Asn Ile Phe Ser Lys Glu Leu Ser
    1055                1060                1065
Asn Glu Asp Ile Asn Ile Val Tyr Glu Gly Gln Ile Leu Arg Asn
    1070                1075                1080
Val Ile Lys Asp Tyr Trp Gly Asn Pro Leu Lys Phe Asp Thr Glu
    1085                1090                1095
Tyr Tyr Ile Ile Asn Asp Asn Tyr Ile Asp Arg Tyr Ile Ala Pro
    1100                1105                1110
Glu Ser Asn Val Leu Val Leu Val Gln Tyr Pro Asp Arg Ser Lys
    1115                1120                1125
Leu Tyr Thr Gly Asn Pro Ile Thr Ile Lys Ser Val Ser Asp Lys
    1130                1135                1140
Asn Pro Tyr Ser Arg Ile Leu Asn Gly Asp Asn Ile Ile Leu His
    1145                1150                1155
Met Leu Tyr Asn Ser Arg Lys Tyr Met Ile Ile Arg Asp Thr Asp
    1160                1165                1170
Thr Ile Tyr Ala Thr Gln Gly Gly Glu Cys Ser Gln Asn Cys Val
    1175                1180                1185
Tyr Ala Leu Lys Leu Gln Ser Asn Leu Gly Asn Tyr Gly Ile Gly
    1190                1195                1200
Ile Phe Ser Ile Lys Asn Ile Val Ser Lys Asn Lys Tyr Cys Ser
    1205                1210                1215
Gln Ile Phe Ser Ser Phe Arg Glu Asn Thr Met Leu Leu Ala Asp
    1220                1225                1230
Ile Tyr Lys Pro Trp Arg Phe Ser Phe Lys Asn Ala Tyr Thr Pro
    1235                1240                1245
Val Ala Val Thr Asn Tyr Glu Thr Lys Leu Leu Ser Thr Ser Ser
    1250                1255                1260
Phe Trp Lys Phe Ile Ser Arg Asp Pro Gly Trp Val Glu
    1265                1270                1275

<210> SEQ ID NO 5
<211> LENGTH: 1252
<212> TYPE: PRT
<213> ORGANISM: Clostridium botulinum

<400> SEQUENCE: 5

Met Pro Lys Ile Asn Ser Phe Asn Tyr Asn Asp Pro Val Asn Asp Arg
```

-continued

```
  1               5                  10                 15
Thr Ile Leu Tyr Ile Lys Pro Gly Gly Cys Gln Glu Phe Tyr Lys Ser
         20                  25                 30

Phe Asn Ile Met Lys Asn Ile Trp Ile Ile Pro Glu Arg Asn Val Ile
         35                  40                 45

Gly Thr Thr Pro Gln Asp Phe His Pro Pro Thr Ser Leu Lys Asn Gly
         50                  55                 60

Asp Ser Ser Tyr Tyr Asp Pro Asn Tyr Leu Gln Ser Asp Glu Glu Lys
 65                  70                  75                 80

Asp Arg Phe Leu Lys Ile Val Thr Lys Ile Phe Asn Arg Ile Asn Asn
                 85                  90                 95

Asn Leu Ser Gly Gly Ile Leu Leu Glu Glu Leu Ser Lys Ala Asn Pro
                100                 105                110

Tyr Leu Gly Asn Asp Asn Thr Pro Asp Asn Gln Phe His Ile Gly Asp
                115                 120                125

Ala Ser Ala Val Glu Ile Lys Phe Ser Asn Gly Ser Gln Asp Ile Leu
        130                 135                 140

Leu Pro Asn Val Ile Ile Met Gly Ala Glu Pro Asp Leu Phe Glu Thr
145                 150                 155                160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Gly Tyr Ser Phe
                180                 185                 190

Arg Phe Asn Asp Asn Ser Met Asn Glu Phe Ile Gln Asp Pro Ala Leu
                195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
                260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
        290                 295                 300

Ala Lys Tyr Gly Leu Asp Lys Asp Ala Ser Gly Ile Tyr Ser Val Asn
305                 310                 315                320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
                355                 360                 365

Tyr Asn Ile Ser Glu Gly Tyr Asn Ile Asn Asn Leu Lys Val Asn Phe
        370                 375                 380

Arg Gly Gln Asn Ala Asn Leu Asn Pro Arg Ile Ile Thr Pro Ile Thr
385                 390                 395                400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
                420                 425                 430
```

```
Glu Leu Phe Phe Val Ala Ser Glu Asn Ser Tyr Asn Asp Asp Asn Ile
            435                 440                 445

Asn Thr Pro Lys Glu Ile Asp Asp Thr Val Thr Ser Asn Asn Asn Tyr
450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
            515                 520                 525

Pro Glu Gly Glu Asn Asn Val Asn Leu Thr Ser Ser Ile Asp Thr Ala
            530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Pro Tyr Ile Gly Leu
            595                 600                 605

Ala Leu Asn Ile Gly Asn Glu Ala Gln Lys Gly Asn Phe Lys Asp Ala
            610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
            675                 680                 685

Trp Met Thr Lys Ile Asn Thr Gln Phe Asn Lys Arg Lys Glu Gln Met
            690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
            755                 760                 765

Tyr Leu Met Lys Leu Ile Asn Glu Val Lys Ile Asn Lys Leu Arg Glu
            770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Lys Arg Ile Lys
            835                 840                 845
```

```
Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu  Gly Asp Ser Lys Leu  Tyr Ile Asn
        995                 1000                1005

Gly Asn  Leu Ile Asp Gln  Lys  Ser Ile Leu Asn Leu  Gly Asn Ile
    1010                 1015                1020

His Val  Ser Asp Asn Ile  Leu  Phe Lys Ile Val Asn  Cys Ser Tyr
    1025                 1030                1035

Thr Arg  Tyr Ile Gly Ile  Arg  Tyr Phe Asn Ile Phe  Asp Lys Glu
    1040                 1045                1050

Leu Asp  Glu Thr Glu Ile  Gln  Thr Leu Tyr Ser Asn  Glu Pro Asn
    1055                 1060                1065

Thr Asn  Ile Leu Lys Asp  Phe  Trp Gly Asn Tyr Leu  Leu Tyr Asp
    1070                 1075                1080

Lys Glu  Tyr Tyr Leu Leu  Asn  Val Leu Lys Pro Asn  Asn Phe Ile
    1085                 1090                1095

Asp Arg  Arg Lys Asp Ser  Thr  Leu Ser Ile Asn Asn  Ile Arg Ser
    1100                 1105                1110

Thr Ile  Leu Leu Ala Asn  Arg  Leu Tyr Ser Gly Ile  Lys Val Lys
    1115                 1120                1125

Ile Gln  Arg Val Asn Asn  Ser  Ser Thr Asn Asp Asn  Leu Val Arg
    1130                 1135                1140

Lys Asn  Asp Gln Val Tyr  Ile  Asn Phe Val Ala Ser  Lys Thr His
    1145                 1150                1155

Leu Phe  Pro Leu Tyr Ala  Asp  Thr Ala Thr Thr Asn  Lys Glu Lys
    1160                 1165                1170

Thr Ile  Lys Ile Ser Ser  Ser  Gly Asn Arg Phe Asn  Gln Val Val
    1175                 1180                1185

Val Met  Asn Ser Val Gly  Asn  Asn Cys Thr Met Asn  Phe Lys Asn
    1190                 1195                1200

Asn Asn  Gly Asn Asn Ile  Gly  Leu Leu Gly Phe Lys  Ala Asp Thr
    1205                 1210                1215

Val Val  Ala Ser Thr Trp  Tyr  Tyr Thr His Met Arg  Asp His Thr
    1220                 1225                1230

Asn Ser  Asn Gly Cys Phe  Trp  Asn Phe Ile Ser Glu  Glu His Gly
    1235                 1240                1245

Trp Gln  Glu Lys
```

1250

<210> SEQ ID NO 6
<211> LENGTH: 1278
<212> TYPE: PRT
<213> ORGANISM: Clostridium botulinum

<400> SEQUENCE: 6

```
Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365
```

```
Phe Ile Lys Tyr Gly Phe Leu Lys Val Pro Asn Leu Leu Asp Asp Asp
    370             375             380
Ile Tyr Thr Val Ser Glu Gly Phe Asn Ile Gly Asn Leu Ala Val Asn
385             390             395             400
Asn Arg Gly Gln Asn Ile Lys Leu Asn Pro Lys Ile Ile Asp Ser Ile
            405             410             415
Pro Asp Lys Gly Leu Val Glu Lys Ile Val Lys Phe Cys Lys Ser Val
        420             425             430
Ile Pro Arg Lys Gly Thr Lys Ala Pro Pro Arg Leu Cys Ile Arg Val
            435             440             445
Asn Asn Arg Glu Leu Phe Phe Val Ala Ser Glu Ser Ser Tyr Asn Glu
450             455             460
Asn Asp Ile Asn Thr Pro Lys Glu Ile Asp Asp Thr Thr Asn Leu Asn
465             470             475             480
Asn Asn Tyr Arg Asn Asn Leu Asp Glu Val Ile Leu Asp Tyr Asn Ser
            485             490             495
Glu Thr Ile Pro Gln Ile Ser Asn Gln Thr Leu Asn Thr Leu Val Gln
            500             505             510
Asp Asp Ser Tyr Val Pro Arg Tyr Asp Ser Asn Gly Thr Ser Glu Ile
            515             520             525
Glu Glu His Asn Val Val Asp Leu Asn Val Phe Phe Tyr Leu His Ala
530             535             540
Gln Lys Val Pro Glu Gly Glu Thr Asn Ile Ser Leu Thr Ser Ser Ile
545             550             555             560
Asp Thr Ala Leu Ser Glu Glu Ser Gln Val Tyr Thr Phe Phe Ser Ser
            565             570             575
Glu Phe Ile Asn Thr Ile Asn Lys Pro Val His Ala Ala Leu Phe Ile
            580             585             590
Ser Trp Ile Asn Gln Val Ile Arg Asp Phe Thr Thr Glu Ala Thr Gln
            595             600             605
Lys Ser Thr Phe Asp Lys Ile Ala Asp Ile Ser Leu Val Val Pro Tyr
            610             615             620
Val Gly Leu Ala Leu Asn Ile Gly Asn Glu Val Gln Lys Glu Asn Phe
625             630             635             640
Lys Glu Ala Phe Glu Leu Leu Gly Ala Gly Ile Leu Leu Glu Phe Val
            645             650             655
Pro Glu Leu Leu Ile Pro Thr Ile Leu Val Phe Thr Ile Lys Ser Phe
            660             665             670
Ile Gly Ser Ser Glu Asn Lys Asn Lys Ile Ile Lys Ala Ile Asn Asn
            675             680             685
Ser Leu Met Glu Arg Glu Thr Lys Trp Lys Glu Ile Tyr Ser Trp Ile
690             695             700
Val Ser Asn Trp Leu Thr Arg Ile Asn Thr Gln Phe Asn Lys Arg Lys
705             710             715             720
Glu Gln Met Tyr Gln Ala Leu Gln Asn Gln Val Asp Ala Ile Lys Thr
            725             730             735
Val Ile Glu Tyr Lys Tyr Asn Asn Tyr Thr Ser Asp Glu Arg Asn Arg
            740             745             750
Leu Glu Ser Glu Tyr Asn Ile Asn Ile Arg Glu Glu Leu Asn Lys
            755             760             765
Lys Val Ser Leu Ala Met Glu Asn Ile Glu Arg Phe Ile Thr Glu Ser
770             775             780
Ser Ile Phe Tyr Leu Met Lys Leu Ile Asn Glu Ala Lys Val Ser Lys
```

-continued

```
            785                 790                 795                 800
Leu Arg Glu Tyr Asp Glu Gly Val Lys Glu Tyr Leu Asp Tyr Ile
                    805                 810                 815

Ser Glu His Arg Ser Ile Leu Gly Asn Ser Val Gln Glu Leu Asn Asp
                    820                 825                 830

Leu Val Thr Ser Thr Leu Asn Ser Ile Pro Phe Glu Leu Ser Ser
                    835                 840                 845

Tyr Thr Asn Asp Lys Ile Leu Ile Leu Tyr Phe Asn Lys Leu Tyr Lys
        850                 855                 860

Lys Ile Lys Asp Asn Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asp
                        885                 890                 895

Val Tyr Ile Tyr Ser Thr Asn Arg Asn Gln Phe Gly Ile Tyr Ser Ser
                    900                 905                 910

Lys Pro Ser Glu Val Asn Ile Ala Gln Asn Asn Asp Ile Ile Tyr Asn
                915                 920                 925

Gly Arg Tyr Gln Asn Phe Ser Ile Ser Phe Trp Val Arg Ile Pro Lys
            930                 935                 940

Tyr Phe Asn Lys Val Asn Leu Asn Asn Glu Tyr Thr Ile Ile Asp Cys
945                 950                 955                 960

Ile Arg Asn Asn Asn Ser Gly Trp Lys Ile Ser Leu Asn Tyr Asn Lys
                    965                 970                 975

Ile Ile Trp Thr Leu Gln Asp Thr Ala Gly Asn Asn Gln Lys Leu Val
                980                 985                 990

Phe Asn Tyr Thr Gln Met Ile Ser Ile Ser Asp Tyr Ile Asn Lys Trp
            995                 1000                1005

Ile Phe Val Thr Ile Thr Asn Asn Arg Leu Gly Asn Ser Arg Ile
            1010                1015                1020

Tyr Ile Asn Gly Asn Leu Ile Asp Glu Lys Ser Ile Ser Asn Leu
            1025                1030                1035

Gly Asp Ile His Val Ser Asp Asn Ile Leu Phe Lys Ile Val Gly
            1040                1045                1050

Cys Asn Asp Thr Arg Tyr Val Gly Ile Arg Tyr Phe Lys Val Phe
            1055                1060                1065

Asp Thr Glu Leu Gly Lys Thr Glu Ile Glu Thr Leu Tyr Ser Asp
            1070                1075                1080

Glu Pro Asp Pro Ser Ile Leu Lys Asp Phe Trp Gly Asn Tyr Leu
            1085                1090                1095

Leu Tyr Asn Lys Arg Tyr Tyr Leu Leu Asn Leu Leu Arg Thr Asp
            1100                1105                1110

Lys Ser Ile Thr Gln Asn Ser Asn Phe Leu Asn Ile Asn Gln Gln
            1115                1120                1125

Arg Gly Val Tyr Gln Lys Pro Asn Ile Phe Ser Asn Thr Arg Leu
            1130                1135                1140

Tyr Thr Gly Val Glu Val Ile Ile Arg Lys Asn Gly Ser Thr Asp
            1145                1150                1155

Ile Ser Asn Thr Asp Asn Phe Val Arg Lys Asn Asp Leu Ala Tyr
            1160                1165                1170

Ile Asn Val Val Asp Arg Asp Val Glu Tyr Arg Leu Tyr Ala Asp
            1175                1180                1185

Ile Ser Ile Ala Lys Pro Glu Lys Ile Ile Lys Leu Ile Arg Thr
            1190                1195                1200
```

Ser Asn Ser Asn Asn Ser Leu Gly Gln Ile Ile Val Met Asp Ser
    1205                1210                1215

Ile Gly Asn Asn Cys Thr Met Asn Phe Gln Asn Asn Asn Gly Gly
    1220                1225                1230

Asn Ile Gly Leu Leu Gly Phe His Ser Asn Asn Leu Val Ala Ser
    1235                1240                1245

Ser Trp Tyr Tyr Asn Asn Ile Arg Lys Asn Thr Ser Ser Asn Gly
    1250                1255                1260

Cys Phe Trp Ser Phe Ile Ser Lys Glu His Gly Trp Gln Glu Asn
    1265                1270                1275

<210> SEQ ID NO 7
<211> LENGTH: 1297
<212> TYPE: PRT
<213> ORGANISM: Clostridium botulinum

<400> SEQUENCE: 7

Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn

-continued

```
           290                 295                 300
Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys Asn Thr Gly Lys Ser Glu
        435                 440                 445

Gln Cys Ile Ile Val Asn Asn Glu Asp Leu Phe Phe Ile Ala Asn Lys
    450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
            500                 505                 510

Glu Pro Phe Thr Asn Phe Asp Asp Ile Asp Ile Pro Val Tyr Ile Lys
        515                 520                 525

Gln Ser Ala Leu Lys Lys Ile Phe Val Asp Gly Asp Ser Leu Phe Glu
    530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
            580                 585                 590

Ser Leu Phe Val Asn Trp Val Lys Gly Val Ile Asp Asp Phe Thr Ser
        595                 600                 605

Glu Ser Thr Gln Lys Ser Thr Ile Asp Lys Val Ser Asp Val Ser Ile
    610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
            660                 665                 670

Leu Glu Ser Tyr Val Gly Asn Lys Gly His Ile Ile Met Thr Ile Ser
        675                 680                 685

Asn Ala Leu Lys Lys Arg Asp Gln Lys Trp Thr Asp Met Tyr Gly Leu
    690                 695                 700

Ile Val Ser Gln Trp Leu Ser Thr Val Asn Thr Gln Phe Tyr Thr Ile
705                 710                 715                 720
```

```
Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Asp Lys Met
            740                 745                 750

Asn Ile Asn Ile Asp Phe Asn Asp Ile Asp Phe Lys Leu Asn Gln Ser
                755                 760                 765

Ile Asn Leu Ala Ile Asn Asn Ile Asp Asp Phe Ile Asn Gln Cys Ser
770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
                820                 825                 830

Val Asn Arg His Leu Lys Asp Ser Ile Pro Phe Asp Leu Ser Leu Tyr
                835                 840                 845

Thr Lys Asp Thr Ile Leu Ile Gln Val Phe Asn Asn Tyr Ile Ser Asn
850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
                900                 905                 910

Asn Ser Asn Ile Thr Ala His Gln Ser Lys Phe Val Val Tyr Asp Ser
                915                 920                 925

Met Phe Asp Asn Phe Ser Ile Asn Phe Trp Val Arg Thr Pro Lys Tyr
            930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
            980                 985                 990

Phe Phe Glu Tyr Ser Ile Lys Asp  Asn Ile Ser Asp Tyr  Ile Asn Lys
                995                 1000                1005

Trp Phe  Ser Ile Thr Ile Thr  Asn Asp Arg Leu Gly  Asn Ala Asn
    1010                1015                1020

Ile Tyr  Ile Asn Gly Ser Leu  Lys Lys Ser Glu Lys  Ile Leu Asn
    1025                1030                1035

Leu Asp Arg Ile Asn Ser Ser  Asn Asp Ile Asp Phe  Lys Leu Ile
    1040                1045                1050

Asn Cys  Thr Asp Thr Thr Lys  Phe Val Trp Ile Lys  Asp Phe Asn
    1055                1060                1065

Ile Phe  Gly Arg Glu Leu Asn  Ala Thr Glu Val Ser  Ser Leu Tyr
    1070                1075                1080

Trp Ile  Gln Ser Ser Thr Asn  Thr Leu Lys Asp Phe  Trp Gly Asn
    1085                1090                1095

Pro Leu  Arg Tyr Asp Thr Gln  Tyr Tyr Leu Phe Asn  Gln Gly Met
    1100                1105                1110

Gln Asn  Ile Tyr Ile Lys Tyr  Phe Ser Lys Ala Ser  Met Gly Glu
    1115                1120                1125
```

```
Thr Ala Pro Arg Thr Asn Phe Asn Asn Ala Ala Ile Asn Tyr Gln
    1130                1135               1140

Asn Leu Tyr Leu Gly Leu Arg Phe Ile Ile Lys Lys Ala Ser Asn
    1145                1150               1155

Ser Arg Asn Ile Asn Asn Asp Asn Ile Val Arg Glu Gly Asp Tyr
    1160                1165               1170

Ile Tyr Leu Asn Ile Asp Asn Ile Ser Asp Glu Ser Tyr Arg Val
    1175                1180               1185

Tyr Val Leu Val Asn Ser Lys Glu Ile Gln Thr Gln Leu Phe Leu
    1190                1195               1200

Ala Pro Ile Asn Asp Asp Pro Thr Phe Tyr Asp Val Leu Gln Ile
    1205                1210               1215

Lys Lys Tyr Tyr Glu Lys Thr Thr Tyr Asn Cys Gln Ile Leu Cys
    1220                1225               1230

Glu Lys Asp Thr Lys Thr Phe Gly Leu Phe Gly Ile Gly Lys Phe
    1235                1240               1245

Val Lys Asp Tyr Gly Tyr Val Trp Asp Thr Tyr Asp Asn Tyr Phe
    1250                1255               1260

Cys Ile Ser Gln Trp Tyr Leu Arg Arg Ile Ser Glu Asn Ile Asn
    1265                1270               1275

Lys Leu Arg Leu Gly Cys Asn Trp Gln Phe Ile Pro Val Asp Glu
    1280                1285               1290

Gly Trp Thr Glu
    1295

<210> SEQ ID NO 8
<211> LENGTH: 1315
<212> TYPE: PRT
<213> ORGANISM: Clostridium tetani

<400> SEQUENCE: 8

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
                20                  25                  30

Tyr Tyr Lys Ala Phe Lys Ile Thr Asp Arg Ile Trp Ile Val Pro Glu
            35                  40                  45

Arg Tyr Glu Phe Gly Thr Lys Pro Glu Asp Phe Asn Pro Pro Ser Ser
        50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
                100                 105                 110

Asn Ala Ile Pro Tyr Leu Gly Asn Ser Tyr Ser Leu Leu Asp Lys Phe
            115                 120                 125

Asp Thr Asn Ser Asn Ser Val Ser Phe Asn Leu Leu Glu Gln Asp Pro
        130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
                180                 185                 190
```

```
Ile Met Gln Met Ala Phe Cys Pro Glu Tyr Val Pro Thr Phe Asp Asn
            195                 200                 205

Val Ile Glu Asn Ile Thr Ser Leu Thr Ile Gly Lys Ser Lys Tyr Phe
210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
                260                 265                 270

Phe Thr Phe Gly Gly Gln Asp Ala Asn Leu Ile Ser Ile Asp Ile Lys
            275                 280                 285

Asn Asp Leu Tyr Glu Lys Thr Leu Asn Asp Tyr Lys Ala Ile Ala Asn
290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
                340                 345                 350

Ser Ile Met Tyr Gly Phe Thr Glu Ile Glu Leu Gly Lys Lys Phe Asn
            355                 360                 365

Ile Lys Thr Arg Leu Ser Tyr Phe Ser Met Asn His Asp Pro Val Lys
            370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
                420                 425                 430

Ser Lys Leu Ile Gly Leu Cys Lys Lys Ile Ile Pro Pro Thr Asn Ile
            435                 440                 445

Arg Glu Asn Leu Tyr Asn Arg Thr Ala Ser Leu Thr Asp Leu Gly Gly
            450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
                500                 505                 510

Ile Val Asp Tyr Asn Leu Gln Ser Lys Ile Thr Leu Pro Asn Asp Arg
            515                 520                 525

Thr Thr Pro Val Thr Lys Gly Ile Pro Tyr Ala Pro Glu Tyr Lys Ser
530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
            595                 600                 605
```

-continued

```
Gly Ile Leu Phe Leu Gln Trp Val Arg Asp Ile Asp Asp Phe Thr
610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
            645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
            675                 680                 685

Ser Ile Ala Glu Ser Ser Thr Gln Lys Glu Lys Ile Ile Lys Thr Ile
690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
            725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
            755                 760                 765

Glu Gln Ile Ala Asp Glu Ile Asn Asn Leu Lys Asn Lys Leu Glu Glu
            770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
            805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
            835                 840                 845

Ser Lys Ile Asn Lys Val Phe Ser Thr Pro Ile Pro Phe Ser Tyr Ser
850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
            885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
            915                 920                 925

Glu Ser Ser Glu Val Ile Val His Lys Ala Met Asp Ile Glu Tyr Asn
930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
            965                 970                 975

Ile Ser Ser Met Lys Lys His Ser Leu Ser Ile Gly Ser Gly Trp Ser
            980                 985                 990

Val Ser Leu Lys Gly Asn Asn Leu Ile Trp Thr Leu Lys Asp Ser Ala
            995                 1000                1005

Gly Glu Val Arg Gln Ile Thr Phe Arg Asp Leu Pro Asp Lys Phe
        1010                1015                1020

Asn Ala Tyr Leu Ala Asn Lys Trp Val Phe Ile Thr Ile Thr Asn
```

```
                    1025                1030                1035

Asp Arg Leu Ser Ser Ala Asn Leu Tyr Ile Asn Gly Val Leu Met
                1040                1045                1050

Gly Ser Ala Glu Ile Thr Gly Leu Gly Ala Ile Arg Glu Asp Asn
                1055                1060                1065

Asn Ile Thr Leu Lys Leu Asp Arg Cys Asn Asn Asn Asn Gln Tyr
                1070                1075                1080

Val Ser Ile Asp Lys Phe Arg Ile Phe Cys Lys Ala Leu Asn Pro
                1085                1090                1095

Lys Glu Ile Glu Lys Leu Tyr Thr Ser Tyr Leu Ser Ile Thr Phe
                1100                1105                1110

Leu Arg Asp Phe Trp Gly Asn Pro Leu Arg Tyr Asp Thr Glu Tyr
                1115                1120                1125

Tyr Leu Ile Pro Val Ala Ser Ser Lys Asp Val Gln Leu Lys
                1130                1135                1140

Asn Ile Thr Asp Tyr Met Tyr Leu Thr Asn Ala Pro Ser Tyr Thr
                1145                1150                1155

Asn Gly Lys Leu Asn Ile Tyr Tyr Arg Arg Leu Tyr Asn Gly Leu
                1160                1165                1170

Lys Phe Ile Ile Lys Arg Tyr Thr Pro Asn Asn Glu Ile Asp Ser
                1175                1180                1185

Phe Val Lys Ser Gly Asp Phe Ile Lys Leu Tyr Val Ser Tyr Asn
                1190                1195                1200

Asn Asn Glu His Ile Val Gly Tyr Pro Lys Asp Gly Asn Ala Phe
                1205                1210                1215

Asn Asn Leu Asp Arg Ile Leu Arg Val Gly Tyr Asn Ala Pro Gly
                1220                1225                1230

Ile Pro Leu Tyr Lys Lys Met Glu Ala Val Lys Leu Arg Asp Leu
                1235                1240                1245

Lys Thr Tyr Ser Val Gln Leu Lys Leu Tyr Asp Asp Lys Asn Ala
                1250                1255                1260

Ser Leu Gly Leu Val Gly Thr His Asn Gly Gln Ile Gly Asn Asp
                1265                1270                1275

Pro Asn Arg Asp Ile Leu Ile Ala Ser Asn Trp Tyr Phe Asn His
                1280                1285                1290

Leu Lys Asp Lys Ile Leu Gly Cys Asp Trp Tyr Phe Val Pro Thr
                1295                1300                1305

Asp Glu Gly Trp Thr Asn Asp
                1310                1315

<210> SEQ ID NO 9
<211> LENGTH: 118
<212> TYPE: PRT
<213> ORGANISM: Rattus norvegicus

<400> SEQUENCE: 9

Met Ser Ala Pro Ala Gln Pro Pro Ala Glu Gly Thr Glu Gly Ala Ala
1               5                   10                  15

Pro Gly Gly Gly Pro Pro Gly Pro Pro Asn Thr Thr Ser Asn Arg
                20                  25                  30

Arg Leu Gln Gln Thr Gln Ala Gln Val Glu Glu Val Val Asp Ile Met
            35                  40                  45

Arg Val Asn Val Asp Lys Val Leu Glu Arg Asp Gln Lys Leu Ser Glu
        50                  55                  60
```

```
Leu Asp Asp Arg Ala Asp Ala Leu Gln Ala Gly Ala Ser Val Phe Glu
 65                  70                  75                  80

Ser Ser Ala Ala Lys Leu Lys Arg Lys Tyr Trp Trp Lys Asn Cys Lys
                 85                  90                  95

Met Met Ile Met Leu Gly Ala Ile Cys Ala Ile Ile Val Val Val Ile
            100                 105                 110

Val Ile Tyr Ile Phe Thr
            115

<210> SEQ ID NO 10
<211> LENGTH: 118
<212> TYPE: PRT
<213> ORGANISM: Homo sapiens

<400> SEQUENCE: 10

Met Ser Ala Pro Ala Gln Pro Pro Ala Glu Gly Thr Glu Gly Thr Ala
 1               5                  10                  15

Pro Gly Gly Gly Pro Pro Gly Pro Pro Pro Asn Met Thr Ser Asn Arg
                20                  25                  30

Arg Leu Gln Gln Thr Gln Ala Gln Val Glu Glu Val Val Asp Ile Ile
            35                  40                  45

Arg Val Asn Val Asp Lys Val Leu Glu Arg Asp Gln Lys Leu Ser Glu
         50                 55                  60

Leu Asp Asp Arg Ala Asp Ala Leu Gln Ala Gly Ala Ser Gln Phe Glu
 65                 70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Ile Tyr Phe Phe Thr
            115

<210> SEQ ID NO 11
<211> LENGTH: 116
<212> TYPE: PRT
<213> ORGANISM: Rattus norvegicus

<400> SEQUENCE: 11

Met Ser Ala Thr Ala Ala Thr Val Pro Pro Ala Ala Pro Ala Gly Glu
 1               5                  10                  15

Gly Gly Pro Pro Ala Pro Pro Pro Asn Leu Thr Ser Asn Arg Arg Leu
                20                  25                  30

Gln Gln Thr Gln Ala Gln Val Asp Glu Val Val Asp Ile Met Arg Val
            35                  40                  45

Asn Val Asp Lys Val Leu Glu Arg Asp Gln Lys Leu Ser Glu Leu Asp
         50                 55                  60

Asp Arg Ala Asp Ala Leu Gln Ala Gly Ala Ser Gln Phe Glu Thr Ser
 65                 70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
            115

<210> SEQ ID NO 12
<211> LENGTH: 116
```

<212> TYPE: PRT
<213> ORGANISM: Homo sapiens

<400> SEQUENCE: 12

Met Ser Ala Thr Ala Ala Thr Ala Pro Pro Ala Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
            115

<210> SEQ ID NO 13
<211> LENGTH: 103
<212> TYPE: PRT
<213> ORGANISM: Rattus norvegicus

<400> SEQUENCE: 13

Met Ser Thr Gly Val Pro Ser Gly Ser Ser Ala Ala Thr Gly Ser Asn
1               5                   10                  15

Arg Arg Leu Gln Gln Thr Gln Asn Gln Val Asp Glu Val Val Asp Ile
            20                  25                  30

Met Arg Val Asn Val Asp Lys Val Leu Glu Arg Asp Gln Lys Leu Ser
        35                  40                  45

Glu Leu Asp Asp Arg Ala Asp Ala Leu Gln Ala Gly Ala Ser Gln Phe
50                  55                  60

Glu Thr Ser Ala Ala Lys Leu Lys Arg Lys Tyr Trp Trp Lys Asn Cys
65                  70                  75                  80

Lys Met Trp Ala Ile Gly Ile Ser Val Leu Val Ile Ile Val Ile Ile
                85                  90                  95

Ile Ile Val Trp Cys Val Ser
            100

<210> SEQ ID NO 14
<211> LENGTH: 100
<212> TYPE: PRT
<213> ORGANISM: Homo sapiens

<400> SEQUENCE: 14

Met Ser Thr Gly Pro Thr Ala Ala Thr Gly Ser Asn Arg Arg Leu Gln
1               5                   10                  15

Gln Thr Gln Asn Gln Val Asp Glu Val Val Asp Ile Met Arg Val Asn
            20                  25                  30

Val Asp Lys Val Leu Glu Arg Asp Gln Lys Leu Ser Glu Leu Asp Asp
        35                  40                  45

Arg Ala Asp Ala Leu Gln Ala Gly Ala Ser Gln Phe Glu Thr Ser Ala
50                  55                  60

Ala Lys Leu Lys Arg Lys Tyr Trp Trp Lys Asn Cys Lys Met Trp Ala

```
                65                  70                  75                  80
Ile Gly Ile Thr Val Leu Val Ile Phe Ile Ile Ile Ile Val Trp
                    85                  90                  95

Val Val Ser Ser
            100

<210> SEQ ID NO 15
<211> LENGTH: 13
<212> TYPE: PRT
<213> ORGANISM: Artificial Sequence
<220> FEATURE:
<223> OTHER INFORMATION: VAMP epitope

<400> SEQUENCE: 15

Lys Leu Ser Glu Leu Asp Asp Arg Ala Asp Ala Leu Gln
1               5                   10

<210> SEQ ID NO 16
<211> LENGTH: 14
<212> TYPE: PRT
<213> ORGANISM: artificial sequence
<220> FEATURE:
<223> OTHER INFORMATION: VAMP epitope

<400> SEQUENCE: 16

Gln Lys Leu Ser Glu Leu Asp Asp Arg Ala Asp Ala Leu Gln
1               5                   10

<210> SEQ ID NO 17
<211> LENGTH: 10
<212> TYPE: PRT
<213> ORGANISM: artificial sequence
<220> FEATURE:
<223> OTHER INFORMATION: VAMP epitope

<400> SEQUENCE: 17

Lys Leu Ser Glu Leu Asp Asp Arg Ala Asp
1               5                   10

<210> SEQ ID NO 18
<211> LENGTH: 17
<212> TYPE: PRT
<213> ORGANISM: artificial sequence
<220> FEATURE:
<223> OTHER INFORMATION: VAMP epitope

<400> SEQUENCE: 18

Lys Leu Ser Glu Leu Asp Asp Arg Ala Asp Ala Leu Gln Ala Gly Ala
1               5                   10                  15

Ser

<210> SEQ ID NO 19
<211> LENGTH: 12
<212> TYPE: PRT
<213> ORGANISM: artificial sequence
<220> FEATURE:
<223> OTHER INFORMATION: VAMP epitope

<400> SEQUENCE: 19

Leu Ser Glu Leu Asp Asp Arg Ala Asp Ala Leu Gln
1               5                   10

<210> SEQ ID NO 20
<211> LENGTH: 10
<212> TYPE: PRT
```

```
<213> ORGANISM: artificial sequence
<220> FEATURE:
<223> OTHER INFORMATION: VAMP epitope

<400> SEQUENCE: 20

Leu Ser Glu Leu Asp Asp Arg Ala Asp Ala
1               5                   10

<210> SEQ ID NO 21
<211> LENGTH: 16
<212> TYPE: PRT
<213> ORGANISM: artificial sequence
<220> FEATURE:
<223> OTHER INFORMATION: VAMP epitope

<400> SEQUENCE: 21

Leu Ser Glu Leu Asp Asp Arg Ala Asp Ala Leu Gln Ala Gly Ala Ser
1               5                   10                  15

<210> SEQ ID NO 22
<211> LENGTH: 13
<212> TYPE: PRT
<213> ORGANISM: artificial sequence
<220> FEATURE:
<223> OTHER INFORMATION: VAMP epitope

<400> SEQUENCE: 22

Phe Glu Thr Ser Ala Ala Lys Leu Lys Arg Lys Tyr Trp
1               5                   10

<210> SEQ ID NO 23
<211> LENGTH: 13
<212> TYPE: PRT
<213> ORGANISM: artificial sequence
<220> FEATURE:
<223> OTHER INFORMATION: VAMP epitope

<400> SEQUENCE: 23

Phe Glu Ser Ser Ala Ala Lys Leu Lys Arg Lys Tyr Trp
1               5                   10

<210> SEQ ID NO 24
<211> LENGTH: 14
<212> TYPE: PRT
<213> ORGANISM: artificial sequence
<220> FEATURE:
<223> OTHER INFORMATION: VAMP epitope

<400> SEQUENCE: 24

Gln Phe Glu Thr Ser Ala Ala Lys Leu Lys Arg Lys Tyr Trp
1               5                   10

<210> SEQ ID NO 25
<211> LENGTH: 10
<212> TYPE: PRT
<213> ORGANISM: artificial sequence
<220> FEATURE:
<223> OTHER INFORMATION: VAMP epitope

<400> SEQUENCE: 25

Phe Glu Thr Ser Ala Ala Lys Leu Lys Arg
1               5                   10

<210> SEQ ID NO 26
<211> LENGTH: 16
<212> TYPE: PRT
<213> ORGANISM: artificial sequence
```

```
<220> FEATURE:
<223> OTHER INFORMATION: VAMP epitope

<400> SEQUENCE: 26

Phe Glu Thr Ser Ala Ala Lys Leu Lys Arg Lys Tyr Trp Trp Lys Asn
1               5                   10                  15

<210> SEQ ID NO 27
<211> LENGTH: 11
<212> TYPE: PRT
<213> ORGANISM: artificial sequence
<220> FEATURE:
<223> OTHER INFORMATION: VAMP epitope

<400> SEQUENCE: 27

Ala Lys Leu Lys Arg Lys Tyr Trp Trp Lys Asn
1               5                   10

<210> SEQ ID NO 28
<211> LENGTH: 12
<212> TYPE: PRT
<213> ORGANISM: artificial sequence
<220> FEATURE:
<223> OTHER INFORMATION: VAMP epitope

<400> SEQUENCE: 28

Ala Ala Lys Leu Lys Arg Lys Tyr Trp Trp Lys Asn
1               5                   10

<210> SEQ ID NO 29
<211> LENGTH: 14
<212> TYPE: PRT
<213> ORGANISM: artificial sequence
<220> FEATURE:
<223> OTHER INFORMATION: VAMP epitope

<400> SEQUENCE: 29

Ala Lys Leu Lys Arg Lys Tyr Trp Trp Lys Asn Cys Lys Met
1               5                   10

<210> SEQ ID NO 30
<211> LENGTH: 14
<212> TYPE: PRT
<213> ORGANISM: artificial sequence
<220> FEATURE:
<223> OTHER INFORMATION: VAMP epitope

<400> SEQUENCE: 30

Ala Lys Leu Lys Arg Lys Tyr Trp Trp Lys Asn Leu Lys Met
1               5                   10

<210> SEQ ID NO 31
<211> LENGTH: 15
<212> TYPE: PRT
<213> ORGANISM: artificial sequence
<220> FEATURE:
<223> OTHER INFORMATION: VAMP epitope

<400> SEQUENCE: 31

Asp Gln Lys Leu Ser Glu Leu Asp Asp Arg Ala Asp Ala Leu Gln
1               5                   10                  15

<210> SEQ ID NO 32
<211> LENGTH: 13
<212> TYPE: PRT
<213> ORGANISM: artificial sequence
<220> FEATURE:
```

-continued

<223> OTHER INFORMATION: VAMP epitope

<400> SEQUENCE: 32

Glu Arg Asp Gln Lys Leu Ser Glu Leu Asp Asp Arg Ala
1               5                   10

<210> SEQ ID NO 33
<211> LENGTH: 14
<212> TYPE: PRT
<213> ORGANISM: artificial sequence
<220> FEATURE:
<223> OTHER INFORMATION: VAMP epitope

<400> SEQUENCE: 33

Leu Glu Arg Asp Gln Lys Leu Ser Glu Leu Asp Asp Arg Ala
1               5                   10

<210> SEQ ID NO 34
<211> LENGTH: 15
<212> TYPE: PRT
<213> ORGANISM: artificial sequence
<220> FEATURE:
<223> OTHER INFORMATION: VAMP epitope

<400> SEQUENCE: 34

Val Leu Glu Arg Asp Gln Lys Leu Ser Glu Leu Asp Asp Arg Ala
1               5                   10                  15

<210> SEQ ID NO 35
<211> LENGTH: 888
<212> TYPE: PRT
<213> ORGANISM: Artificial Sequence
<220> FEATURE:
<223> OTHER INFORMATION: LHND

<400> SEQUENCE: 35

Met Gly Ser Met Thr Trp Pro Val Lys Asp Phe Asn Tyr Ser Asp Pro
1               5                   10                  15

Val Asn Asp Asn Asp Ile Leu Tyr Leu Arg Ile Pro Gln Asn Lys Leu
                20                  25                  30

Ile Thr Thr Pro Val Lys Ala Phe Met Ile Thr Gln Asn Ile Trp Val
            35                  40                  45

Ile Pro Glu Arg Phe Ser Ser Asp Thr Asn Pro Ser Leu Ser Lys Pro
        50                  55                  60

Pro Arg Pro Thr Ser Lys Tyr Gln Ser Tyr Tyr Asp Pro Ser Tyr Leu
65                  70                  75                  80

Ser Thr Asp Glu Gln Lys Asp Thr Phe Leu Lys Gly Ile Ile Lys Leu
                85                  90                  95

Phe Lys Arg Ile Asn Glu Arg Asp Ile Gly Lys Lys Leu Ile Asn Tyr
            100                 105                 110

Leu Val Val Gly Ser Pro Phe Met Gly Asp Ser Ser Thr Pro Glu Asp
        115                 120                 125

Thr Phe Asp Phe Thr Arg His Thr Thr Asn Ile Ala Val Glu Lys Phe
    130                 135                 140

Glu Asn Gly Ser Trp Lys Val Thr Asn Ile Ile Thr Pro Ser Val Leu
145                 150                 155                 160

Ile Phe Gly Pro Leu Pro Asn Ile Leu Asp Tyr Thr Ala Ser Leu Thr
                165                 170                 175

Leu Gln Gly Gln Gln Ser Asn Pro Ser Phe Glu Gly Phe Gly Thr Leu
            180                 185                 190

-continued

```
Ser Ile Leu Lys Val Ala Pro Glu Phe Leu Leu Thr Phe Ser Asp Val
            195                 200                 205
Thr Ser Asn Gln Ser Ser Ala Val Leu Gly Lys Ser Ile Phe Cys Met
    210                 215                 220
Asp Pro Val Ile Ala Leu Met His Glu Leu Thr His Ser Leu His Gln
225                 230                 235                 240
Leu Tyr Gly Ile Asn Ile Pro Ser Asp Lys Arg Ile Arg Pro Gln Val
                245                 250                 255
Ser Glu Gly Phe Phe Ser Gln Asp Gly Pro Asn Val Gln Phe Glu Glu
            260                 265                 270
Leu Tyr Thr Phe Gly Gly Leu Asp Val Glu Ile Ile Pro Gln Ile Glu
        275                 280                 285
Arg Ser Gln Leu Arg Glu Lys Ala Leu Gly His Tyr Lys Asp Ile Ala
    290                 295                 300
Lys Arg Leu Asn Asn Ile Asn Lys Thr Ile Pro Ser Ser Trp Ile Ser
305                 310                 315                 320
Asn Ile Asp Lys Tyr Lys Lys Ile Phe Ser Glu Lys Tyr Asn Phe Asp
                325                 330                 335
Lys Asp Asn Thr Gly Asn Phe Val Val Asn Ile Asp Lys Phe Asn Ser
            340                 345                 350
Leu Tyr Ser Asp Leu Thr Asn Val Met Ser Glu Val Val Tyr Ser Ser
        355                 360                 365
Gln Tyr Asn Val Lys Asn Arg Thr His Tyr Phe Ser Arg His Tyr Leu
    370                 375                 380
Pro Val Phe Ala Asn Ile Leu Asp Asp Asn Ile Tyr Thr Ile Arg Asp
385                 390                 395                 400
Gly Phe Asn Leu Thr Asn Lys Gly Phe Asn Ile Glu Asn Ser Gly Gln
                405                 410                 415
Asn Ile Glu Arg Asn Pro Ala Leu Gln Lys Leu Ser Ser Glu Ser Val
            420                 425                 430
Val Asp Leu Phe Thr Lys Val Cys Val Asp Lys Ser Glu Glu Lys Leu
        435                 440                 445
Tyr Asp Asp Asp Asp Lys Asp Arg Trp Gly Ser Ser Leu Gln Cys Ile
    450                 455                 460
Lys Val Lys Asn Asn Arg Leu Pro Tyr Val Ala Asp Lys Asp Ser Ile
465                 470                 475                 480
Ser Gln Glu Ile Phe Glu Asn Lys Ile Ile Thr Asp Glu Thr Asn Val
                485                 490                 495
Gln Asn Tyr Ser Asp Lys Phe Ser Leu Asp Glu Ser Ile Leu Asp Gly
            500                 505                 510
Gln Val Pro Ile Asn Pro Glu Ile Val Asp Pro Leu Leu Pro Asn Val
        515                 520                 525
Asn Met Glu Pro Leu Asn Leu Pro Gly Glu Glu Ile Val Phe Tyr Asp
    530                 535                 540
Asp Ile Thr Lys Tyr Val Asp Tyr Leu Asn Ser Tyr Tyr Tyr Leu Glu
545                 550                 555                 560
Ser Gln Lys Leu Ser Asn Asn Val Glu Asn Ile Thr Leu Thr Thr Ser
                565                 570                 575
Val Glu Glu Ala Leu Gly Tyr Ser Asn Lys Ile Tyr Thr Phe Leu Pro
            580                 585                 590
Ser Leu Ala Glu Lys Val Asn Lys Gly Val Gln Ala Gly Leu Phe Leu
        595                 600                 605
Asn Trp Ala Asn Glu Val Val Glu Asp Phe Thr Thr Asn Ile Met Lys
```

```
                   610                 615                 620
Lys Asp Thr Leu Asp Lys Ile Ser Asp Val Ser Val Ile Ile Pro Tyr
625                 630                 635                 640

Ile Gly Pro Ala Leu Asn Ile Gly Asn Ser Ala Leu Arg Gly Asn Phe
                645                 650                 655

Asn Gln Ala Phe Ala Thr Ala Gly Val Ala Phe Leu Leu Glu Gly Phe
            660                 665                 670

Pro Glu Phe Thr Ile Pro Ala Leu Gly Val Phe Thr Phe Tyr Ser Ser
        675                 680                 685

Ile Gln Glu Arg Glu Lys Ile Ile Lys Thr Ile Glu Asn Cys Leu Glu
    690                 695                 700

Gln Arg Val Lys Arg Trp Lys Asp Ser Tyr Gln Trp Met Val Ser Asn
705                 710                 715                 720

Trp Leu Ser Arg Ile Thr Thr Gln Phe Asn His Ile Asn Tyr Gln Met
                725                 730                 735

Tyr Asp Ser Leu Ser Tyr Gln Ala Asp Ala Ile Lys Ala Lys Ile Asp
            740                 745                 750

Leu Glu Tyr Lys Lys Tyr Ser Gly Ser Asp Lys Glu Asn Ile Lys Ser
        755                 760                 765

Gln Val Glu Asn Leu Lys Asn Ser Leu Asp Val Lys Ile Ser Glu Ala
    770                 775                 780

Met Asn Asn Ile Asn Lys Phe Ile Arg Glu Cys Ser Val Thr Tyr Leu
785                 790                 795                 800

Phe Lys Asn Met Leu Pro Lys Val Ile Asp Glu Leu Asn Lys Phe Asp
                805                 810                 815

Leu Arg Thr Lys Thr Glu Leu Ile Asn Leu Ile Asp Ser His Asn Ile
            820                 825                 830

Ile Leu Val Gly Glu Val Asp Arg Leu Lys Ala Lys Val Asn Glu Ser
        835                 840                 845

Phe Glu Asn Thr Met Pro Phe Asn Ile Phe Ser Tyr Thr Asn Asn Ser
    850                 855                 860

Leu Leu Lys Asp Ile Ile Asn Glu Tyr Phe Asn Leu Glu Ala His His
865                 870                 875                 880

His His His His His
            885

<210> SEQ ID NO 36
<211> LENGTH: 837
<212> TYPE: PRT
<213> ORGANISM: Artificial Sequence
<220> FEATURE:
<223> OTHER INFORMATION: MBP-LF

<400> SEQUENCE: 36

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65              70                  75                  80

Thr Pro Asp Lys Ala Phe Gln Asp Lys Leu Tyr Pro Phe Thr Trp Asp
```

-continued

```
                85                  90                  95
Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
370                 375                 380

Glu Gly Arg Ile Ser Glu Phe Gly Ser Met Pro Val Ala Ile Asn Ser
385                 390                 395                 400

Phe Asn Tyr Asn Asp Pro Val Asn Asp Asp Thr Ile Leu Tyr Met Gln
                405                 410                 415

Ile Pro Tyr Glu Glu Lys Ser Lys Lys Tyr Tyr Lys Ala Phe Glu Ile
            420                 425                 430

Met Arg Asn Val Trp Ile Ile Pro Glu Arg Asn Thr Ile Gly Thr Asn
        435                 440                 445

Pro Ser Asp Phe Asp Pro Pro Ala Ser Leu Lys Asn Gly Ser Ser Ala
450                 455                 460

Tyr Tyr Asp Pro Asn Tyr Leu Thr Thr Asp Ala Glu Lys Asp Arg Tyr
465                 470                 475                 480

Leu Lys Thr Thr Ile Lys Leu Phe Lys Arg Ile Asn Ser Asn Pro Ala
                485                 490                 495

Gly Lys Val Leu Leu Gln Glu Ile Ser Tyr Ala Lys Pro Tyr Leu Gly
            500                 505                 510
```

Asn Asp His Thr Pro Ile Asp Glu Phe Ser Pro Val Thr Arg Thr Thr
            515                 520                 525

Ser Val Asn Ile Lys Leu Ser Thr Asn Val Glu Ser Ser Met Leu Leu
        530                 535                 540

Asn Leu Leu Val Leu Gly Ala Gly Pro Asp Ile Phe Glu Ser Cys Cys
545                 550                 555                 560

Tyr Pro Val Arg Lys Leu Ile Asp Pro Val Val Tyr Asp Pro Ser
                565                 570                 575

Asn Tyr Gly Phe Gly Ser Ile Asn Ile Val Thr Phe Ser Pro Glu Tyr
                580                 585                 590

Glu Tyr Thr Phe Asn Asp Ile Ser Gly Gly His Asn Ser Ser Thr Glu
        595                 600                 605

Ser Phe Ile Ala Asp Pro Ala Ile Ser Leu Ala His Glu Leu Ile His
        610                 615                 620

Ala Leu His Gly Leu Tyr Gly Ala Arg Gly Val Thr Tyr Glu Glu Thr
625                 630                 635                 640

Ile Glu Val Lys Gln Ala Pro Leu Met Ile Ala Glu Lys Pro Ile Arg
                645                 650                 655

Leu Glu Glu Phe Leu Thr Phe Gly Gly Gln Asp Leu Asn Ile Ile Thr
        660                 665                 670

Ser Ala Met Lys Glu Lys Ile Tyr Asn Asn Leu Leu Ala Asn Tyr Glu
        675                 680                 685

Lys Ile Ala Thr Arg Leu Ser Glu Val Asn Ser Ala Pro Pro Glu Tyr
        690                 695                 700

Asp Ile Asn Glu Tyr Lys Asp Tyr Phe Gln Trp Lys Tyr Gly Leu Asp
705                 710                 715                 720

Lys Asn Ala Asp Gly Ser Tyr Thr Val Asn Glu Asn Lys Phe Asn Glu
                725                 730                 735

Ile Tyr Lys Lys Leu Tyr Ser Phe Thr Glu Ser Asp Leu Ala Asn Lys
                740                 745                 750

Phe Lys Val Lys Cys Arg Asn Thr Tyr Phe Ile Lys Tyr Glu Phe Leu
        755                 760                 765

Lys Val Pro Asn Leu Leu Asp Asp Ile Tyr Thr Val Ser Glu Gly
770                 775                 780

Phe Asn Ile Gly Asn Leu Ala Val Asn Asn Arg Gly Gln Ser Ile Lys
785                 790                 795                 800

Leu Asn Pro Lys Ile Ile Asp Ser Ile Pro Asp Lys Gly Leu Val Glu
                805                 810                 815

Lys Ile Val Lys Phe Ala Val Asp Lys Leu Ala Ala Leu Glu His
                820                 825                 830

His His His His His
            835

<210> SEQ ID NO 37
<211> LENGTH: 339
<212> TYPE: PRT
<213> ORGANISM: Artificial Sequence
<220> FEATURE:
<223> OTHER INFORMATION: VAMP2-GFP

<400> SEQUENCE: 37

Gly Pro Leu Gly Ser Ser Ala Thr Ala Ala Thr Ala Pro Pro Ala Ala
1               5                   10                  15

Pro Ala Gly Glu Gly Gly Pro Pro Ala Pro Pro Asn Leu Thr Ser
            20                  25                  30

```
Asn Arg Arg Leu Gln Gln Thr Gln Ala Gln Val Asp Glu Val Val Asp
         35                  40                  45

Ile Met Arg Val Asn Val Asp Lys Val Leu Glu Arg Asp Gln Lys Leu
 50                  55                  60

Ser Glu Leu Asp Asp Arg Ala Asp Ala Leu Gln Ala Gly Ala Ser Gln
 65                  70                  75                  80

Phe Glu Thr Ser Ala Ala Lys Leu Lys Arg Lys Tyr Trp Trp Lys Asn
                 85                  90                  95

Leu Lys Leu Glu Asn Val Ser Lys Gly Glu Glu Leu Phe Thr Gly Val
            100                 105                 110

Val Pro Ile Leu Val Glu Leu Asp Gly Asp Val Asn Gly His Lys Phe
            115                 120                 125

Ser Val Ser Gly Glu Gly Glu Gly Asp Ala Thr Tyr Gly Lys Leu Thr
130                 135                 140

Leu Lys Phe Ile Cys Thr Thr Gly Lys Leu Pro Val Pro Trp Pro Thr
145                 150                 155                 160

Leu Val Thr Thr Leu Thr Tyr Gly Val Gln Cys Phe Ser Arg Tyr Pro
                165                 170                 175

Asp His Met Lys Gln His Asp Phe Phe Lys Ser Ala Met Pro Glu Gly
            180                 185                 190

Tyr Val Gln Glu Arg Thr Ile Phe Phe Lys Asp Asp Gly Asn Tyr Lys
            195                 200                 205

Thr Arg Ala Glu Val Lys Phe Glu Gly Asp Thr Leu Val Asn Arg Ile
210                 215                 220

Glu Leu Lys Gly Ile Asp Phe Lys Glu Asp Gly Asn Ile Leu Gly His
225                 230                 235                 240

Lys Leu Glu Tyr Asn Tyr Asn Ser His Asn Val Tyr Ile Met Ala Asp
                245                 250                 255

Lys Gln Lys Asn Gly Ile Lys Val Asn Phe Lys Ile Arg His Asn Ile
            260                 265                 270

Glu Asp Gly Ser Val Gln Leu Ala Asp His Tyr Gln Gln Asn Thr Pro
            275                 280                 285

Ile Gly Asp Gly Pro Val Leu Leu Pro Asp Asn His Tyr Leu Ser Thr
290                 295                 300

Gln Ser Ala Leu Ser Lys Asp Pro Asn Glu Lys Arg Asp His Met Val
305                 310                 315                 320

Leu Leu Glu Phe Val Thr Ala Ala Gly Ile Thr Leu Gly Met Asp Glu
                325                 330                 335

Leu Tyr Lys

<210> SEQ ID NO 38
<211> LENGTH: 1304
<212> TYPE: PRT
<213> ORGANISM: Artificial Sequence
<220> FEATURE:
<223> OTHER INFORMATION: BoNT/FA

<400> SEQUENCE: 38

Met Pro Val Val Ile Asn Ser Phe Asn Tyr Asp Asp Pro Val Asn Asp
 1               5                  10                  15

Asn Thr Ile Ile Tyr Ile Arg Pro Pro Tyr Tyr Glu Thr Ser Asn Thr
             20                  25                  30

Tyr Phe Lys Ala Phe Gln Ile Met Asp Asn Val Trp Ile Ile Pro Glu
         35                  40                  45
```

```
Arg Tyr Arg Leu Gly Ile Asp Pro Ser Leu Phe Asn Pro Pro Val Ser
    50                  55                  60
Leu Lys Ala Gly Ser Asp Gly Tyr Phe Asp Pro Asn Tyr Leu Ser Thr
65                  70                  75                  80
Asn Thr Glu Lys Asn Lys Tyr Leu Gln Ile Met Ile Lys Leu Phe Lys
                85                  90                  95
Arg Ile Asn Ser Lys Pro Ala Gly Gln Ile Leu Leu Glu Glu Ile Lys
                100                 105                 110
Asn Ala Ile Pro Tyr Leu Gly Asn Ser Tyr Thr Gln Glu Glu Gln Phe
            115                 120                 125
Thr Thr Asn Asn Arg Thr Val Ser Phe Asn Val Lys Leu Ala Asn Gly
    130                 135                 140
Asn Ile Val Gln Gln Met Ala Asn Leu Ile Ile Trp Gly Pro Gly Pro
145                 150                 155                 160
Asp Leu Thr Thr Asn Lys Thr Gly Gly Ile Ile Tyr Ser Pro Tyr Gln
                165                 170                 175
Ser Met Glu Ala Thr Pro Tyr Lys Asp Gly Phe Gly Ser Ile Met Thr
            180                 185                 190
Val Glu Phe Ser Pro Glu Tyr Ala Thr Ala Phe Asn Asp Ile Ser Ile
    195                 200                 205
Ala Ser His Ser Pro Ser Leu Phe Ile Lys Asp Pro Ala Leu Ile Leu
    210                 215                 220
Met His Glu Leu Ile His Val Leu His Gly Leu Tyr Gly Thr Tyr Ile
225                 230                 235                 240
Thr Glu Tyr Lys Ile Thr Pro Asn Val Val Gln Ser Tyr Met Lys Val
                245                 250                 255
Thr Lys Pro Ile Thr Ser Ala Glu Phe Leu Thr Phe Gly Gly Arg Asp
            260                 265                 270
Arg Asn Ile Val Pro Gln Ser Ile Gln Ser Gln Leu Tyr Asn Lys Val
    275                 280                 285
Leu Ser Asp Tyr Lys Arg Ile Ala Ser Arg Leu Asn Lys Val Asn Thr
    290                 295                 300
Ala Thr Ala Leu Ile Asn Ile Asp Glu Phe Lys Asn Leu Tyr Glu Trp
305                 310                 315                 320
Lys Tyr Gln Phe Ala Lys Asp Ser Asn Gly Val Tyr Ser Val Asp Leu
                325                 330                 335
Asn Lys Phe Glu Gln Leu Tyr Lys Lys Ile Tyr Ser Phe Thr Glu Phe
            340                 345                 350
Asn Leu Ala Tyr Glu Phe Lys Ile Lys Thr Arg Leu Gly Tyr Leu Ala
    355                 360                 365
Glu Asn Phe Gly Pro Phe Tyr Leu Pro Asn Leu Leu Asp Asp Ser Ile
    370                 375                 380
Tyr Thr Glu Val Asp Gly Phe Asn Ile Gly Ala Leu Ser Ile Asn Tyr
385                 390                 395                 400
Gln Gly Gln Asn Ile Gly Ser Asp Ile Asn Ser Ile Lys Lys Leu Gln
                405                 410                 415
Gly Gln Gly Val Val Ser Arg Val Arg Leu Cys Lys Ser Val Ile
            420                 425                 430
Pro Arg Lys Gly Thr Lys Ala Pro Arg Leu Cys Ile Thr Val Asn
    435                 440                 445
Asn Arg Asp Leu Phe Phe Ile Ala Ser Gln Glu Ser Tyr Gly Glu Asn
    450                 455                 460
Thr Ile Asn Thr Tyr Lys Glu Ile Asp Asp Thr Thr Thr Leu Asp Pro
```

```
                465                 470                 475                 480
            Ser Phe Glu Asp Ile Leu Asp Lys Val Ile Leu Asn Phe Asn Glu Gln
                            485                 490                 495
            Val Ile Pro Gln Met Pro Asn Arg Asn Val Ser Thr Asp Ile Gln Lys
                            500                 505                 510
            Asp Asn Tyr Ile Pro Lys Tyr Asp Tyr Asn Arg Thr Asp Ile Ile Asp
                            515                 520                 525
            Ser Tyr Glu Val Gly Arg Asn Tyr Asn Thr Phe Phe Tyr Leu Asn Ala
                    530                 535                 540
            Gln Lys Phe Ser Pro Asn Glu Ser Asn Ile Thr Leu Thr Ser Ser Phe
            545                 550                 555                 560
            Asp Thr Gly Leu Leu Glu Gly Ser Lys Val Tyr Thr Phe Phe Ser Ser
                            565                 570                 575
            Asp Phe Ile Asn Asn Ile Asn Lys Pro Val Gln Ala Leu Leu Phe Ile
                            580                 585                 590
            Glu Trp Val Lys Gln Val Ile Arg Asp Phe Thr Thr Glu Ala Thr Lys
                            595                 600                 605
            Thr Ser Thr Val Asp Lys Leu Lys Asp Ile Ser Leu Val Val Pro Tyr
                    610                 615                 620
            Ile Gly Leu Ala Leu Asn Ile Gly Asp Glu Ile Tyr Lys Gln His Phe
            625                 630                 635                 640
            Ala Glu Ala Val Glu Leu Val Gly Ala Gly Leu Leu Leu Glu Phe Ser
                            645                 650                 655
            Pro Glu Phe Leu Ile Pro Thr Leu Leu Ile Phe Thr Ile Lys Gly Tyr
                            660                 665                 670
            Leu Thr Gly Ser Ile Arg Asp Lys Asp Lys Ile Ile Lys Thr Leu Asp
                    675                 680                 685
            Asn Ala Leu Asn Val Arg Asp Gln Lys Trp Lys Glu Leu Tyr Arg Trp
                    690                 695                 700
            Val Val Ser Lys Trp Leu Thr Thr Ile Asn Thr Gln Phe Asn Lys Arg
            705                 710                 715                 720
            Lys Glu Gln Met Tyr Lys Ala Leu Lys Asn Gln Ala Thr Ala Ile Lys
                            725                 730                 735
            Lys Ile Ile Glu Asn Lys Tyr Asn Asn Tyr Thr Thr Asp Glu Lys Ser
                            740                 745                 750
            Lys Ile Asp Ser Ser Tyr Asn Ile Asn Glu Ile Glu Arg Thr Leu Asn
                    755                 760                 765
            Glu Lys Ile Asn Leu Ala Met Lys Asn Ile Glu Gln Phe Ile Thr Glu
                770                 775                 780
            Ser Ser Ile Ala Tyr Leu Ile Asn Ile Ile Asn Asn Glu Thr Ile Gln
            785                 790                 795                 800
            Lys Leu Lys Ser Tyr Asp Asp Leu Val Arg Arg Tyr Leu Leu Gly Tyr
                            805                 810                 815
            Ile Arg Asn His Ser Ser Ile Leu Gly Asn Ser Val Glu Glu Leu Asn
                            820                 825                 830
            Ser Lys Val Asn Asn His Leu Asp Asn Gly Ile Pro Phe Glu Leu Ser
                    835                 840                 845
            Ser Tyr Thr Asn Asp Ser Leu Leu Ile Arg Tyr Phe Asn Lys Asn Tyr
                850                 855                 860
            Gly Glu Leu Lys Tyr Asn Cys Ile Leu Asn Ile Lys Tyr Glu Met Asp
            865                 870                 875                 880
            Arg Asp Lys Leu Val Asp Ser Ser Gly Tyr Arg Ser Arg Ile Asn Ile
                            885                 890                 895
```

```
Gly Thr Gly Val Lys Phe Ser Glu Ile Asp Lys Asn Gln Val Gln Leu
                900                 905                 910

Ser Asn Leu Glu Ser Ser Lys Ile Glu Val Ile Leu Asn Asn Gly Val
            915                 920                 925

Ile Tyr Asn Ser Met Tyr Glu Asn Phe Ser Thr Ser Phe Trp Ile Arg
930                 935                 940

Ile Pro Lys Tyr Phe Arg Asn Ile Asn Asn Glu Tyr Lys Ile Ile Ser
945                 950                 955                 960

Cys Met Gln Asn Asn Ser Gly Trp Glu Val Ser Leu Asn Phe Ser Asn
                965                 970                 975

Met Asn Ser Lys Ile Ile Trp Thr Leu Gln Asp Thr Glu Gly Ile Lys
            980                 985                 990

Lys Thr Val Val Phe Gln Tyr Thr Gln Asn Ile Asn Ile Ser Asp Tyr
        995                 1000                1005

Ile Asn Arg Trp Ile Phe Val Thr Ile Thr Asn Asn Arg Leu Ser
    1010                1015                1020

Asn Ser Lys Ile Tyr Ile Asn Gly Arg Leu Ile Asn Glu Glu Ser
    1025                1030                1035

Ile Ser Asp Leu Gly Asn Ile His Ala Ser Asn Asn Ile Met Phe
    1040                1045                1050

Lys Leu Asp Gly Cys Arg Asp Pro His Arg Tyr Ile Trp Ile Lys
    1055                1060                1065

Tyr Phe Asn Leu Phe Asp Lys Glu Leu Asn Lys Lys Glu Ile Lys
    1070                1075                1080

Asp Leu Tyr Asp Asn Gln Ser Asn Ser Gly Ile Leu Lys Asp Phe
    1085                1090                1095

Trp Gly Asp Tyr Leu Gln Tyr Asp Lys Pro Tyr Tyr Met Leu Asn
    1100                1105                1110

Leu Tyr Asp Pro Asn Lys Tyr Leu Asp Val Asn Asn Val Gly Ile
    1115                1120                1125

Arg Gly Tyr Met Tyr Leu Lys Gly Pro Arg Gly Arg Ile Val Thr
    1130                1135                1140

Thr Asn Ile Tyr Leu Asn Ser Thr Leu Tyr Met Gly Thr Lys Phe
    1145                1150                1155

Ile Ile Lys Lys Tyr Ala Ser Gly Asn Lys Asp Asn Ile Val Arg
    1160                1165                1170

Asn Asn Asp Arg Val Tyr Ile Asn Val Val Val Lys Asn Lys Glu
    1175                1180                1185

Tyr Arg Leu Ala Thr Asn Ala Ser Gln Ala Gly Val Glu Lys Ile
    1190                1195                1200

Leu Ser Ala Val Glu Ile Pro Asp Val Gly Asn Leu Ser Gln Val
    1205                1210                1215

Val Val Met Lys Ser Glu Asn Asp Gln Gly Ile Arg Asn Lys Cys
    1220                1225                1230

Lys Met Asn Leu Gln Asp Asn Asn Gly Asn Asp Ile Gly Phe Ile
    1235                1240                1245

Gly Phe His Gln Phe Asn Asn Ile Ala Lys Leu Val Ala Ser Asn
    1250                1255                1260

Trp Tyr Asn Arg Gln Ile Gly Lys Ala Ser Arg Thr Phe Gly Cys
    1265                1270                1275

Ser Trp Glu Phe Ile Pro Val Asp Asp Gly Trp Gly Glu Ser Ser
    1280                1285                1290
```

```
Leu His  His His His His  His His His His
    1295           1300
```

<210> SEQ ID NO 39
<211> LENGTH: 15
<212> TYPE: PRT
<213> ORGANISM: Artificial Sequence
<220> FEATURE:
<223> OTHER INFORMATION: Pep1

<400> SEQUENCE: 39

```
Ser Asn Arg Arg Leu Gln Gln Thr Gln Ala Gln Val Asp Glu Cys
1               5                   10                  15
```

<210> SEQ ID NO 40
<211> LENGTH: 8
<212> TYPE: PRT
<213> ORGANISM: Artificial Sequence
<220> FEATURE:
<223> OTHER INFORMATION: Pep3

<400> SEQUENCE: 40

```
Cys Leu Gln Ala Gly Ala Ser Gln
1               5
```

<210> SEQ ID NO 41
<211> LENGTH: 1306
<212> TYPE: PRT
<213> ORGANISM: Clostridium botulinum

<400> SEQUENCE: 41

```
Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220
```

```
Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
            245                 250                 255

Arg Gln Gln Asn Ser Leu Ile Phe Glu Glu Leu Leu Thr Phe Gly Gly
        260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
            325                 330                 335

Lys Lys Leu Asn Thr Ile Leu Phe Val Leu Asn Glu Ser Asn Leu Ala
        340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
            405                 410                 415

Arg Ala Phe Ile Lys Ile Cys Pro Arg Asn Gly Leu Leu Tyr Asn Ala
        420                 425                 430

Ile Tyr Arg Asn Ser Lys Asn Tyr Leu Asn Asn Ile Asp Leu Glu Asp
        435                 440                 445

Lys Lys Thr Thr Ser Lys Thr Asn Val Ser Tyr Pro Cys Ser Leu Leu
    450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
            485                 490                 495

Glu Thr Thr Val Phe Phe Lys Asp Lys Leu Pro Pro Gln Asp Ile Thr
            500                 505                 510

Leu Ser Asn Tyr Asp Phe Thr Glu Ala Asn Ser Ile Pro Ser Ile Ser
        515                 520                 525

Gln Gln Asn Ile Leu Glu Arg Asn Glu Glu Leu Tyr Glu Pro Ile Arg
    530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
            565                 570                 575

Lys Ile Arg Val Glu Leu Thr Asp Ser Val Asp Glu Ala Leu Ser Asn
        580                 585                 590

Pro Asn Lys Val Tyr Ser Pro Phe Lys Asn Met Ser Asn Thr Ile Asn
        595                 600                 605

Ser Ile Glu Thr Gly Ile Thr Ser Thr Tyr Ile Phe Tyr Gln Trp Leu
        610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
```

645                 650                 655
Leu Leu Asn Ile Gly Asn Asp Ile Arg His Gly Asp Phe Val Gly Ala
            660                 665                 670
Ile Glu Leu Ala Gly Ile Thr Ala Leu Leu Glu Tyr Val Pro Glu Phe
            675                 680                 685
Thr Ile Pro Ile Leu Val Gly Leu Glu Val Ile Gly Gly Glu Leu Ala
            690                 695                 700
Arg Glu Gln Val Glu Ala Ile Val Asn Ala Leu Asp Lys Arg Asp
705                 710                 715                 720
Gln Lys Trp Ala Glu Val Tyr Asn Ile Thr Lys Ala Gln Trp Trp Gly
                    725                 730                 735
Thr Ile His Leu Gln Ile Asn Thr Arg Leu Ala His Thr Tyr Lys Ala
            740                 745                 750
Leu Ser Arg Gln Ala Asn Ala Ile Lys Met Asn Met Glu Phe Gln Leu
            755                 760                 765
Ala Asn Tyr Lys Gly Asn Ile Asp Asp Lys Ala Lys Ile Lys Asn Ala
            770                 775                 780
Ile Ser Glu Thr Glu Ile Leu Leu Asn Lys Ser Val Glu Gln Ala Met
785                 790                 795                 800
Lys Asn Thr Glu Lys Phe Met Ile Lys Leu Ser Asn Ser Tyr Leu Thr
                    805                 810                 815
Lys Glu Met Ile Pro Lys Val Gln Asp Asn Leu Lys Asn Phe Asp Leu
            820                 825                 830
Glu Thr Lys Lys Thr Leu Asp Lys Phe Ile Lys Glu Lys Glu Asp Ile
            835                 840                 845
Leu Gly Thr Asn Leu Ser Ser Ser Leu Arg Arg Lys Val Ser Ile Arg
850                 855                 860
Leu Asn Lys Asn Ile Ala Phe Asp Ile Asn Asp Ile Pro Phe Ser Glu
865                 870                 875                 880
Phe Asp Asp Leu Ile Asn Gln Tyr Lys Asn Glu Ile Glu Asp Tyr Glu
            885                 890                 895
Val Leu Asn Leu Gly Ala Glu Asp Gly Lys Ile Lys Asp Leu Ser Gly
            900                 905                 910
Thr Thr Ser Asp Ile Asn Ile Gly Ser Asp Ile Glu Leu Ala Asp Gly
            915                 920                 925
Arg Glu Asn Lys Ala Ile Lys Ile Lys Gly Ser Glu Asn Ser Thr Ile
            930                 935                 940
Lys Ile Ala Met Asn Lys Tyr Leu Arg Phe Ser Ala Thr Asp Asn Phe
945                 950                 955                 960
Ser Ile Ser Phe Trp Ile Lys His Pro Lys Pro Thr Asn Leu Leu Asn
                    965                 970                 975
Asn Gly Ile Glu Tyr Thr Leu Val Glu Asn Phe Asn Gln Arg Gly Trp
            980                 985                 990
Lys Ile Ser Ile Gln Asp Ser Lys Leu Ile Trp Tyr Leu Arg Asp His
            995                 1000                1005
Asn Asn Ser Ile Lys Ile Val Thr Pro Asp Tyr Ile Ala Phe Asn
        1010            1015            1020
Gly Trp Asn Leu Ile Thr Ile Thr Asn Asn Arg Ser Lys Gly Ser
        1025            1030            1035
Ile Val Tyr Val Asn Gly Ser Lys Ile Glu Glu Lys Asp Ile Ser
        1040            1045            1050
Ser Ile Trp Asn Thr Glu Val Asp Asp Pro Ile Ile Phe Arg Leu
        1055            1060            1065

```
Lys Asn Asn Arg Asp Thr Gln Ala Phe Thr Leu Leu Asp Gln Phe
    1070            1075                1080

Ser Ile Tyr Arg Lys Glu Leu Asn Gln Asn Glu Val Val Lys Leu
    1085            1090                1095

Tyr Asn Tyr Tyr Phe Asn Ser Asn Tyr Ile Arg Asp Ile Trp Gly
    1100            1105                1110

Asn Pro Leu Gln Tyr Asn Lys Lys Tyr Tyr Leu Gln Thr Gln Asp
    1115            1120                1125

Lys Pro Gly Lys Gly Leu Ile Arg Glu Tyr Trp Ser Ser Phe Gly
    1130            1135                1140

Tyr Asp Tyr Val Ile Leu Ser Asp Ser Lys Thr Ile Thr Phe Pro
    1145            1150                1155

Asn Asn Ile Arg Tyr Gly Ala Leu Tyr Asn Gly Ser Lys Val Leu
    1160            1165                1170

Ile Lys Asn Ser Lys Lys Leu Asp Gly Leu Val Arg Asn Lys Asp
    1175            1180                1185

Phe Ile Gln Leu Glu Ile Asp Gly Tyr Asn Met Gly Ile Ser Ala
    1190            1195                1200

Asp Arg Phe Asn Glu Asp Thr Asn Tyr Ile Gly Thr Thr Tyr Gly
    1205            1210                1215

Thr Thr His Asp Leu Thr Thr Asp Phe Glu Ile Ile Gln Arg Gln
    1220            1225                1230

Glu Lys Tyr Arg Asn Tyr Cys Gln Leu Lys Thr Pro Tyr Asn Ile
    1235            1240                1245

Phe His Lys Ser Gly Leu Met Ser Thr Glu Thr Ser Lys Pro Thr
    1250            1255                1260

Phe His Asp Tyr Arg Asp Trp Val Tyr Ser Ser Ala Trp Tyr Phe
    1265            1270                1275

Gln Asn Tyr Glu Asn Leu Asn Leu Arg Lys His Thr Lys Thr Asn
    1280            1285                1290

Trp Tyr Phe Ile Pro Lys Asp Glu Gly Trp Asp Glu Asp
    1295            1300                1305

<210> SEQ ID NO 42
<211> LENGTH: 141
<212> TYPE: PRT
<213> ORGANISM: Rattus norvegicus

<400> SEQUENCE: 42

Met Pro Pro Lys Phe Lys Arg His Leu Asn Asp Asp Val Thr Gly
1               5                   10                  15

Ser Val Lys Ser Glu Arg Arg Asn Leu Leu Glu Asp Ser Asp Glu
                20                  25                  30

Glu Glu Asp Phe Phe Leu Arg Gly Pro Ser Gly Pro Arg Phe Gly Pro
        35                  40                  45

Arg Asn Asp Lys Ile Lys His Val Gln Asn Gln Val Asp Glu Val Ile
    50                  55                  60

Asp Val Met Gln Glu Asn Ile Thr Lys Val Ile Glu Arg Gly Glu Arg
65                  70                  75                  80

Leu Asp Glu Leu Gln Asp Lys Ser Glu Ser Leu Ser Asp Asn Ala Thr
                85                  90                  95

Ala Phe Ser Asn Arg Ser Lys Gln Leu Arg Arg Gln Met Trp Trp Arg
                100                 105                 110

Gly Cys Lys Ile Lys Ala Ile Met Ala Leu Ala Ala Ala Ile Leu Leu
```

```
                115                 120                 125
Leu Met Ile Ile Thr Gln Ile Ile Leu His Leu Lys Lys
    130                 135                 140

<210> SEQ ID NO 43
<211> LENGTH: 141
<212> TYPE: PRT
<213> ORGANISM: Homo sapiens

<400> SEQUENCE: 43

Met Pro Pro Lys Phe Lys Arg His Leu Asn Asp Asp Val Thr Gly
1               5                   10                  15

Ser Val Lys Ser Glu Arg Arg Asn Leu Leu Glu Asp Ser Asp Glu
                20                  25                  30

Glu Glu Asp Phe Phe Leu Arg Gly Pro Ser Gly Pro Arg Phe Gly Pro
            35                  40                  45

Arg Asn Asp Lys Ile Lys His Val Gln Asn Gln Val Asp Glu Val Ile
50                  55                  60

Asp Val Met Gln Glu Asn Ile Thr Lys Val Ile Glu Arg Gly Glu Arg
65                  70                  75                  80

Leu Asp Glu Leu Gln Asp Lys Ser Glu Ser Leu Ser Asn Ala Thr
                85                  90                  95

Ala Phe Ser Asn Arg Ser Lys Gln Leu Arg Arg Gln Met Trp Trp Arg
            100                 105                 110

Gly Cys Lys Ile Lys Ala Ile Met Ala Leu Val Ala Ala Ile Leu Leu
            115                 120                 125

Leu Val Ile Ile Ile Leu Ile Val Met Lys Tyr Arg Thr
    130                 135                 140

<210> SEQ ID NO 44
<211> LENGTH: 102
<212> TYPE: PRT
<213> ORGANISM: Rattus norvegicus

<400> SEQUENCE: 44

Met Ala Gly Lys Glu Leu Glu Arg Cys Gln Arg Gln Ala Asp Gln Val
1               5                   10                  15

Thr Glu Ile Met Leu Asn Asn Phe Asp Lys Val Leu Glu Arg Asp Gly
                20                  25                  30

Lys Leu Ser Glu Leu Gln Gln Arg Ser Asp Gln Leu Leu Asp Met Ser
            35                  40                  45

Ser Ala Phe Ser Lys Thr Thr Lys Thr Leu Ala Gln Gln Lys Arg Trp
50                  55                  60

Glu Asn Ile Arg Cys Arg Val Tyr Leu Gly Leu Ala Val Ala Gly Gly
65                  70                  75                  80

Leu Leu Leu Ile Leu Val Val Leu Leu Val Ile Phe Leu Pro Ser Gly
                85                  90                  95

Glu Asp Ser Ser Lys Pro
            100

<210> SEQ ID NO 45
<211> LENGTH: 116
<212> TYPE: PRT
<213> ORGANISM: Homo sapiens

<400> SEQUENCE: 45

Met Ala Gly Ile Glu Leu Glu Arg Cys Gln Gln Gln Ala Asn Glu Val
1               5                   10                  15
```

-continued

```
Thr Glu Ile Met Arg Asn Asn Phe Gly Lys Val Leu Glu Arg Gly Val
             20                  25                  30

Lys Leu Ala Glu Leu Gln Gln Arg Ser Asp Gln Leu Leu Asp Met Ser
         35                  40                  45

Ser Thr Phe Asn Lys Thr Thr Gln Asn Leu Ala Gln Lys Lys Cys Trp
 50                  55                  60

Glu Asn Ile Arg Tyr Arg Ile Cys Val Gly Leu Val Val Gly Val
 65                  70                  75                  80

Leu Leu Ile Ile Leu Ile Val Leu Leu Val Val Phe Leu Pro Gln Ser
             85                  90                  95

Ser Asp Ser Ser Ser Ala Pro Arg Thr Gln Asp Ala Gly Ile Ala Ser
            100                 105                 110

Gly Pro Gly Asn
        115

<210> SEQ ID NO 46
<211> LENGTH: 198
<212> TYPE: PRT
<213> ORGANISM: Rattus norvegicus

<400> SEQUENCE: 46

Met Lys Leu Tyr Ser Leu Ser Val Phe Tyr Lys Gly Glu Pro Lys Ala
1               5                  10                  15

Val Leu Leu Lys Ala Ala Tyr Asp Val Ser Ser Phe Ser Phe Phe Gln
             20                  25                  30

Arg Ser Val Gln Glu Phe Met Thr Phe Thr Ser Gln Leu Ile Val
         35                  40                  45

Glu Arg Ser Ala Lys Gly Ser Arg Ala Ser Val Lys Glu Gln Glu Tyr
 50                  55                  60

Leu Cys His Val Tyr Val Arg Ser Asp Ser Leu Ala Gly Val Val Ile
 65                  70                  75                  80

Ala Asp Ser Glu Tyr Pro Ser Arg Val Ala Phe Thr Leu Leu Glu Lys
             85                  90                  95

Val Leu Asp Glu Phe Ser Lys Gln Val Asp Arg Ile Asp Trp Pro Val
            100                 105                 110

Gly Ser Pro Ala Thr Ile His Tyr Thr Ala Leu Asp Gly His Leu Ser
            115                 120                 125

Arg Tyr Gln Asn Pro Arg Glu Ala Asp Pro Met Ser Lys Val Gln Ala
        130                 135                 140

Glu Leu Asp Glu Thr Lys Ile Ile Leu His Asn Thr Met Glu Ser Leu
145                 150                 155                 160

Leu Glu Arg Gly Glu Lys Leu Asp Asp Leu Val Ser Lys Ser Glu Val
                165                 170                 175

Leu Gly Thr Gln Ser Lys Ala Phe Tyr Lys Thr Ala Arg Lys Gln Asn
            180                 185                 190

Ser Cys Cys Ala Ile Met
        195

<210> SEQ ID NO 47
<211> LENGTH: 198
<212> TYPE: PRT
<213> ORGANISM: Homo sapiens

<400> SEQUENCE: 47

Met Lys Leu Tyr Ser Leu Ser Val Leu Tyr Lys Gly Glu Ala Lys Val
1               5                  10                  15
```

```
Val Leu Leu Lys Ala Ala Tyr Asp Val Ser Ser Phe Ser Phe Phe Gln
         20                  25                  30

Arg Ser Ser Val Gln Glu Phe Met Thr Phe Thr Ser Gln Leu Ile Val
         35                  40                  45

Glu Arg Ser Ser Lys Gly Thr Arg Ala Ser Val Lys Glu Gln Asp Tyr
 50                  55                  60

Leu Cys His Val Tyr Val Arg Asn Asp Ser Leu Ala Gly Val Val Ile
 65                  70                  75                  80

Ala Asp Asn Glu Tyr Pro Ser Arg Val Ala Phe Thr Leu Leu Glu Lys
             85                  90                  95

Val Leu Asp Glu Phe Ser Lys Gln Val Asp Arg Ile Asp Trp Pro Val
        100                 105                 110

Gly Ser Pro Ala Thr Ile His Tyr Pro Ala Leu Asp Gly His Leu Ser
        115                 120                 125

Arg Tyr Gln Asn Pro Arg Glu Ala Asp Pro Met Thr Lys Val Gln Ala
130                 135                 140

Glu Leu Asp Glu Thr Lys Ile Ile Leu His Asn Thr Met Glu Ser Leu
145                 150                 155                 160

Leu Glu Arg Gly Glu Lys Leu Asp Asp Leu Val Ser Lys Ser Glu Val
                165                 170                 175

Leu Gly Thr Gln Ser Lys Ala Phe Tyr Lys Thr Ala Arg Lys Gln Asn
            180                 185                 190

Ser Cys Cys Ala Ile Met
            195

<210> SEQ ID NO 48
<211> LENGTH: 14
<212> TYPE: PRT
<213> ORGANISM: Artificial Sequence
<220> FEATURE:
<223> OTHER INFORMATION: VAMP epitope

<400> SEQUENCE: 48

Glu Thr Ser Ala Ala Lys Leu Lys Arg Lys Tyr Trp Trp Lys
1               5                   10

<210> SEQ ID NO 49
<211> LENGTH: 15
<212> TYPE: PRT
<213> ORGANISM: Artificial Sequence
<220> FEATURE:
<223> OTHER INFORMATION: VAMP epitope

<400> SEQUENCE: 49

Phe Glu Thr Ser Ala Ala Lys Leu Lys Arg Lys Tyr Trp Trp Lys
1               5                   10                  15

<210> SEQ ID NO 50
<211> LENGTH: 14
<212> TYPE: PRT
<213> ORGANISM: Artificial Sequence
<220> FEATURE:
<223> OTHER INFORMATION: VAMP epitope

<400> SEQUENCE: 50

Gln Phe Glu Ser Ser Ala Ala Lys Leu Lys Arg Lys Tyr Trp
1               5                   10

<210> SEQ ID NO 51
<211> LENGTH: 10
```

```
<212> TYPE: PRT
<213> ORGANISM: Artificial Sequence
<220> FEATURE:
<223> OTHER INFORMATION: VAMP epitope

<400> SEQUENCE: 51

Phe Glu Ser Ser Ala Ala Lys Leu Lys Arg
1               5                   10

<210> SEQ ID NO 52
<211> LENGTH: 15
<212> TYPE: PRT
<213> ORGANISM: Artificial Sequence
<220> FEATURE:
<223> OTHER INFORMATION: VAMP epitope

<400> SEQUENCE: 52

Phe Glu Ser Ser Ala Ala Lys Leu Lys Arg Lys Tyr Trp Trp Lys
1               5                   10                  15

<210> SEQ ID NO 53
<211> LENGTH: 11
<212> TYPE: PRT
<213> ORGANISM: Artificial Sequence
<220> FEATURE:
<223> OTHER INFORMATION: VAMP epitope

<400> SEQUENCE: 53

Ala Asp Ala Leu Gln Ala Gly Ala Ser Gln Phe
1               5                   10

<210> SEQ ID NO 54
<211> LENGTH: 10
<212> TYPE: PRT
<213> ORGANISM: Artificial Sequence
<220> FEATURE:
<223> OTHER INFORMATION: VAMP epitope

<400> SEQUENCE: 54

Ala Asp Ala Leu Gln Ala Gly Ala Ser Gln
1               5                   10

<210> SEQ ID NO 55
<211> LENGTH: 12
<212> TYPE: PRT
<213> ORGANISM: Artificial Sequence
<220> FEATURE:
<223> OTHER INFORMATION: VAMP epitope

<400> SEQUENCE: 55

Arg Ala Asp Ala Leu Gln Ala Gly Ala Ser Gln Phe
1               5                   10

<210> SEQ ID NO 56
<211> LENGTH: 12
<212> TYPE: PRT
<213> ORGANISM: Artificial Sequence
<220> FEATURE:
<223> OTHER INFORMATION: VAMP epitope

<400> SEQUENCE: 56

Ala Asp Ala Leu Gln Ala Gly Ala Ser Gln Phe Glu
1               5                   10

<210> SEQ ID NO 57
<211> LENGTH: 11
<212> TYPE: PRT
```

```
<213> ORGANISM: Artificial Sequence
<220> FEATURE:
<223> OTHER INFORMATION: VAMP epitope

<400> SEQUENCE: 57

Ala Asp Ala Leu Gln Ala Gly Ala Ser Val Phe
1               5                   10

<210> SEQ ID NO 58
<211> LENGTH: 10
<212> TYPE: PRT
<213> ORGANISM: Artificial Sequence
<220> FEATURE:
<223> OTHER INFORMATION: VAMP epitope

<400> SEQUENCE: 58

Ala Asp Ala Leu Gln Ala Gly Ala Ser Val
1               5                   10

<210> SEQ ID NO 59
<211> LENGTH: 12
<212> TYPE: PRT
<213> ORGANISM: Artificial Sequence
<220> FEATURE:
<223> OTHER INFORMATION: VAMP epitope

<400> SEQUENCE: 59

Ala Asp Ala Leu Gln Ala Gly Ala Ser Val Phe Glu
1               5                   10

<210> SEQ ID NO 60
<211> LENGTH: 12
<212> TYPE: PRT
<213> ORGANISM: Artificial Sequence
<220> FEATURE:
<223> OTHER INFORMATION: VAMP epitope

<400> SEQUENCE: 60

Arg Ala Asp Ala Leu Gln Ala Gly Ala Ser Val Phe
1               5                   10

<210> SEQ ID NO 61
<211> LENGTH: 10
<212> TYPE: PRT
<213> ORGANISM: Artificial Sequence
<220> FEATURE:
<223> OTHER INFORMATION: VAMP epitope

<400> SEQUENCE: 61

Arg Ala Asp Ala Leu Gln Ala Gly Ala Ser
1               5                   10

<210> SEQ ID NO 62
<211> LENGTH: 11
<212> TYPE: PRT
<213> ORGANISM: Artificial Sequence
<220> FEATURE:
<223> OTHER INFORMATION: VAMP epitope

<400> SEQUENCE: 62

Ser Glu Ser Leu Ser Asp Asn Ala Thr Ala Phe
1               5                   10

<210> SEQ ID NO 63
<211> LENGTH: 10
<212> TYPE: PRT
<213> ORGANISM: Artificial Sequence
```

```
<220> FEATURE:
<223> OTHER INFORMATION: VAMP epitope

<400> SEQUENCE: 63

Ser Glu Ser Leu Ser Asp Asn Ala Thr Ala
1               5                   10

<210> SEQ ID NO 64
<211> LENGTH: 12
<212> TYPE: PRT
<213> ORGANISM: Artificial Sequence
<220> FEATURE:
<223> OTHER INFORMATION: VAMP epitope

<400> SEQUENCE: 64

Lys Ser Glu Ser Leu Ser Asp Asn Ala Thr Ala Phe
1               5                   10

<210> SEQ ID NO 65
<211> LENGTH: 12
<212> TYPE: PRT
<213> ORGANISM: Artificial Sequence
<220> FEATURE:
<223> OTHER INFORMATION: VAMP epitope

<400> SEQUENCE: 65

Ser Glu Ser Leu Ser Asp Asn Ala Thr Ala Phe Ser
1               5                   10

<210> SEQ ID NO 66
<211> LENGTH: 11
<212> TYPE: PRT
<213> ORGANISM: Artificial Sequence
<220> FEATURE:
<223> OTHER INFORMATION: VAMP epitope

<400> SEQUENCE: 66

Ser Asp Gln Leu Leu Asp Met Ser Ser Thr Phe
1               5                   10

<210> SEQ ID NO 67
<211> LENGTH: 10
<212> TYPE: PRT
<213> ORGANISM: Artificial Sequence
<220> FEATURE:
<223> OTHER INFORMATION: VAMP epitope

<400> SEQUENCE: 67

Ser Asp Gln Leu Leu Asp Met Ser Ser Thr
1               5                   10

<210> SEQ ID NO 68
<211> LENGTH: 12
<212> TYPE: PRT
<213> ORGANISM: Artificial Sequence
<220> FEATURE:
<223> OTHER INFORMATION: VAMP epitope

<400> SEQUENCE: 68

Arg Ser Asp Gln Leu Leu Asp Met Ser Ser Thr Phe
1               5                   10

<210> SEQ ID NO 69
<211> LENGTH: 12
<212> TYPE: PRT
<213> ORGANISM: Artificial Sequence
<220> FEATURE:
```

<223> OTHER INFORMATION: VAMP epitope

<400> SEQUENCE: 69

Ser Asp Gln Leu Leu Asp Met Ser Ser Thr Phe Asn
1               5                   10

<210> SEQ ID NO 70
<211> LENGTH: 11
<212> TYPE: PRT
<213> ORGANISM: Artificial Sequence
<220> FEATURE:
<223> OTHER INFORMATION: VAMP epitope

<400> SEQUENCE: 70

Ser Asp Gln Leu Leu Asp Met Ser Ser Ala Phe
1               5                   10

<210> SEQ ID NO 71
<211> LENGTH: 10
<212> TYPE: PRT
<213> ORGANISM: Artificial Sequence
<220> FEATURE:
<223> OTHER INFORMATION: VAMP epitope

<400> SEQUENCE: 71

Ser Asp Gln Leu Leu Asp Met Ser Ser Ala
1               5                   10

<210> SEQ ID NO 72
<211> LENGTH: 12
<212> TYPE: PRT
<213> ORGANISM: Artificial Sequence
<220> FEATURE:
<223> OTHER INFORMATION: VAMP epitope

<400> SEQUENCE: 72

Arg Ser Asp Gln Leu Leu Asp Met Ser Ser Ala Phe
1               5                   10

<210> SEQ ID NO 73
<211> LENGTH: 12
<212> TYPE: PRT
<213> ORGANISM: Artificial Sequence
<220> FEATURE:
<223> OTHER INFORMATION: VAMP epitope

<400> SEQUENCE: 73

Ser Asp Gln Leu Leu Asp Met Ser Ser Ala Phe Ser
1               5                   10

<210> SEQ ID NO 74
<211> LENGTH: 10
<212> TYPE: PRT
<213> ORGANISM: Artificial Sequence
<220> FEATURE:
<223> OTHER INFORMATION: VAMP epitope

<400> SEQUENCE: 74

Arg Ser Asp Gln Leu Leu Asp Met Ser Ser
1               5                   10

<210> SEQ ID NO 75
<211> LENGTH: 11
<212> TYPE: PRT
<213> ORGANISM: Artificial Sequence
<220> FEATURE:
<223> OTHER INFORMATION: VAMP epitope

```
<400> SEQUENCE: 75

Ser Glu Val Leu Gly Thr Gln Ser Lys Ala Phe
1               5                   10

<210> SEQ ID NO 76
<211> LENGTH: 10
<212> TYPE: PRT
<213> ORGANISM: Artificial Sequence
<220> FEATURE:
<223> OTHER INFORMATION: VAMP epitope

<400> SEQUENCE: 76

Ser Glu Val Leu Gly Thr Gln Ser Lys Ala
1               5                   10

<210> SEQ ID NO 77
<211> LENGTH: 12
<212> TYPE: PRT
<213> ORGANISM: Artificial Sequence
<220> FEATURE:
<223> OTHER INFORMATION: VAMP epitope

<400> SEQUENCE: 77

Lys Ser Glu Val Leu Gly Thr Gln Ser Lys Ala Phe
1               5                   10

<210> SEQ ID NO 78
<211> LENGTH: 12
<212> TYPE: PRT
<213> ORGANISM: Artificial Sequence
<220> FEATURE:
<223> OTHER INFORMATION: VAMP epitope

<400> SEQUENCE: 78

Ser Glu Val Leu Gly Thr Gln Ser Lys Ala Phe Tyr
1               5                   10
```

UNITED STATES PATENT AND TRADEMARK OFFICE
CERTIFICATE OF CORRECTION

PATENT NO. : 11,193,931 B2
APPLICATION NO. : 16/335358
DATED : December 7, 2021
INVENTOR(S) : Bryony Gray et al.

Page 1 of 1

It is certified that error appears in the above-identified patent and that said Letters Patent is hereby corrected as shown below:

In the Specification

Column 1, Line 7, replace "PCT/FT 2017/076569" with --PCT/EP2017/076569--.

Column 1, Line 8, insert --which-- between "2017," and "claims".

In the Claims

Claim 1, replace "22-3o" with --22-30--.

Claim 5, replace "22-3o" with --22-30--.

Claim 5, replace "1S-24" with --15-34--.

Signed and Sealed this
First Day of March, 2022

Drew Hirshfeld
*Performing the Functions and Duties of the*
*Under Secretary of Commerce for Intellectual Property and*
*Director of the United States Patent and Trademark Office*